US007307065B2

(12) United States Patent
Schinazi et al.

(10) Patent No.: US 7,307,065 B2
(45) Date of Patent: *Dec. 11, 2007

(54) 2'-FLUORONUCLEOSIDES

(75) Inventors: Raymond F. Schinazi, Decatur, GA (US); Dennis C. Liotta, McDonough, GA (US); Chung K. Chu, Athens, GA (US); J. Jeffrey McAtee, Atlanta, GA (US); Junxing Shi, Decatur, GA (US); Yongseok Choi, Athens, GA (US); Kyeong Lee, Athens, GA (US); Joon H. Hong, Athens, GA (US)

(73) Assignees: Emory University, Atlanta, GA (US); The University of Georgia Research Foundation, Inc., Athens, GA (US)

( * ) Notice: Subject to any disclaimer, the term of this patent is extended or adjusted under 35 U.S.C. 154(b) by 333 days.

This patent is subject to a terminal disclaimer.

(21) Appl. No.: 10/796,529

(22) Filed: Mar. 8, 2004

(65) Prior Publication Data

US 2004/0254141 A1    Dec. 16, 2004

Related U.S. Application Data

(63) Continuation of application No. 10/061,128, filed on Jan. 30, 2002, now Pat. No. 6,911,424, which is a continuation of application No. 09/257,130, filed on Feb. 25, 1999, now Pat. No. 6,348,587.

(60) Provisional application No. 60/080,569, filed on Apr. 3, 1998, provisional application No. 60/075,893, filed on Feb. 25, 1998.

(51) Int. Cl.
*A61K 38/00* (2006.01)
*A01N 61/00* (2006.01)
*C07H 1/00* (2006.01)
*C07G 3/00* (2006.01)

(52) U.S. Cl. .......................... 514/44; 514/1; 536/1.11; 536/4.1

(58) Field of Classification Search .................... 514/1, 514/44; 536/1.11, 4.1
See application file for complete search history.

(56) References Cited

U.S. PATENT DOCUMENTS

| | | |
|---|---|---|
| 4,000,137 A | 12/1976 | Dvonch et al. |
| 4,211,773 A | 7/1980 | Lopez et al. |
| 4,336,381 A | 6/1982 | Nagata et al. |
| 4,625,020 A | 11/1986 | Brundidge et al. |
| 4,666,892 A | 5/1987 | Fox et al. |
| 4,908,440 A | 3/1990 | Sterzycki et al. |
| 5,034,518 A | 7/1991 | Montgomery et al. |
| 5,128,458 A | 7/1992 | Montgomery et al. |
| 5,210,085 A | 5/1993 | Liotta et al. |

(Continued)

FOREIGN PATENT DOCUMENTS

EP    0292023 A2    5/1988

(Continued)

OTHER PUBLICATIONS

Balakrishna, P.S., et al., "Inhibition of Hepatitis B. Virus by a Novel L-Nucleoside, 2'-Fluoro-5-Menthyl—L- arabinofuranosyl Uracil," *Amtimicrobial Agents and Chemotherapy*, 40(2):380-386 (Feb. 1996).

(Continued)

*Primary Examiner*—Jezia Riley
(74) *Attorney, Agent, or Firm*—King & Spalding

(57) ABSTRACT

A class of 2'-fluoro-nucleoside compounds are disclosed which are useful in the treatment of hepatitis B infection, hepatitis C infection, HIV and abnormal cellular proliferation, including tumors and cancer. The compounds have the general formulae:

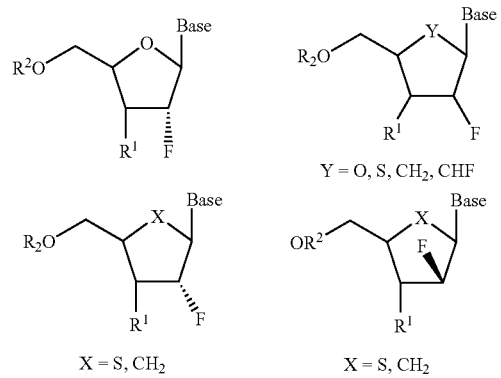

$Y = O, S, CH_2, CHF$ $X = S, CH_2$       $X = S, CH_2$ wherein
Base is a purine or pyrimidine base;
$R^1$ is OH, H, $OR^3$, $N_3$, CN, halogen, including F, or $CF_3$, lower alkyl, amino, loweralkylamino, di(lower)alkylamino, or alkoxy, and base refers to a purine or pyrimidine base;
$R^2$ is H, phosphate, including monophosphate, diphosphate, triphosphate, or a stabilized phosphate prodrug; acyl, or other pharmaceutically acceptable leaving group which when administered in vivo, is capable of providing a compound wherein $R^2$ is H or phosphate; sulfonate ester including alkyl or arylalkyl sulfonyl including methanesulfonyl, benzyl, wherein the phenyl group is optionally substituted with one or more substituents as described in the definition of aryl given above, a lipid, an amino acid, peptide, or cholesterol; and
$R^3$ is acyl, alkyl, phosphate, or other pharmaceutically acceptable leaving group which when administered in vivo, is capable of being cleaved to the parent compound, or a pharmaceutically acceptable salt thereof.

24 Claims, No Drawings

U.S. PATENT DOCUMENTS

| | | | |
|---|---|---|---|
| 5,246,924 A | 9/1993 | Fox et al. | |
| 5,424,416 A | 6/1995 | Jones et al. | |
| 5,426,183 A | 6/1995 | Kjell et al. | |
| 5,446,029 A | 8/1995 | Eriksson et al. | |
| 5,512,671 A | 4/1996 | Piantodosi et al. | |
| 5,565,438 A | 10/1996 | Chu et al. | |
| 5,567,688 A | 10/1996 | Chu et al. | |
| 5,587,362 A | 12/1996 | Chu et al. | |
| 5,703,058 A | 12/1997 | Schinazi et al. | |
| 5,808,040 A | 9/1998 | Chu et al. | |
| 5,817,799 A | 10/1998 | Marquez et al. | |
| 5,886,162 A | 3/1999 | Kalman et al. | |
| 5,905,070 A | 5/1999 | Schinazi et al. | |
| 6,103,707 A | 8/2000 | Yamada et al. | |
| 6,147,058 A | 11/2000 | Yoshimura et al. | |
| 6,232,300 B1 | 5/2001 | Schinazi et al. | |
| 6,348,587 B1 * | 2/2002 | Schinazi et al. | 536/25.3 |
| 6,407,077 B1 | 6/2002 | Gosselin et al. | |
| 6,458,773 B1 | 10/2002 | Gosselin et al. | |
| 6,911,424 B2 * | 6/2005 | Schinazi et al. | 514/1 |
| 2002/0198171 A1 | 12/2002 | Schinazi et al. | |

FOREIGN PATENT DOCUMENTS

| | | |
|---|---|---|
| EP | 0316017 A2 | 5/1989 |
| EP | 0 352 248 A1 | 1/1990 |
| EP | 0382526 A2 | 8/1990 |
| EP | 0409227 A2 | 1/1991 |
| EP | 0463470 A2 | 1/1992 |
| EP | 0357571 B1 | 4/1996 |
| EP | 0839813 A1 | 5/1998 |
| WO | WO88/08001 A1 | 10/1988 |
| WO | WO91/11186 A1 | 8/1991 |
| WO | WO92/08727 A1 | 5/1992 |
| WO | WO92/14743 A2 | 9/1992 |
| WO | WO94/14831 A1 | 7/1994 |
| WO | WO95/20595 A1 | 8/1995 |
| WO | WO96/22778 A1 | 8/1996 |
| WO | WO96/40164 A1 | 12/1996 |
| WO | WO97/28177 A1 | 8/1997 |
| WO | WO97/37993 A1 | 10/1997 |
| WO | WO98/18430 A2 | 5/1998 |
| WO | WO99/43691 A1 | 9/1999 |

OTHER PUBLICATIONS

Borthwick, et al., "Synthesis and Enzymatic Resolution of Carbocyclic 2'-Ara-fluoro-Guanosine; A Potent New Anti-Herpetic Agent," J. Chem Soc., Chem. Commun., (1988).

Bouffard, D.Y., et al., "Kinetic Studies of 2',2'-Difluorodeoxycytidine (Gemcitabine) with Purified Human Deoxycytidine Kinase and Cytidine Deaminase," Biochemical Pharmacology, 45(9):1857-1861 (May 5, 1993).

Cheng, et al., "Deoxycytidine deaminase-resistant stereoisomer is the active form of (+/−)-2',3'-dideoxy-3'-thiacytidine in the inhibition of hepatitis B virus replication," Journal of Biological Chemistry, vol. 267(20):13938-13942 (Jul. 1992).

Chu, et al., "Use of 2'-Fluoro-5-methyl—L-arabinofuranosyluracil as a Novel Antiviral Agent for Hepatitis B. Virus and Epstein-Barr Virus" Antimicrobial Agents and Chemotherapy, 39(4):979-981 (Apr. 1995).

Furman, et al., "The Anti-Hepatitis B. Virus Activities, Cytotoxicities, and Anabolic Profiles of the (−) and (+) Enantiomers of cis-5-Fluoro-1[2-(Hydroxymethyl)-1, 3-oxathiolane-5-yl]-Cytosine" Antimicrobial Agents and Chemotherapy, 36(12):2686-2692 (Dec. 1992).

Jeong, L.S., et al., "Facile Fluorination of Deoxy-4'-thiopyrimidine Nucleosides with 'Down' Hydroxyl Groups. Retention of Configuration After Fluoride Opening of the Quaternized $N^3$-MEM Anhydronucleosides," Tetrahedron Letters, 35(41):7573-7576 (1994).

Jeong, L.S., et al., "Unanticipated Retention of Configuration in the DAST Fluorination of Deoxy-4'-thiopyrimidine Nucleosides with 'Up' Hydroxyl Groups," Tetrahedron Letters, 35(41):7569-7572 (1994).

Machida, H., et al., "Anti-herpesvirus activity profile of 4'-thioarabinofuranosyl purine and uracil nucleosides and activity of 1-beta-D-2'-fluoro-4'-thioarabinofuranosyl guanine and 2,6-diaminopurine against clinical isolates of human cytomegalovirus." Antiviral Res., 39(2):129-137 (Aug. 1998).

Marquez, V.E., et al., Nucleosides & Nucleotides, 14(3-5):555-558 (1995).

Martin, et al., Synthesis and Antiviral Activity of Monofluoro and Difluoro Analogues of Pyrimidine Deoxyribonucleosides against Human Immunodeficiency Virus (HIV-1), J. Med., Chem., 33:2137-2145 (1990).

Montgomery, J.A., et al., "9-(2-Deoxy-2-fluoro-β-D-arabinofuranosyl)guanine: A Metabolically Stable Cytotoxic Analogue of 2'-Deoxyguanosine," J. Med. Chem., 29(11):2389-2392 (Nov. 1986).

Niihata, S., et al., "Synthesis of 2-Fluoro Sugar and Its Condensation Reaction with Silylated Thymine," Bull. Chem. Soc. Jpn. 68(5):1509-1512 (May 1995).

Okabe, M., et al., "Synthesis of 1-(2,3-Dideoxy-2-fluoro-β-D-threo-pentofuranosyl)cytosine (F-ddC). A Promising Agent for the Treatment of Acquired Immune Deficiency Syndrome," J. Org. Chem. 56:4392-4397 (Feb. 1991).

Schinazi, et al., "Selective Inhibition of Human Immunodefiency viruses by Racemates and Enantiomers of cis-5-Fluoro-1-2[Hydroxymethyl)-1, 3-Oxathiolane-5-Yl]Cytosine" Antimicrobial Agents and Chemotherapy, 36(11):2423-2431 (Nov. 1992).

Schinazi, et al., Mutations in retroviral genes associated with drug resistance, International Antiviral News (1997).

Siddiqui, M.A., et al., "A New Synthetic Approach to the Clinically Useful, Anti-HIV Active Nucleoside, 9-(2,3-Dideoxy-2-fluoro-beta-D-threo-pentofuranosyl)adenine (beta-FddA). Introduction of a 2'-beta-Fluoro Substituent via Inversion of a Readily Obtainable 2'-alpha-Fluoro Isomer," Tetrahedron Letters, 39(13):1657-1660 (Mar. 26, 1998).

Sterzycki, et al., "Synthesis and Anti-HIV Activity of Several 2'-Fluoro-Containing Pyrimidine Nucleosides," J. Med. Chem., 33(8):2150-2157 (Aug. 1990).

Su, T.S., et al., "Sytesis and Antiviral Effects of Several 1-(2-Deoxy-2-fluoro-B-D-arabinofuranosyl)-5-alkyluracils. Some Structure-Activity Relationships," J. Med. Chem., 29:151-154 (1986).

Toyota, A., et al., Tetrahedron, 51(32):8783-8798 (1995).

Van Aerschot, A., et al., "3'-Fluoro-2',3'-dideoxy-5-chlorouridine: Most Selective Anti-HIV-1 Agent among a Series of New 2'- and 3'-Fluorinated 2',3'-Dideoxynucleoside Analogues.", J. Med. Chem. 32(8):1743-1749 (Aug. 1989).

Wantanabe, et al., "Synthesis and Anti-HIV Activity of 2'-"Up"-Fluoro Analogues of Active Anti-Aids Nucleosides 3'-Azido-3'deoxythymidine (AZT) and 2', 3'-dideoxycytidinee (DDC)," J. Med. Chem., 33:2145-2150 (1990).

Yoahimura, Y., et al., J. Org. Chem., 64:7912-7920 (1999).

* cited by examiner

2'-FLUORONUCLEOSIDES

This application is a continuation application of U.S. application Ser. No. 10/061,128, filed on Jan. 30, 2002, now U.S. Pat. No. 6,911,424 which is a continuation application of U.S. patent application Ser. No. 09/257,130, filed on Feb. 25, 1999, now U.S. Pat. No. 6,348,587, which claims priority to U.S. provisional application No. 60/075,893, filed on Feb. 25, 1998, and U.S. provisional application No. 60/080,569, filed on Apr. 3, 1998. The invention described herein was made with Government support under grant number AI32351 awarded by the National Institutes of Health. The United States Government has certain rights to this invention.

This invention is in the area of pharmaceutical chemistry, and in particular, includes 2'-fluoronucleosides and methods for their preparation and use.

BACKGROUND OF THE INVENTION

Synthetic nucleosides such as 5-iodo-2'-deoxyuridine and 5-fluoro-2'-deoxyuridine have been used for the treatment of cancer and herpes viruses for a number of years. Since the 1980's, synthetic nucleosides have also been a focus of interest for the treatment of HIV, hepatitis, and Epstein-Barr viruses.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing stand of viral DNA, causing chain termination due to the absence of the 3'-hydroxyl group. They can also inhibit the viral enzyme reverse transciptase.

The success of various synthetic nucleosides in inhibiting the replication of HIV in vivo or in vitro has led a number of researchers to design and test nucleosides that substitute a heteroatom for the carbon atom at the 3'-position of the nucleoside. European Patent Application Publication No. 0 337 713 and U.S. Pat. No. 5,041,449, assigned to BioChem Pharma, Inc., disclose racemic 2-substituted-4-substituted-1,3-dioxolanes that exhibit antiviral activity. U.S. Pat. No. 5,047,407 and European Patent Application No. 0 382 526, also assigned to BioChem Pharma, Inc., disclose that a number of racemic 2-substituted-5-substituted-1,3-oxathiolane nucleosides have antiviral activity, and specifically report that the racemic mixture of 2-hydroxymethyl-5-(cytosin-1-yl)-1,3-oxathiolane (referred to below as BCH-189) has approximately the same activity against HIV as AZT, with little toxicity. The (–)-enantiomer of the racemate BCH-189, known as 3TC, which is covered by U.S. Pat. No. 5,539,116 to Liotta et al., is currently sold for the treatment of HIV in combination with AZT in humans in the U.S.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency viruses by Racemates and Enantiomers of cis-5-Fluoro-1-[2-(Hydroxymethyl)-1,3-Oxathiolane-5-yl]Cytosine" *Antimicrobial Agents and Chemotherapy*, November 1992, pp. 2423-2431. See also U.S. Pat. No. 5,210,085; WO 91/11186, and WO 92/14743.

Another virus that causes a serious human health problem is the hepatitis B virus (referred to below as "HBV"). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome, which accounts for why HBV infection is common among patients infected with HIV or AIDS. However, HBV is more contagious than HIV.

Both FTC and 3TC exhibit activity against HBV. Furman, et al., "The Anti-Hepatitis B Virus Activities, Cytotoxicities, and Anabolic Profiles of the (–) and (+) Enantiomers of cis-5-Fluoro-1-[2-(Hydroxymethyl)-1,3-oxathiolane-5-yl]-Cytosine" *Antimicrobial Agents and Chemotherapy*, December 1992, pp. 2686-2692; and Cheng, et al., *Journal of Biological Chemistry*, Volume 267(20), pp.13938-13942 (1992).

A human serum-derived vaccine has been developed to immunize patients against HBV. While it has been found effective, production of the vaccine is troublesome because the supply of human serum from chronic carriers is limited, and the purification procedure is long and expensive. Further, each batch of vaccine prepared from different serum must be tested in chimpanzees to ensure safety. Vaccines have also been produced through genetic engineering. Daily treatments with a-interferon, a genetically engineered protein, has also shown promise.

Hepatitis C virus ("HCV") is the major causative agent for post-transfusion and for sporadic non A, non B hepatitis (Alter, H. J. (1990) *J. Gastro. Hepatol.* 1:78-94; Dienstag, J. L. (1983) *Gastro* 85:439-462). Despite improved screening, HCV still accounts for at least 25% of the acute viral hepatitis in many countries (Alter, H. J. (1990) supra; Dienstag, J. L. (1983) supra; Alter M. J. et al. (1990a) *J.A.M.A.* 264:2231-2235; Alter M. J. et al (1992) *N. Engl. J. Med.* 327:1899-1905; Alter, M. J. et al. (1990b) *N. Engl. J. Med.* 321:1494-1500). Infection by HCV is insidious in a high proportion of chronically infected (and infectious) carriers who may not experience clinical symptoms for many years. The high rate of progression of acute infection to chronic infection (70-100%) and liver disease (>50%), its world-wide distribution and lack of a vaccine make HCV a significant cause of morbidity and mortality.

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is now the second leading cause of death in the United States. Over 8,000,000 persons in the United States have been diagnosed with cancer, with 1,208,000 new diagnoses expected in 1994. Over 500,000 people die annually from the disease in this country.

Cancer is not fully understood on the molecular level. It is known that exposure of a cell to a carcinogen such as certain viruses, certain chemicals, or radiation, leads to DNA alteration that inactivates a "suppressive" gene or activates an "oncogene". Suppressive genes are growth regulatory genes, which upon mutation, can no longer control cell growth. Oncogenes are initially normal genes (called proon-congenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three years of therapies: surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia.

Chemotherapy involves the disruption of cell replication or cell metabolism. It is used most often in the treatment of leukemia, as well as breast, lung, and testicular cancer.

There are five major classes of chemotherapeutic agents currently in use for the treatment of cancer: natural products and their derivatives; anthacyclines; alkylating agents; antiproliferatives (also called antimetabolites); and hormonal agents. Chemotherapeutic agents are often referred to as antineoplastic agents.

The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attach malignant cells, but also other cells which are naturally dividing, such as those of bone marrow, skin, gastro-intestinal mucosa, and fetal tissue.

Antimetabolites are typically reversible or irreversible enzyme inhibitors, or compounds that otherwise interfere with the replication, translation or transcription of nucleic acids.

Several synthetic nucleosides have been identified that exhibit anticancer activity. A well known nucleoside derivative with strong anticancer activity is 5-fluorouracil. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381.

U.S. Pat. No. 4,000,137 discloses that the peroxidate oxidation product of inosine, adenosine, or cytidine with methanol or ethanol has activity against lymphocytic leukemia.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites", *Cancer Medicine*, Chapter XV-1, 3rd Edition, Edited by J. Holland, et al., Lea and Febigol, publishers.

5-Azacytidine is a cytidine analog that is primarily used in the treatment of acute myelocytic leukemia and myelodysplastic syndrome.

2-Fluoroadenosine-5'-phosphate (Fludara, also referred to as FaraA)) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. Incorporation of the active metabolite, F-araATP, retards DNA chain elongation. F-araA is also a potent inhibitor of ribonucleotide reductase, the key enzyme responsible for the formation of dATP.

2-Chlorodeoxyadenosine is useful in the treatment of low grade B-cell neoplasms such as chronic lymphocytic leukemia, non-Hodgkins' lymphoma, and hairy-cell leukemia.

In designing new biologically active nucleosides, there have been a number of attempts to incorporate a fluoro substituent into the carbohydrate ring of the nucleoside. Fluorine has been suggested as a substituent because it might serve as an isopolar and isosteric mimic of a hydroxyl group as the C—F bond length (1.35 Å) is so similar to the C—O bond length (1.43 Å) and because fluorine is a hydrogen bond acceptor. Fluorine is capable of producing significant electronic changes in a molecule with minimal steric perturbation. The substitution of fluorine for another group in a molecule can cause changes in substrate metabolism because of the high strength of the C—F bond (116 kcal/mol vs. C—H=100 kcal/mol).

A number of references have reported the synthesis and use of 2'-arabinofluoro-nucleosides (i.e., nucleosides in which a 2'-fluoro group is in the "up"-configuration). There have been several reports of 2-fluoro-β-D-arabinofuranosyl nucleosides that exhibit activity against hepatitis B and herpes. See, for example, U.S. Pat. No. 4,666,892 to Fox, et al.; U.S. Pat. No. 4,211,773 to Lopez, et al; Su, et al., Nucleosides. 136, "Synthesis and Antiviral Effects of Several 1-(2-Deoxy-2-fluoro-β-D-arabinofuranosyl)-5-alkyluracils." "Some Structure-Activity Relationships," *J. Med. Chem.*, 1986, 29, 151-154; Borthwick, et al., "Synthesis and Enzymatic Resolution of Carbocyclic 2'-Ara-fluoro-Guanosine: A Potent New Anti-Herpetic Agent," *J. Chem. Soc., Chem. Commun*, 1988; Wantanabe, et al., "Synthesis and Anti-HIV Activity of 2'-"Up"-Fluoro Analogues of Active Anti-Aids Nucleosides 3'-Azido-3'-deoxythymidine (AZT) and 2',3'-dideoxycytidine (DDC)," *J. Med. Chem.* 1990, 33, 2145-2150; Martin, et al., "Synthesis and Antiviral Activity of Monofluoro and Difluoro Analogues of Pyrimidine Deoxyribonucleosides against Human Immunodeficiency Virus (HIV-1)," *J. Med., Chem.* 1990, 33, 2137-2145; Sterzycki, et al., "Synthesis and Anti-HIV Activity of Several 2'-Fluoro-Containing Pyrimidine Nucleosides," *J. Med. Chem.* 1990, as well as EPA 0 316 017 also filed by Sterzycki, et al.; and Montgomery, et al., "9-(2-Deoxy-2-fluoro-β-D-arabinofuranosyl)guanine: A Metabolically Stable Cytotoxic Analogue of 2'-Deoxyguanosine." U.S. Pat. No. 5,246,924 discloses a method for treating a hepatitis infection that includes the administration of 1-(2'-deoxy-2'-fluoro-β-D-arabinofuranosyl)-3-ethyluracil), also referred to as "FEAU." U.S. Pat. No. 5,034,518 discloses 2-fluoro-9-(2-deoxy-2-fluoro-β-D-arabinofuranosyl)adenine nucleosides which exhibit anticancer activity by altering the metabolism of adenine nucleosides by reducing the ability of the compound to serve as a substrate for adenosine. EPA 0 292 023 discloses that certain β-D-2'-fluoroarabinonucleosides are active against viral infections.

U.S. Pat. No. 5,128,458 discloses β-D-2',3'-dideoxy-4'-thioribonucleosides as antiviral agents. U.S. Pat. No. 5,446,029 discloses that 2',3'-dideoxy-3'-fluoronucleosides have antihepatitis activity.

European Patent Application No. 0 409 227 A2 discloses certain 3'-substituted β-D-pyrimidine and purine nucleosides for the treatment of hepatitis B.

It has also been disclosed that L-FMAU (2'-fluoro-5-methyl-β-L-arabinofuranosyluracil) is a potent anti-HBV and anti-EBV agent. See Chu, et al., "Use of 2'-Fluoro-5-methyl-β-L-arabinofuranosyluracil as a Novel Antiviral Agent for Hepatitis B Virus and Epstein-Barr Virus" *Antimicrobial Agents and Chemotherapy*, April 1995 pages. 979-981; Balakrishna, et al., "Inhibition of Hepatitis B Virus by a Novel L-Nucleoside, 2'-Fluoro-5-Methyl-β-L arabinofuranosyl Uracil," *Antimicrobial Agents and Chemotherapy*, February 1996, pages 380-356; U.S. Pat. Nos. 5,587,362; 5,567,688; and 5,565,438.

U.S. Pat. Nos. 5,426,183 and 5,424,416 disclose processes for preparing 2'-deoxy-2',2'-difluoronucleosides and 2'-deoxy-2'-fluoro nucleosides. See also "Kinetic Studies of 2',2'-difluorodeoxycytidine (Gemcitabine) with Purified Human Deoxycytidine Kinase and Cytidine Deaminase," *BioChemical Pharmacology*, Vol. 45 (No. 9) pages 4857-1861, 1993.

U.S. Pat. No. 5,446,029 to Eriksson, et al., discloses that certain 2',3'-dideoxy-3'-fluoronucleosides have hepatitis B activity. U.S. Pat. No. 5,128,458 discloses certain 2',3'-dideoxy-4'-thioribonucleosides wherein the 3'-substituent is H, azide or fluoro. WO 94/14831 discloses certain 3'-fluoro-dihydropyrimidine nucleosides. WO 92/08727 discloses β-L-2'-deoxy-3'-fluoro-5-substituted uridine nucleosides for the treatment of herpes simplex 1 and 2.

EPA Publication No. 0 352 248 discloses a broad genus of L-ribofuranosyl purine nucleosides for the treatment of HIV, herpes, and hepatitis. While certain 2'-fluorinated purine nucleosides fall within the broad genus, there is no information given in the specification on how to make these compounds in the specification, and they are not among specifically disclosed or the preferred list of nucleosides in the specification. The specification does disclose how to make 3'-ribofuranosyl fluorinated nucleosides. A similar specification is found in WO 88/09001, filed by Aktiebolaget Astra.

European Patent Application 0 357 571 discloses a broad group of β-D and α-D pyrimidine nucleosides for the treatment of AIDS which among the broad class generically includes nucleosides that can be substituted in the 2' or 3'-position with a fluorine group. Among this broad class, however, there is no specific disclosure of 2'-fluorinated nucleosides or a method for their production.

EPA 0 463 470 discloses a process for the preparation of (5S)-3-fluoro-tetrahydro-5-[(hydroxy)methyl]-2-(3H)-furanone, a known intermediate in the manufacture of 2'-fluoro-2',3'-dideoxynucleosides such as 2'-fluoro-2',3'-dideoxycytidine.

U.S. Ser. No. 07/556,713 discloses β-D-2'-fluoroarabinofuranosyl nucleosides, and a method for their production, which are intermediates in the synthesis of 2',3'-dideoxy-2'-fluoroarabinosyl nucleosides.

U.S. Pat. No. 4,625,020 discloses a method of producing 1-halo-2-deoxy-2-fluoroarabinofuranosyl derivatives bearing protective ester groups from 1,3,5-tri-O-acyl-ribofuranose.

There appears to be a lack of disclosure of β-L-2'-fluoro-ribofuranosyl nucleosides for medicinal uses, including for HIV, hepatitis (B or C), or proliferative conditions. At least with respect to 2'-ribofuranosyl nucleosides, this may be because of the prior perceived difficulty in placing a fluoro group in the 2'-ribofuranosyl configuration. With respect to L-2'-fluoro-2',3'-unsaturated purine nucleosides, it may be because the purine nucleosides are unstable in acidic media, resulting in glycosyl bond cleavage.

In light of the fact that HIV acquired immune deficiency syndrome, AIDS-related complex, and hepatitis B and C viruses have reached epidemic levels worldwide, and have tragic effects on the infected patient, there remains a strong need to provide new effective pharmaceutical agents to treat these diseases that have low toxicity to the host. Further, there is a need to provide new antiproliferative agents.

Therefore, it is an object of the present invention to provide a method and composition for the treatment of human patients infected with hepatitis B or C.

It is another object of the present invention to provide a method and composition for the treatment of human patients infected with HIV.

It is a further object of the present invention to provide new antiproliferative agents.

It is still another object of the present invention to provide a new process for the preparation of 2'-fluoro-ribofuranosyl nucleosides.

It is yet another object of the present invention to provide a new process for the preparation of 2',3'-dideoxy-2',3'-didehydro-2'-fluoro-L-glycero-pent-2-eno-furanosyl nucleosides.

SUMMARY OF THE INVENTION

In one embodiment of the invention, a 2'-α-fluoro-nucleoside is provided of the structure:

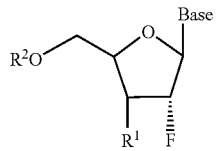

wherein

Base is a purine or pyrimidine base as defined further herein;

$R^1$ is OH, H, $OR^3$, $N_3$, CN, halogen, including F, or $CF_3$, lower alkyl, amino, loweralkylamino, di(lower)alkylamino, or alkoxy, and base refers to a purine or pyrimidine base;

$R^2$ is H, phosphate, including monophosphate, diphosphate, triphosphate, or a stabilized phosphate prodrug; acyl, or other pharmaceutically acceptable leaving group which when administered in vivo, is capable of providing a compound wherein $R^2$ is H or phosphate; sulfonate ester including alkyl or arylalkyl sulfonyl including methanesulfonyl, benzyl, wherein the phenyl group is optionally substituted with one or more substituents as described in the definition of aryl given above, a lipid, including a phospholipid, an amino acid, peptide, or cholesterol; and $R^3$ is acyl, alkyl, phosphate, or other pharmaceutically acceptable leaving group which when administered in vivo, is capable of being cleaved to the parent compound.

In a second embodiment, a 2'-fluoronucleoside is provided of the formula:

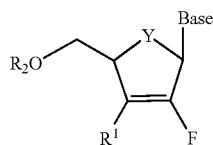

Y = O, S, $CH_2$, CHF wherein the substituents are as defined above.

In a third embodiment, a 2'-fluoronucleoside is provided of the formula:

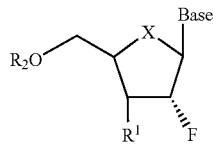

X = S, $CH_2$ wherein the substituents are as defined above.

In a fourth embodiment, a 2'-fluoronucleoside is provided of the structure:

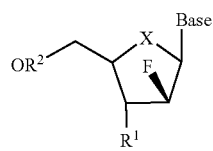

X = S, $CH_2$ wherein the substituents are as defined above.

These 2'-fluoronucleosides can be either in the β-L or β-D configuration. The β-L configuration is preferred.

The 2'-fluoronucleosides are biologically active molecules which are useful in the treatment of hepatitis B, hepatitis C or HIV. The compounds are also useful for the treatment of abnormal cellular proliferation, including tumors and cancer. One can easily determine the spectrum of activity by evaluating the compound in the assays described herein or with another confirmatory assay.

In another embodiment, for the treatment of hepatitis or HIV, the active compound or its derivative or salt can be administered in combination or alternation with another antiviral agent, such as an anti-HIV agent or anti-hepatitis agent, including those of the formula above. In general, in combination therapy, an effective dosage of two or more agents are administered together, whereas during alternation therapy, an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include 2-hydroxymethyl-5-(5-fluorocytosin-1-yl)-1,3-oxathiolane (FTC); the (−)-enantiomer of 2-hydroxymethyl-5(cytosin-1-yl)-1,3-oxathiolane (3TC); carbovir, acyclovir, interferon, famciclovir, penciclovir, AZT, DDI, DDC, D4T, abacavir, L-(−)-FMAU, L-DDA phosphate prodrugs, and β-D-dioxolane nucleosides such as β-D-dioxolanyl-guanine (DG), β-D-dioxolanyl-2,6-diaminopurine (DAPD), and β-D-dioxolanyl-6-chloropurine (ACP), non-nucleoside RT inhibitors such as nevirapine, MKC-442, DMP-266 (sustiva) and also protease inhibitors such as indinavir, saquinavir, AZT, DMP-450 and others.

The compounds can also be used to treat equine infectious anemia virus (EIAV), feline immunodeficiency virus, and simian immunodeficiency virus. (Wang, S., Montelaro, R., Schinazi, R. F., Jagerski, B., and Mellors, J. W.: "Activity of nucleoside and non-nucleoside reverse transcriptase inhibitors (NNRTI) against equine infectious anemia virus (EIAV)." *First National Conference on Human Retro viruses and Related Infections*, Washington, D.C., Dec. 12-16, 1993; Sellon D. C., "Equine Infectious Anemia," *Vet. Clin. North Am. Equine Pract. United States,* 9: 321-336, 1993; Philpott, M. S., Ebner, J. P., Hoover, E. A., "Evaluation of 9-(2-phosphonylmethoxyethyl)adenine therapy for feline immunodeficiency virus using a quantitative polymerase chain reaction," *Vet. Immunol. Immunopathol.* 35:155166, 1992.)

A new and completely diastereoselective method for the introduction of fluorine into a non-carbohydrate sugar ring precursor is also provided. The method includes reacting a chiral, non-carbohydrate sugar ring precursor (4S)-5-(protected oxy)-pentan-4-olide, which can be prepared from L-glutamic acid, with an electrophilic source of fluorine, including but not limited to N-fluoro-(bis)benzenesulfonimide, to yield key intermediate fluorolactone 6. The fluorolactone is reduced to the lactol and acetylated to give the anomeric acetate and then used for the synthesis of a number of novel β-L-α-2'-fluoronucleosides. The corresponding D-enantiomer can also be synthesized using D-glutamic acid as a starting material.

In an alternative embodiment, a fluorinated glycal is prepared which is dehydrogenated and then converted to a 2',3'-dideoxy-2',3'-didehydro-2'-fluoronucleoside or a β-L or β-D-arabinosyl-2'-fluoronucleoside, as discussed further below.

A method for the facile preparation of 2',3'-dideoxy-2',3'-didehydro-2'-fluoronucleosides is also presented that includes the direct condensation of silylated 6-chloropurine with key immediate, which is prepared from L-2,3-0-isopropylidene glyceraldenhyde.

DETAILED DESCRIPTION OF THE INVENTION

The invention as disclosed herein is a compound, method and composition for the treatment of HIV, hepatitis (B or C), or abnormal cellular proliferation, in humans or other host animals, that includes administering an effective amount of a 2'-fluoro-nucleoside, a pharmaceutically acceptable derivative, including a compound which has been alkylated or acylated at the 5'-position or on the purine or pyrimidine, or a pharmaceutically acceptable salt thereof, optionally in a pharmaceutically acceptable carrier. The compounds of this invention either possess antiviral (i.e., anti-HIV-1, anti-HIV-2, or anti-hepatitis (B or C)) activity, or antiproliferative activity, or are metabolized to a compound that exhibits such activity.

In summary, the present invention includes the following features:

(a) β-L and β-D-2'-fluoronucleosides, as described herein, and pharmaceutically acceptable derivatives and salts thereof;

(b) β-L and β-D-2'-fluoronucleosides as described herein, and pharmaceutically acceptable derivatives and salts thereof for use in medical therapy, for example for the treatment or prophylaxis of an HIV or hepatitis (B or C) infection or for the treatment of abnormal cellular proliferation;

(c) 2',3'-Dideoxy-2',3'-didehydro-2'-fluoro-L-glycero-pen-2-eno-furanosyl nucleosides, and pharmaceutically acceptable derivatives and salts thereof for use in medical therapy, for example for the treatment or prophylaxis of an HIV or hepatitis (B or C) infection or for the treatment of abnormal cellular proliferation (d) use of these 2'-fluoronucleosides, and pharmaceutically acceptable derivatives and salts thereof in the manufacture of a medicament for treatment of an HIV or hepatitis infection or for the treatment of abnormal cellular proliferation;

(e) pharmaceutical formulations comprising the 2'-fluoronucleosides or a pharmaceutically acceptable derivative or salt thereof together with a pharmaceutically acceptable carrier or diluent;

(f) processes for the preparation of β-L and β-D-2'-α-fluoronucleosides, as described in more detail below, and (g) proceseses for the preparation of 2',3'-dideoxy-2',3'-didehydro-2'-fluoro-L-glycero-pent-2-eno-furanosyl nucleosides.

I. Active Compound, and Physiologically Acceptable Derivatives and Salts Thereof A 2'-α-fluoro-nucleoside is provided of the structure:

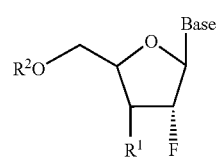

wherein $R^1$ is H, OH, $OR^3$, $N_3$, CN, halogen, including F, or $CF_3$, lower alkyl, amino, loweralkylamino, di(lower)alkylamino, or alkoxy, and base refers to a purine or pyrimidine base.

$R^2$ is H, phosphate, including monophosphate, diphosphate, triphosphate, or a stabilized phosphate prodrug; acyl, or other pharmaceutically acceptable leaving group which when administered in vivo, is capable of providing a compound wherein $R^2$ is H or phosphate, sulfonate ester including alkyl or arylalkyl sulfonyl including methanesulfonyl, benzyl, wherein the phenyl group is optionally substituted with one or more substituents as described in the definition of aryl given above, a lipid, an amino acid, peptide, or cholesterol; and $R^3$ is acyl, alkyl, phosphate, or other pharmaceutically acceptable leaving group which when administered in vivo, is capable of being cleaved to the parent compound.

In a second embodiment, a 2-fluoronucleoside is provided of the formula:

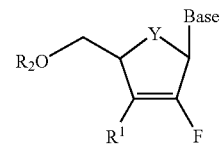

$Y = O, S, CH_2, CHF$

In a third embodiment, a 2-fluoronucleoside is provided of the formula:

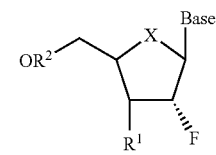

$X = S, CH_2$

In a fourth embodiment, a 2-fluoronucleoside is provided of the structure:

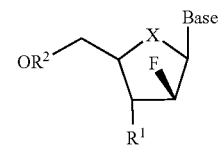

$X = S, CH_2$

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl,2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

The active compound can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and a compound which has been alkylated or acylated at the 5'-position or on the purine or pyrimidine base (alternatively referred to as "pharmaceutically acceptable derivatives"). Further, the modifications can affect the biological activity of the compound, in some cases increasing the activity over the parent compound. This can easily be assessed by preparing the derivative and testing its antiviral activity according to the methods described herein, or other method known to those skilled in the art.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

As used herein, the term "substantially free of" or "substantially in the absence of" refers to a nucleoside composition that includes at least 95% to 98%, or more preferably, 99% to 100%, of the designated enantiomer of that nucleoside.

Nucleotide Prodrug Formulations

Any of the nucleosides described herein can be administrated as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses*. 6:491-0.501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hostetler, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No.

5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and muse." *Cancer Res.* 33, 2816-2820; Holy, A. (1993) Isopolar phosphorous-modified nucleotide analogues," In: De Clercq (Ed.), *Advances in Antiviral Drug Design*, Vol. I, JAI Press, pp. 179-231; Hong, C. I., Nechaev, A., and West, C. R. (1979a) "Synthesis and antitumor activity of 1-β-D-arabino-furanosylcytosine conjugates of cortisol and cortisone." *Bicohem. Biophys. Rs. Commun.* 88, 1223-1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl) cytosine conjugates of corticosteriods and selected lipophilic alcohols." *J. Med. Chem.* 28, 171-177; Hosteller, K. Y., Stuhmiller, L. M., Lenting, H. B. M. van den Bosch, H. and Richman *J. Biol. Chem* 265, 6112-6117; Hosteller, K. Y., Carson, D. A. and Richman, D. D. (1991); "Phosphatidylazidothymidine: mechanism of antiretroviral action in CEM cells." *J. Biol. Chem.* 266, 11714-11717; Hosteller, K. Y., Korba, B. Sridhar, C., Gardener, M. (1994a) "Antiviral activity of phosphatidyl-dideoxycytidine in hepatitis B-infected cells and enhanced hepatic uptake in mice." *Antiviral Res.* 24, 59-67; Hosteller, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidyl-ddc: Assessment of uptake in mouse lymphoid tissues and antiviral activities in human immunodeficiency virus-infected cells and in rauscher leukemia virus-infected mice." *Antimicrobial Agents Chemother.* 38, 2792-2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-flourouridine." *J. Med. Chem.* 27, 440-444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." *J. Med. Chem.* 33 2264-2270; Jones, A. S., McGuigan, C., Walker, R. T., Balzarini, J. and DeClercq, E. (1984) "Synthesis, properties, and biological activity of some nucleoside cyclic phosphoramidates." *J. Med. Chem. Soc. Perkin Trans. I,* 1471-1474; Juodka, B. A. and Smrt, J. (1974) "Synthesis of diribonucleoside phosph (P→N) amino acid derivatives." *Coll. Czech. Chem. Comm.* 39, 363-968; Kataoka, S., Imai, J., Yamaji, N., Kato, M., Saito, M., Kawada, T. and Imai, S. (1989) "Alkylated cAMP derivatives; selective synthesis and biological activities." *Nucleic Acids Res. Sym. Ser.* 21, 1-2; Kataoka, S., Uchida, "(cAMP) benzyl and methyl triesters." *Heterocycles* 32, 1351-1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate an dphosphorodiamidate derivates against HIV and ULV in vitro." *Antiviral Chem. Chemother.* 3, 107-112; Kodama, K., Morozumi, M., Saithoh, K. I., Kuninaka, H., Yosino, H. and Saneyoshi, M. (1989) "Antitumor activity and pharmacology of 1-β-D-arabinofuranosylcytosine-5'-stearylphosphate; an orally active derivative of 1-β-D-arabinofuranosylcytosine." *Jpn. J. Cancer Res.* 80, 679-685; Korty, M. and Engels, J. (1979) "The effects of adenosine- and guanosine 3',5' phosphoric and acid benzyl esters on guinea-pig ventricular myocardium." *Naunyn-Schmiedeberg's Arch. Pharmacol.* 310, 103-111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." *J. Med. Chem,* 33, 2368-2375; LeBec, C., and Huynh-Dinh, T. (1991) "Synthesis of lipophilic phosphate triester derivatives of 5-fluorouridine an arabinocytidine as anticancer prodrugs." *Tetrahedron Lett.* 32, 6553-6556; Lichtenstein, J., Barner, H. D. and Cohen, S. S. (1960) "The metabolism of exogenously supplied nucleotides by *Escherichia coli,*" *J. Biol. Chem.* 235, 457-465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". *Mitt. Geg. Lebensmittelunters. Hyg.* 72, 131-133 (*Chem. Abstr.* 95, 127093); McGigan, C. Tollerfield, S. M. and Riley, P. a. (1989) "Synthesis and biological evaluation of some phosphate triester derivatives of the anti-viral drug Ara." *Nucleic Acids Res.* 17, 6065-6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." *Antiviral Chem. Chemother.* 1107-113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddCyd." *Antiviral Chem. Chemother.* 1, 355-360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." *Antiviral Chem. Chemother.* 1, 25-33; McGuigan, C., Devin, K. G., O'Connor, T. J., and Kinchington, D. (1991) "Synthesis and anti-HIV activity of some haloalkyl phosphoramidate derivatives of 3'-azido-3'-deoxythylmidine (AZT); potent activity of the trichloroethyl methoxyalaninyl compound." *Antiviral Res.* 15, 255-263; McGuigan, C., Pathirana, R. N., Balzarini, J. and DeClercq, E. (1993b) "Intracellular delivery of bioactive AZT nucleotides by aryl phosphate derivatives of AZT." *J. Med. Chem.* 36, 1048-1052.

Alkyl hydrogen phosphate derivatives of the anti-HIV agent AZT may be less toxic than the parent nucleoside analogue. *Antiviral Chem. Chemother.* 5, 271-277; Meyer, R. B., Jr., Shuman, D. A. and Robins, R. K. (1973) "Synthesis of purine nucleoside 3',5'-cyclic phosphoramidates." *Tetrahedron Lett.* 269-272; Nagyvary, J. Gohil, R. N., Kirchner, C. R. and Stevens, J. D. (1973) "Studies on neutral esters of cyclic AMP," *Biochem. Biophys. Res. Commun.* 55, 1072-1077; Namane, A. Gouyette, C., Fillion, M. P., Fillion, G. and Huynh-Dinh, T. (1992) "Improved brain delivery of AZT using a glycosyl phosphotriester prodrug." *J. Med. Chem.* 35, 3039-3044; Nargeot, J. Nerbonne, J. M. Engels, J. and Leser, H. A. (1983) *Natl. Acad. Sci. U.S.A.* 80, 2395-2399; Nelson, K. A., Bentrude, W. G. Stser, W. N. and Hutchinson, J. P. (1987) "The question of chair-twist equilibria for the phosphate rings of nucleoside cyclic 3',5' monophosphates." $^1$HNMR and x-ray crystallographic study of the diastereomers of thymidine phenyl cyclic 3',5'-monophosphate." *J. Am. Chem. Soc.* 109, 4058-4064; Nerbonne, J. M., Richard, S., Nargeot, J. and Lester, H. A. (1984) "New photoactivatable cyclic nucleotides produce intracellular jumps in cyclic AMP and cyclic GMP concentrations." *Nature* 301, 74-76; Neumann, J. M., Herv_, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." *J. Am. Chem. Soc.* 111, 4270-4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (1991) "Treatment of myelodysplastic syndromes with orally administered 1-β-D-arabinouranosylcytosine-5' stearylphosphate." *Oncology* 48, 451-455. Palomino, E., Kessle, D. and Horwitz, J. P. (1989) "A dihydropyridine carrier system for sustained delivery of 2', 3' dideoxynucleosides to the brain." *J. Med. Chem.* 32, 22-625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRL47923 and its oral prodrug, SB203657A against a rauscher murine leukemia virus infection in mice." *Antiviral Res.* 20 (Suppl. I). 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." *J. Med. Chem.* 34, 1408-1414; Pompon, A., Lefebvre, I., Imbach, J. L., Kahn, S. and Farquhar, D. (1994). "Decomposition pathways of the mono- and bis(pivaloyloxymethyl) esters of azidothymidine-5'-monophosphate in cell extract and in tissue culture medium; an application of the 'on-line ISRP-cleaning HPLC technique." *Antiviral Chem Chemother.* 5, 91-98; Postemark, T. (1974) "Cyclic AMP and cyclic GMP." *Annu. Rev. Pharmacol.* 14, 23-33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1, 3-dihydroxy-2-propoxy)methyl]guanine." *J. Med. Chem.* 29, 671-675; Pucch, F., Gosselin, G., Lefebvre, I., Pompon, a., Aubertin, A. M. Dirn, and Imbach, J. L. (1993) "Intracellular delivery of nucleoside monophosphate through a reductase-mediated activation process." *Antivral Res.* 22, 155-174; Pugaeva, V. P., Klochkeva, S. I., Mashbits, F. D. and Eizengart, R. S. (1969). "Toxicological assessment and health standard ratings for ethylene sulfide in the industrial atmosphere." *Gig. Trf. Prof. Zabol.* 14, 47-48 (*Chem. Abstr.* 72, 212); Robins, R. K. (1984) "The potential of nucleotide analogs as inhibitors of Retro viruses and tumors." *Pharm. Res.* 11-18; Rosowsky, A., Kim. S. H., Ross and J. Wick, M. M. (1982) "Lipophilic 5'-(alkylphosphate)esters of 1-β-D-arabinofuranosylcytosine and its N[4]-acyl and 2.2'-anhydro-3'0-acyl derivatives as potential prodrugs." *J. Med. Chem.* 25, 171-178; Ross, W. (1961) "Increased sensitivity of the walker turnout towards aromatic nitrogen mustards carrying basic side chains following glucose pretreatment." *Biochem. Pharm.* 8, 235-240; Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-β-D-arabinofuranosylcytosine 5' diphosphate [31], 2-diacylglycerols." *J. Med. Chem.* 25, 1322-1329; Saffhill, R. and Hume, W. J. (1986) "The degradation of 5-iododeoxyuridine and 5-bromoethoxyuridine by serum from different sources and its consequences for the use of these compounds for incorporation into DNA." *Chem. Biol. Interact.* 57, 347-355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabinofuranosylcytosine 5'-alky or arylphosphates." *Chem Pharm. Bull.* 28, 2915-2923; Sastry, J. K., Nehete, P. N., Khan, S., Nowak, B. J., Plunkett, W., Arlinghaus, R. B. and Farquhar, D. (1992) "Membrane-permeable dideoxyuridine 5'-monophosphate analogue inhibits human immunodeficiency virus infection." *Mol. Pharmacol.* 41, 441-445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." *9th Annual AAPS Meeting.* San Diego, Calif. (Abstract). Shuto, S., Ueda, S., Imamura, S., Fukukawa, K. Matsuda, A. and Ueda, T. (1987) "A facile one-step synthesis of 5' phosphatidylnucleosides by an enzymatic two-phase reaction." *Tetrahedron Lett.* 28, 199-202; Shuto, S. Itoh, H., Ueda, S., Imamura, S., Kukukawa, K., Tsujino, M., Matsuda, A. and Ueda, T. (1988) *Pharm. Bull.* 36, 209-217. An example of a useful phosphate prodrug group is the S-acyl-2-thioethyl group, also referred to as "SATE".

II. Combination and Alternation Therapy

It has been recognized that drug-resistant variants of HIV and HBV can emerge after prolonged treatment with an antiviral agent. Drug resistance most typically occurs by mutation of a gene that encodes for an enzyme used in viral replication, and most typically in the case of HIV, reverse transcriptase, protease, or DNA polymerase, and in the case of HBV, DNA polymerase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a reverse transcriptase inhibitor (a "RTI"), which can be either a synthetic nucleoside (a "NTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor A list compiling resistance data collected in vitro and in vivo for a number of antiviral compounds is found in Schinazi, et al, Mutations in retroviral genes associated with drug resistance, *International Antiviral News,* 1997.

Preferred compounds for combination or alternation therapy for the treatment of HBV include 3TC, FTC, L-FMAU, interferon, β-D-dioxolanyl-guanine (DXG), β-D-dioxolanyl-2,6-diaminopurine (DAPD), and β-D-dioxolanyl-6-chloropurine (ACP), famciclovir, penciclovir, BMS-200475, bis pom PMEA (adefovir, dipivoxil); lobucavir, ganciclovir, and ribavarin.

Preferred examples of antiviral agents that can be used in combination or alternation with the compounds disclosed herein for HIV therapy include cis-2-hydroxymethyl-5-(5- fluorocytosin-1-yl)-1,3-oxathiolane (FTC); the (−)-enantiomer of 2-hydroxymethyl-5-(cytosin-1-yl)-1,3-oxathiolane (3TC); carbovir, acyclovir, foscarnet, interferon, AZT, DDI, DDC, D4T, CS-87 (3'-azido-2',3'-dideoxy-uridine), and β-D-dioxolane nucleosides such β-D-dioxolanyl-guanine (DXG), β-D-dioxolanyl-2,6-diaminopurine (DAPD), and β-D-dioxolanyl-6-chloropurine (ACP), MKC-442 (6-benzyl-1-(ethoxymethyl)-5-isopropyl uracil.

Preferred protease inhibitors include crixivan (Merck), nelfinavir (Agouron), ritonavir (Abbott), saquinavir (Roche), DMP-266 (Sustiva) and DMP-450 (DuPont Merck).

A more comprehensive list of compounds that can be administered in combination or alternation with any of the disclosed nucleosides include (1S,4R)-4-[2-amino-6-cyclopropyl-amino)-9H-purin-9-yl]-2-cyclopentene-1-methanol succinate ("1592", a carbovir analog; GlaxoWellcome); 3TC: (−)-β-L-2',3'-dideoxy-3'-thiacytidine (GlaxoWellcome); a-APA R18893: a-nitro-anilino-phenylacetamide; A-77003; C2 symmetry-based protease inhibitor (Abbott); A-75925: C2 symmetry-based protease inhibitor (Abbott); AAP-BHAP: bisheteroarylpiperazine analog (Upjohn); ABT-538: C2 symmetry-based protease inhibitor (Abbott); AzddU: 3'-azido-2',3'-dideoxyuridine; AZT: 3'-azido-3'-deoxythymidine (GlaxoWellcome); AZT-p-ddI: 3'-azido-3'-deoxythymidilyl-(5',5')-2',3'-dideoxyinosinic acid (Ivax); BHAP: bisheteroarylpiperazine; BILA 1906: N-{1S-[[[3-[2S-{(1,1-dimethylethyl)amino]carbonyl}-4R-]3-pyridinylmethyl)thio]-1-piperidinyl]-2R-hydroxy-1S-(phenylmethyl) propyl]amino]carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethyphenoxy)-1-oxoethyl]amino]-2R-hydroxy-4-phenylbutyl] 4R-pyridinylthio)-2-piperidine-carboxamide (BioMega/Boehringer-Ingelheim); BM+51.0836: thiazolo-isoindolinone derivative; BMS 186,318: aminodiol derivative HIV-1 protease inhibitor (Bristol-Myers-Squibb); d4API: 9-[2,5-dihydro-5-(phosphonomethoxy)-2-furanel] adenine (Gilead); d4C: 2',3'-didehydro-2',3,-dideoxycytidine; d4T: 2',3'-didehydro-3'-deoxythymidine (Bristol-Myers-Squibb); ddC; 2',3'-dideoxycytidine (Roche); ddI: 2',3'-dideoxyinosine (Bristol-Myers-Squibb); DMP-266: a 1,4-dihydro-2H-3,1-benzoxazin-2-one; DMP-450: {[4R-(4-a,5-a,6-b,7-b)]-hexahydro-5,6-bis(hydroxy)-1,3-bis(3-amino) phenyl]methyl)-4,7-bis(phenylmethyl)-2H-1,3-diazepin-2-one}-bismesylate (Avid); DXG: (−)-β-D-dioxolane-guanosine (Triangle); EBU-dM: 5-ethyl-1-ethoxymethyl-6-(3,5-dimethylbenzyl)uracil; E-EBU: 5-ethyl-1-ethoxymethyl-6-benzyluracil; DS: dextran sulfate; E-EPSeU: 1-(ethoxymethyl)-(6-phenylselenyl)-5-ethyluracil; E-EPU: 1-(ethoxymethyl)-(6-phenyl-thio)-5-ethyluracil; FTC: β-2',3'-dideoxy-5-fluoro-3'-thiacytidine (Triangle); HBY097: S-4-isopropoxycarbonyl-6-methoxy-3-(methylthio-methyl)-3,4-dihydroquinoxalin-2(1H)-thione; HEPT: 1-[(2-hydroxyethoxy)methyl]-6-(phenylthio)thymine; HIV-1: human immunodeficiency virus type 1; JM2763: 1,1'-(1,3-propanediyl)-bis-1,4,8,11-tetraazacyclotetradecane (Johnson Matthey); JM3100: 1,1'-[1,4-phenylenebis-(methylene)]-bis-1,4,8,11-tetraazacyclotetradecane (Johnson Matthey); KNI-272: (2S,3S)-3-amino-2-hydroxy-4-phenylbutyric acid-containing tripeptide; L-697,593; 5-ethyl-6-methyl-3-(2-phthalimido-ethyl)pyridin-2(1H)-one; L-735, 524: hydroxy-aminopentane amide HIV-1 protease inhibitor (Merck); L-697,661: 3-{[(4,7-dichloro-1,3-benzoxazol-2-yl)methyl]amino}-5-ethyl-6-methylpyridin-2(1H)-one; L-FDDC: (−)-β-L-5-fluoro-2',3'-dideoxycytidine; L-FDOC: (−)-β-L-5-fluoro-dioxolane cytosine; MKC442: 6-benzyl-1-ethoxymethyl-5-isopropyluracil (1-EBU; Triangle/Mitsubishi); Nevirapine: 11-cyclopropyl-5,11-dihydro-4-methyl-6H-dipyridol[3,2-b:2',3'-e]diazepin-6-one (Boehringer-Ingelheim); NSC648400: 1-benzyloxymethyl-5-ethyl-6-(alpha-pyridylthio)uracil (E-BPTU); P9941: [2-pyridylacetyl-IlePheAla-y(CHOH)]2 (Dupont Merck); PFA: phosphonoformate (foscarnet; Astra); PMEA: 9-(2-phosphonylmethoxyethyl)adenine (Gilead); PMPA: (R)-9-(2-phosphonyl-methoxypropyl)adenine (Gilead); Ro 31-8959: hydroxyethylamine derivative HIV-1 protease inhibitor (Roche); RPI-312: peptidyl protease inhibitor, 1-[(3s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3,4-dihydro-quinoxalin-2(1H)thione; SC-52151: hydroxyethylurea isostere protease inhibitor (Searle); SC-55389A: hydroxyethyl-urea isostere protease inhibitor (Searle); TIBO R821550: (+)-(5S)-4,5,6,7-tetrahydro-5-methyl-6-(3-methyl-2-butenyl)imidazo[4,5,1-jk][1,4]-benzodiazepin-2(1H)-thione (Janssen); TIBO 82913: (+)-(5S)-4, 556,7,-tetrahydro-9-chloro-5-methyl-6-(3-methyl-2-butenyl)imidazo[4,5,1jk]-[1,4]benzodiazepin-2(1H)-thione (Janssen); TSAO-m3T: [2',5'-bis-O-(tert-butyldimethylsilyl)-3'-spiro-5'-(4'-amino-1',2'-oxathiole-2',2'-dioxide)]-b-D-pentofuranosyl-N3-methylthymine; U90152:1-[3-[(1-methylethyl)-amino]-2-pyridinyl]-4-[[5-[(methylsulphonyl)-amino]-1H-indol-2yl]carbonyl]-piperazine; UC: thiocarboxanilide derivatives (Uniroyal); UC-781=N-[4-chloro-3-(3-methyl-2-butenyloxy)phenyl]-2-methyl-3-furancarbothioamide; UC-82=N-[4-chloro-3-(3-methyl-2-butenyloxy)phenyl]-2-methyl-3-thiophenecarbothioamide; VB 11,328: hydroxyethylsulphonamide protease inhibitor (Vertex); VX-478: hydroxyethylsulphonamide protease inhibitor (Vertex); XM 323: cyclic urea protease inhibitor (Dupont Merck).

Combination Therapy for the Treatment of Proliferative Conditions

In another embodiment, the compounds, when used as an antiproliferative, can be administered in combination with another compound that increases the effectiveness of the therapy, including but not limited to an antifolate, a 5-fluoropyrimidine (including 5-fluorouracil), a cytidine analogue such as β-L-1,3-dioxalanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifofamide, mechlorethamine, melphalan, and thiotepa), nonclassical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. The compounds of the present invention can also be used in combination with enzyme therapy agents and immune system modulators such as an interferon, interleukin, tumor necrosis factor, macrophage colony-stimulating factor and colony stimulating factor.

III. Process for the Preparation of Active Compounds

In one embodiment of the invention, a diastereoselective reaction for effecting the introduction of fluorine into the sugar portion of novel nucleoside analogs is provided. This synthesis can be used to make both purine and pyrimidine derivatives. The key step in the synthetic route is the fluorination of a chiral, non-carbohydrate sugar ring precursor (4S)-5-(protected-oxy)-pentan-4-olide, for example, (4S)-5-(t-butyldiphenylsiloxy)-pentan-4-olide 4 using an electrophilic fluorine source, including, but not limited to, N-fluoro-(bis)benzenesulfonimide 5. This relatively new class of N-fluorosulfonimide reagents was originally developed by Barnette in 1984 and since then has seen much refinement and use as a convenient and highly reactive source of electrophilic fluorine (Barnette, W. E. *J. Am. Chem. Soc.* 1984, 106, 452.; Davis, F. A.; Han; W., Murphy, C. K. *J. Org. Chem.* 1995, 60, 4730; Snieckus, V.; Beaulieu, F.; Mohri, K.; Han, W.; Murphy, C. K.; Davis, F. A. *Tetrahedron Lett.* 1994, 35(21), 3465). Most often, these reagents are used to deliver fluorine to nucleophiles such as enolates and metalated aromatics (Davis, F. A.; Han; W., Murphy, C. K. *J. Org. Chem.* 1995, 60, 4730). Specifically, N-fluoro-(bis)benzenesulfonimide (NFSi) is an air stable, easily handled solid with sufficient steric bulk to stereoselectively fluorinate the enolate of silyl-protected lactone 4. As a nonlimiting example of this process, the synthesis of fluorolactone 6 and its use as a common intermediate in the synthesis of a number of novel α-2'-fluoro nucleosides is described in detail below. Given this description, one of ordinary skill can routinely modify the process as desired to accomplish a desired objective and to prepare a compound of interest.

Any source of electrophilic fluorine can be used that fluorinates the precursor (4S)-5-(protected-oxy)-pentan-4-olide, for example, (4S)-5-(t-butyldiphenylsiloxy)-pentan-4-olide. Alternative sources of electrophilic fluorine include N-fluorosulfams (Differding, et al, *Tet. Lett.* Vol. 29, No. 47 pp 6087-6090 (1988); *Chemical Reviews,* 1992, Vol 92, No. 4 (517)), N-fluoro-O-benzenedisulfonimide (*Tet. Lett.* Vol. 35, pages 3456-3468 (1994), *Tet. Lett.* Vol 35. No. 20, pages 3263-3266 (1994)); *J. Org. Chem.* 1995, 60, 4730-4737), 1-fluoroethene and synthetic equivalents (Matthews, *Tet. Lett.* Vol. 35, No. 7, pages 1027-1030 (1994); Accufluor fluorinating agents sold by Allied Signal, Inc., Buffalo Research Laboratory, Buffalo, N.Y. (NFTh(1-fluoro-4-hydroxy-1,4-diazoa-bicyclo[2.2.2]octane bis(tetrarluoroborate)), NFPy (N-fluoropyridinium pyridine heptafluorodiborate), and NFSi (N-fluorobenzenesulfonimide); electrophilic fluorinating reagents sold by Aldrich Chemical Company, Inc., including N-fluoropyridinium salts ((1-fluoro-2,4,6-trimethylpyridinium triflate, 3,5-dichloro-1-fluoropyridinium triflate, 1-fluoropyridinium triflate, 1-fluoropyridinium tetrafluoroborate, and 1-fluoropyridinium pyridine heptafluorodiborate) see also *J. Am. Chem. Soc.*, Vol 112, No. 23 1990); N-fluorosulfonimides and-amides (N-fluoro-N-methyl-p-toluenesulfonamide, N-fluoro-N-propyl-p-toluenesulfonamide, and N-fluorobenzenesulfonimide); N-fluoro-quinuclidinium fluoride (*J. Chem. Soc. Perkin Trans I* 1988, 2805-2811); perfluoro-2,3,4,5-tetrahydropyridine and perfluoro-(1-methylpyrrolidine), Banks, Cheng, and Haszeldine, *Heterocyclic Polyfluoro-Compounds Part II* (1964); 1-fluoro-2-pyridone, *J. Org. Chem.,* 1983 48, 761-762; quaternary stereogenic centers possessing a fluorine atom (*J. Chem. Soc. Perkin Trans.* pages 221-227 (1992));
N-fluoro-2,4,6-pyridinium triflate, Shimizu, *Tetrahedron* Vol 50(2), pages 487-495 (1994); N-fluoropyridinium pyridine heptafluorodiborate, *J. Org. Chem.* 1991, 56, 5962-5964; Umemoto, et al., *Bull. Chem. Soc. Jpn.,* 64 1081-1092 (1991); N-fluoroperfluoroalkylsulfonimides, *J. Am. Chem. Soc.,* 1987, 109, 7194-7196; Purrington, et al., Lewis Acid Mediated Fluorinations of Aromatic Substrates, *J. Org. Chem.* 1991, 56, 142-145.

A significant advantage of this methodology is the ability to access separately either the "natural" (1a) D or the "unnatural" (1b) L enantiomer of the nucleosides by appropriate choice of L- or D-glutamic acid starting material, respectively.

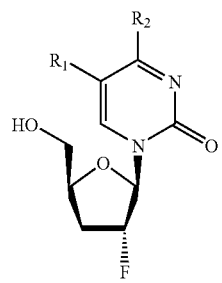

1a

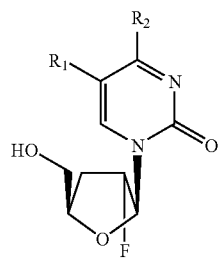

1b $R_1$ = H, $CH_3$, F
$R_2$ = OH, $NH_2$, NHAc

Lactone 4 was synthesized by the route shown in Scheme 1 from L-glutamic acid as described by Ravid et al. (*Tetrahedron* 1978, 34, 1449) and Taniguchi et al. (*Tetrahedron* 1974, 30, 3547).

Scheme 1

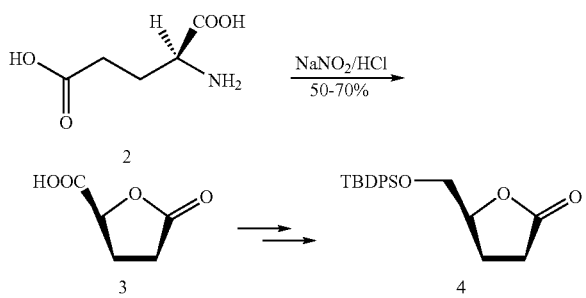

The enolate of lactone 4, prepared at −78° C. with LiHMDS in THF, is known to be stable. Several syntheses using this enolate have been performed, including addition of electrophiles such as diphenyldiselenide, diphenyldisulfide, and alkyl halides in high yield (Liotta, D. C.; Wilson, L. J. *Tetrahedron Lett.* 1990, 31(13), 1815; Chu, C. K.; Babu, J. R.; Beach, J. W.; Ahn, S. K.; Huang, H.; Jeong, L. S.; Lee, S. J. *J. Org. Chem.,* 1990, 55, 1418; Kawakami, H.;

Ebata, T.; Koseki, K.; Matsushita, H.; Naoi, Y.; Itoh, K. *Chem. Lett.* 1990, 1459). However, addition of a THF solution of 5 to the enolate of 4 gave poor yields of the desired monofluorinated product 6. Numerous by-products were formed including what was surmised to be a difluorinated lactone that is inseparable from other impurities. For this reason, the order of addition of the reagents was altered such that lactone 4 and NFSi 5 were dissolved together in THF and cooled to −78° C. Slow addition of LiHMDS resulted in a reaction yielding 6 as the only product in addition to a small amount of unreacted starting material (eq 1).

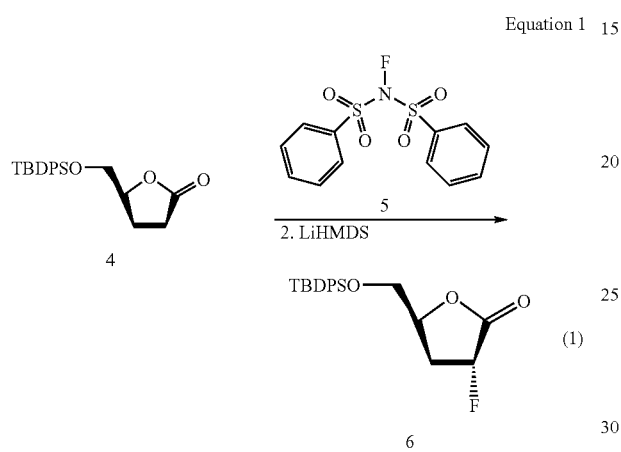

Equation 1

Fluorolactone 6 could be obtained in 50-70% yield after silica gel column chromatography and crystallization. This reaction yielded a single diastereomer of 6, presumably due to the interaction of the sterically bulky TBDPS group and the bulky fluorinating reagent 5. Identification of fluorolactone 6 as the α or "down" fluoro isomer was accomplished by comparison to previously published NMR data and by X-ray crystal structure determination of its enantiomer 20.

Lactone 6 was transformed into the anomeric acetate 8 as shown in Scheme 2. It is of interest to note that lactol 7 exists exclusively as the β anomer and that acetate 8 shows no detectable α anomer by NMR, as reported by Niihata et al. (*Bull. Chem. Soc. Jpn.* 1995, 68, 1509).

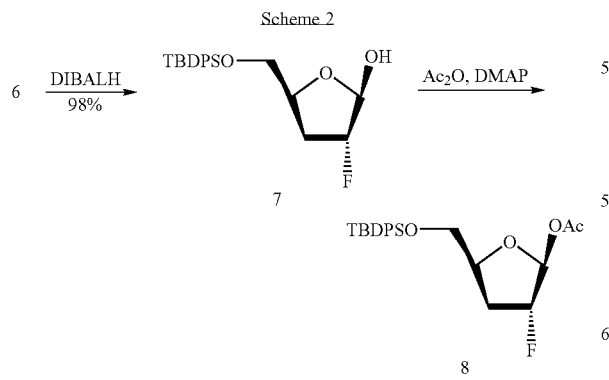

Scheme 2

Coupling of 8 with silylated pyrimidine bases was performed by standard Vorbruggen methodology (*Tetrahedron Lett.* 1978, 15, 1339) using TMS triflate as the Lewis acid. Alternatively, any other Lewis acid known to be useful to condense a base with a carbohydrate to form a nucleoside can be used, including tin chloride, titanium chloride, and other tin or titanium compounds. A number of bases were successfully coupled in high yields ranging from 72%-100% after column chromatography (eq 2, Table 1).

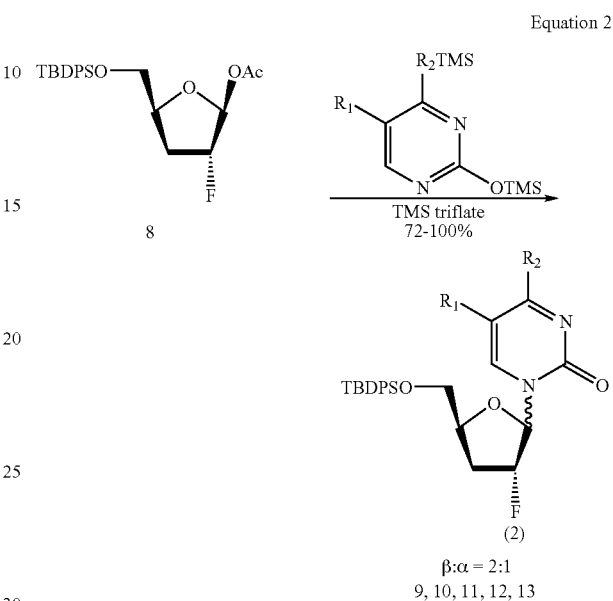

Equation 2

β:α = 2:1
9, 10, 11, 12, 13

TABLE 1

Glycosylation of Substituted Pyrimidines with 8

| Cmpd. | $R_1$ | $R_2$ | yield |
|---|---|---|---|
| 9 | F | OH | 87% |
| 10 | F | $NH_2$ | 99% |
| 11 | H | NHAc | 91% |
| 12 | H | $NH_2$ | 72% |
| 13 | $CH_3$ | OH | 89% |

Proton NMR indicated that the ratio of β to α nucleoside anomers was approximately 2:1 in all cases. The silyl protected nucleosides could not be resolved by column chromatography into the separate anomers. However, after deprotection of the 5'-oxygen with $NH_4F$ in methanol (eq 3), the α and β anomers could be readily separated and the results are summarized in Table 2.

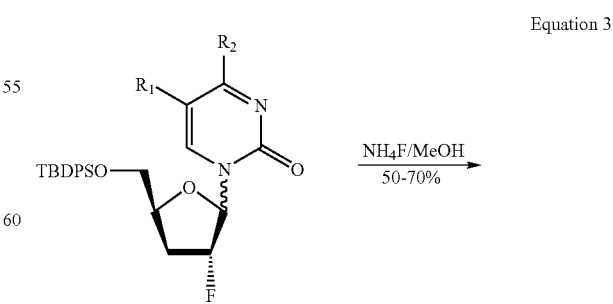

Equation 3

β:α = 2:1
9, 10, 11, 12, 13

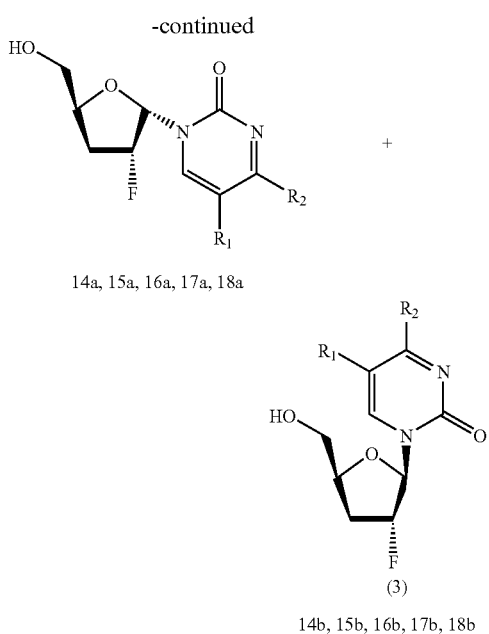

14a, 15a, 16a, 17a, 18a 14b, 15b, 16b, 17b, 18b (3)

TABLE 2

Deprotection of Nucleosides

| $R_1$ | $R_2$ | a | yield | b | yield |
|---|---|---|---|---|---|
| F | OH | 14a | 19% | 14b | 48% |
| F | $NH_2$ | 15a | 27% | 15b | 51% |
| H | NHAc | 16a | 17% | 16b | 31% |
| H | $NH_2$ | 17a | — | 17b | — |
| $CH_3$ | OH | 18a | 12% | 18b | 33% |

The classification of the free nucleosides as α or β was based on the chemical shift of the anomeric proton (Table 3) and on the polarity of the nucleosides as observed by thin layer chromatography. A trend for all of the α/β pairs of free nucleosides was observed in that the less polar compound of the two had an anomeric proton chemical shift that was notably upfield from that of the more polar compound.

TABLE 3

Anomeric Proton Chemical Shift (ppm)

| Cmpd. | α | β |
|---|---|---|
| 14 a, b | 6.11 | 5.89 |
| 15 a, b | 6.08 | 5.92 |
| 16 a, b | 6.09 | 5.90 |
| 17 a, b | 6.05 | 5.92 |
| 18 a, b | 6.11 | 5.93 |

The correlation between anomeric proton chemical shift and absolute structure was verified by comparison of 18a (Niihata, S.; Ebata, T.; Kawakami, H.; Matsushida, H. *Bull. Chem. Soc. Jpn.* 1995, 68, 1509) and 18b (Aerschot, A. V.; Herdewijn, P.; Balzarini, J.; Pauwels, R.; De Clercq, E. *J. Med. Chem.* 1989, 32, 1743) with previously published spectral data and through X-ray crystal structure determination of 14b and 15b. This finding is the opposite of the usual trend for nucleosides in which the α anomer is normally the less polar of the two. Presumably, in the "down" 2'-fluorinated nucleosides, the strong dipole of the C—F bond opposes the C—N anomeric bond dipole in the β isomer and reduces the overall molecular dipole. Conversely, the α anomer has a geometry that allows reinforcement of the molecular dipole through the addition of the C—F and C—N bond dipoles. Thus, the a anomer is more polar than the β anomer in the case of α-2'-fluoro nucleosides.

The α and β anomers 17a and 17b could not be separated by column chromatography because the free amino group caused the nucleosides to streak on silica gel. Therefore, it was necessary to use $N^4$-acetylcytosine to prepare 11 and then resolve 16a and 16b. The $N^4$-acetyl group was removed quantitatively with a saturated solution of ammonia in methanol in order to obtain separated 17a and 17b. When 5-fluorocytosine was used as the base (compound 10), the anomers 15a and 15b were easily separated and no streaking on silica gel was observed.

Of the ten nucleosides listed in Table 2, it appears that only 17b (Martin, J. A.; Bushnell, D. J.; Duncan, I. B.; Dunsdon, S. J.; Hall, M. J.; Machin, P. J.; Merrett, J. H.; Parkes, K. E. B.; Roberts, N. A.; Thomas, G. J.; Galpin, S. A.; Kinchington, D. *J. Med. Chem.* 1990, 33(8), 2137; Zenchoff, G. B.; Sun, R.; Okabe, M. *J. Org. Chem.* 1991, 56, 4392), 18a (Niihata, S.; Ebata, T.; Kawakami, H.; Matsushida, H. *Bull. Chem. Soc. Jpn.* 1995, 68, 1509), and 18b (Aerschot, A. V.; Herdewijn, P.; Balzarini, J.; Pauwels, R.; De Clercq, E. *J. Med. Chem.* 1989, 32, 1743) have been synthesized previously. They, like the numerous known 2'-β or "up" fluoro nucleoside analogs[14] have been synthesized from natural precursors (i.e., they are in the β-D configuration). It appears that no β-L-2'-fluoro-ribofuranosyl nucleosides have been identified in the literature prior to this invention.

Fluorine is usually introduced into these molecules through nucleophilic attack on an anhydro-nucleoside (Mengel, R.; Guschlbauer, W. *Angew. Chem., Int. Ed. Engl.* 1978, 17, 525) or through replacement and inversion of a stereochemically fixed hydroxyl group with diethylaminosulfur trifluoride (DAST) (Herdewijn, P.; Aerschot, A. V.; Kerremans, L. *Nucleosides Nucleotides* 1989, 8(1), 65). One advantage of the present methodology is that no hydroxyl group is needed for fluorine introduction. Thus, the process is not limited to natural nucleosides or sugars as starting materials, and provides an easy to access the unnatural enantiomers of the 2'-fluoro nucleosides.

Accordingly, several unnatural nucleosides were synthesized using this synthetic route with D-glutamic acid 19 as the starting material (Scheme 3). The sugar ring precursor 20 was fluorinated in the manner described above and coupled with various silylated bases (Table 4).

Scheme 3

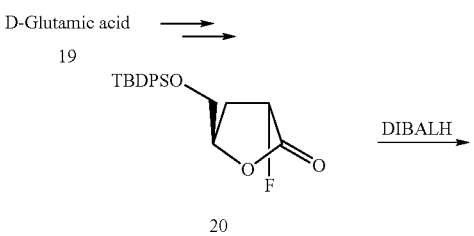

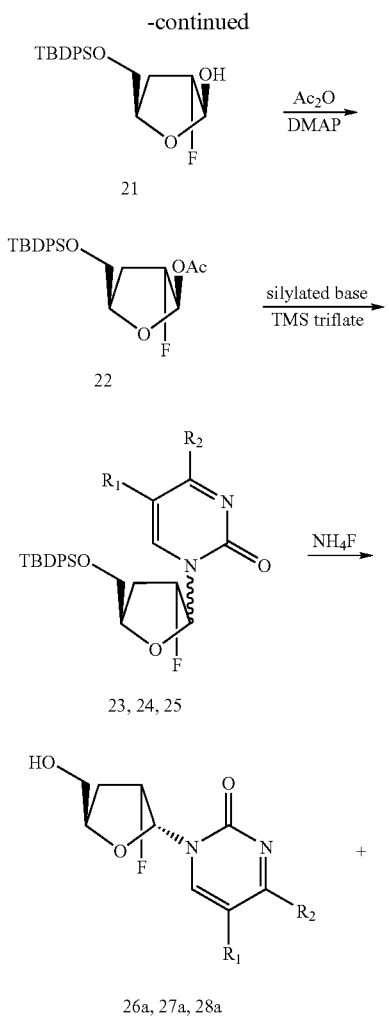

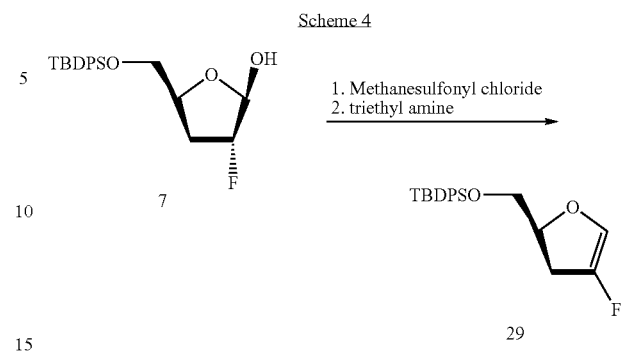

Successful synthesis of 29, as shown in Scheme 4, allows access to two categories of nucleosides. The first is the class of compounds known as 2',3'-dideoxy-2',3'-didehydro-2-2'-fluoro-nucleosides, 30, and the second is the "up"-fluoro or arabino analogs, 31, of the nucleosides described in Scheme 5 below.

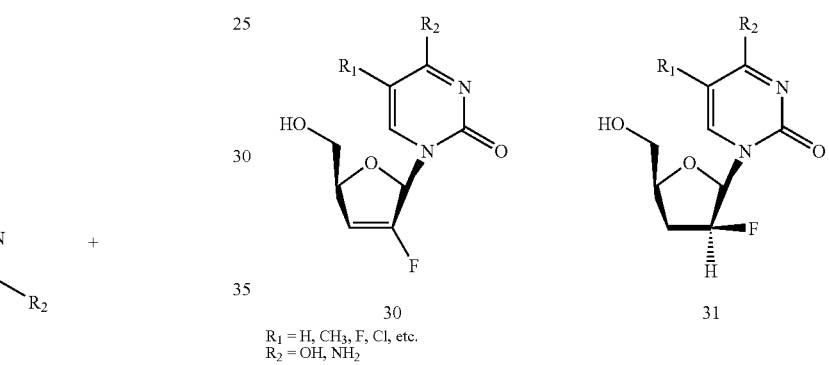

$R_1$ = H, $CH_3$, F, Cl, etc.
$R_2$ = OH, $NH_2$

Compounds 30 and 31 may be synthesized from a common intermediate 32, which may be accessed through selenylation of fluoroglycal 29.

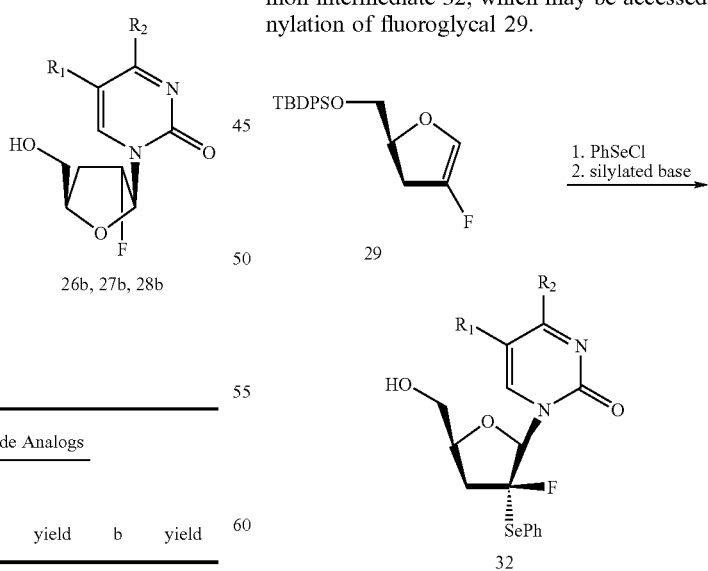

TABLE 4

Yields of Unnatural Nucleoside Analogs

| cmpd. | yield (23-25) | $R_1$ | $R_2$ | a | yield | b | yield |
|---|---|---|---|---|---|---|---|
| 23 | 87% | $CH_3$ | OH | 26a | 24% | 26b | 61% |
| 24 | 85% | F | OH | 27a | 35% | 27b | 51% |
| 25 | 99% | F | $NH_2$ | 28a | 34% | 28b | 52% |

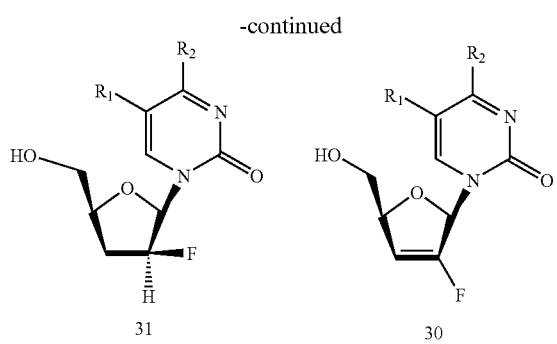

Selenylated compound 32 may be transformed into the "up" fluoro analog 31 through reduction with Raney nickel. Alternatively, oxidation of the selenide 32 with NaIO$_4$ or hydrogen peroxide followed by thermal elimination of the selenoxide intermediate lead to 30. Both of these transformations on the unfluorinated systems are well documented and have been reported (Wurster, J. A.; Ph.D. Thesis, Emory University, 1995; Wilson, L. J.; Ph.D. Thesis, Emory University, 1992).

In addition, the synthesis of the enantiomers of nucleosides 30 and 31 is also possible since they arise from the enantiomer of 29.

An alternative route for the preparation of compounds of the type represented by 30, the 2',3'-dideoxy-2',3'-didehydro-2'-flouro-nucleosides, is shown in Scheme 7. This route provides simple, direct access to this class of compounds utilizing a wide range of silylated bases and has been successfully completed.

Formation of silyl ketene acetal from 6 allows for the stereoselective addition of phenyl selenium bromide to generate compound 36 as a single isomer. Reduction and acetylation of this compound proceeds smoothly and in high yield over the two steps to 37. The α orientation of the phenyl selenyl group allows for stereoselection in the subsequent glycosylation step, and synthesis of the β isomer of the nucleoside 38 is accomplished in good yield. Compound 38 may be oxidized with hydrogen peroxide in dichloromethane to yield the elimination product 39, but in our experience, it was merely necessary to adsorb 38 onto silica gel and allow to stand for several hours, after which time 39 could be eluted from a plug column in nearly quantitative yield. Removal of the protected group from 39 to obtain the final compound 30 was performed as before and resulted in a good yield (81%) of product nucleoside.

Scheme 8

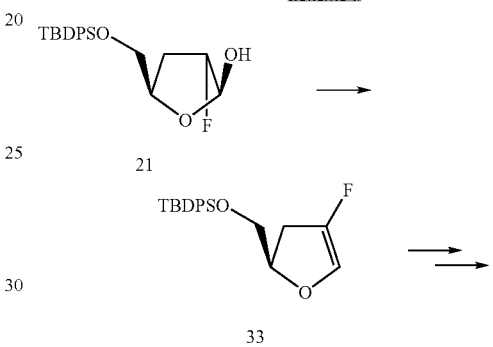

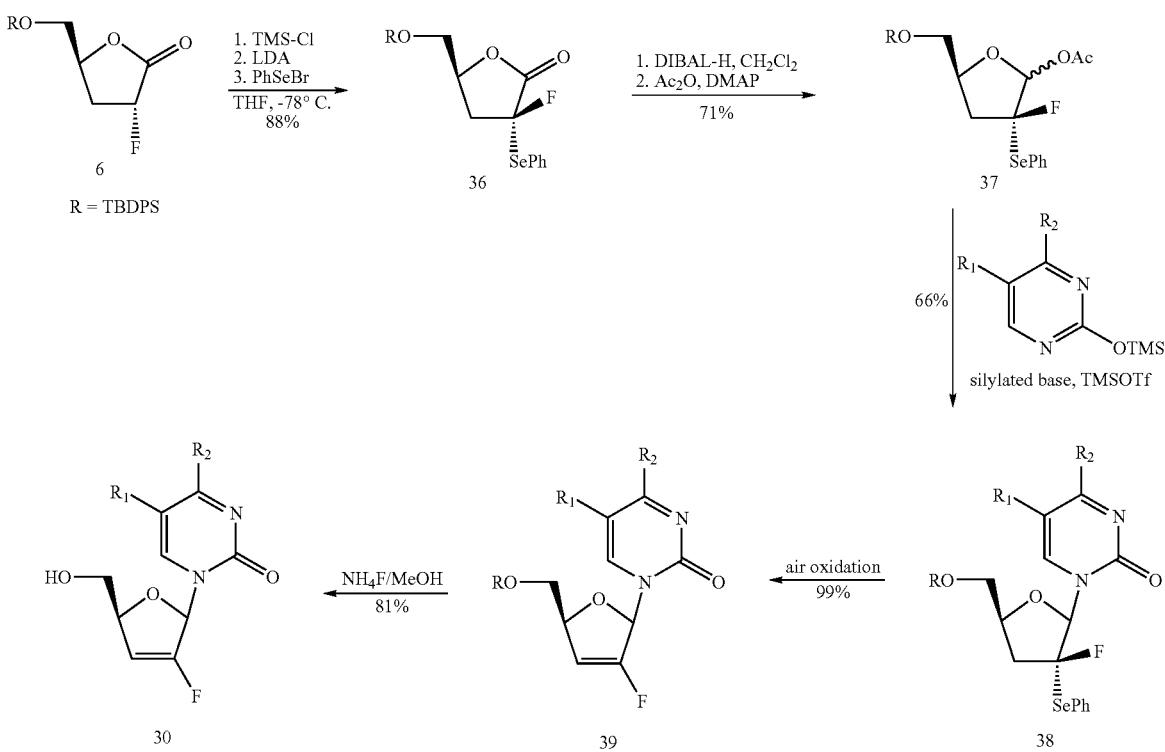

-continued

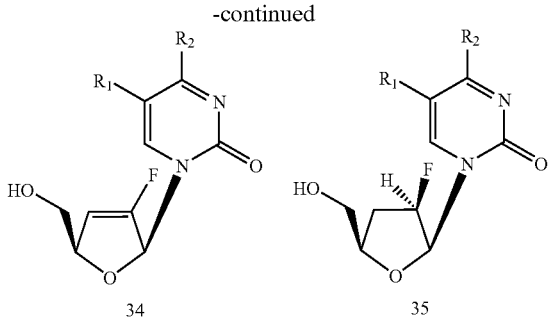

34    35

The same series of chemical transformations that were used for the synthesis of 30 and 31 may also be used for the synthesis of 34 and 35.

EXPERIMENTAL SECTION

General Procedures:

N-Fluoro-(bis)benzenesulfonimide 5 was obtained from Allied Signal, and was used without further purification. All other reagents were obtained from Aldrich Chemical Company and were used without further purification. Melting points were determined on a Thomas Hoover capillary melting point apparatus and are uncorrected. IR spectra were obtained on a Nicolet Impact 400 FT-IR spectrometer. $^1$H NMR and $^{13}$C NMR spectra were recorded on either NT-360 or Varian 400 MHz spectrometer. TLC plates were silica gel 60 $F_{254}$ (0.25 mm thickness) purchased from EM Science. Flash chromatography was carried out with silica gel 60 (230-400 mesh ASTM) from EM Science. All reactions were performed in flame-dried glassware under an atmosphere of dry argon. Solvents were removed by rotary evaporation. Elemental analyses were performed by Atlantic Microlab, Inc, Atlanta, Ga.

(2S,4R)-5-(t-butyldiphenylsiloxy)-2-fluoropentan-4-olide (20). To a flask was added (4R)-5-(t-butyldiphenylsiloxy)-pentan-4-olide (20.0 g, 0.0564 mol, 1.0 eq.) and N-fluoro-(bis)benzenesulfonimide (NFSi) 5 (17.80 g, 0.0564 mol, 1.0 eq.) in 250 mL of anhydrous THF. The solution was cooled to −78° C. and 68.0 mL (0.0680 mol, 1.2 eq.) of a 1.0 M solution of LiHMDS in THF was added dropwise over a period of 1 hr. This was allowed to stir at −78° C. for an additional 2 hrs. and was then warmed to room temperature to stir for one hour. After completion, the reaction was quenched with 10 mL of saturated $NH_4Cl$ solution. The mixture was diluted with three volumes of diethyl ether and was poured onto an equal volume of saturated $NaHCO_3$. The organic layer was washed a second time with saturated $NaHCO_3$ and once with saturated NaCl. The organic layer was dried over $MgSO_4$, filtered, and concentrated to a light yellow oil. The oil was purified by silica gel column chromatograpy using a 30% diethyl ether/70% hexanes solvent system. The resultant white solid was then crystallized from hot hexanes to yield 13.04 g (62% yield) of a transparent crystalline solid: $R_f$ (30% diethyl ether/70% hexanes)=0.26; mp 115-116° C. $^1$H NMR (360 MHz, $CDCl_3$) d 7.63-7.60 (m, 4H), 7.45-7.35 (m, 6H), 5.49 (dt, J=52.9 and 7.9 Hz, 1H), 4.69 (d, J=9.36 Hz, 1H), 3.91 (d, J=11.5 Hz, 1H), 3.60 (d, J=11.5 Hz, 1H), 2.72-2.40 (m, 2H), 1.05 (s, 9H); $^{13}$C NMR (100 MHz, $CDCl_3$) d 172.1 (d, J=20.5 Hz), 135.5, 135.4, 132.3, 131.7, 130.1, 128.0, 127.9, 85.6 (d, J=186.6 Hz), 77.3 (d, J=5.3 Hz), 65.0, 31.8 (d, J=20.5 Hz), 26.7, 19.1; IR (thin film) 2958, 1796, 1252, 1192, 1111, 1016 cm$^{-1}$; HRMS calculated for [M+Li] $C_{21}H_{25}O_3FSiLi$: 379.1717. Found: 379.1713. Anal. Calc. CHAFFS: C, 67.71; H, 6.76. Found: C, 67.72; H, 6.78.

5-O-(t-butyldiphenylsilyl)-2,3-dideoxy-2-fluoro-(L)-erythron-pentofuranose (21). To a flask was added lactone 20 (12.12 g, 0.0325 mol, 1.0 eq.) and 240 mL of anhydrous THF. The solution was cooled to −78° C. and 65 mL (0.065 mol, 2.0 eq.) of a 1.0 M solution of DIBALH in hexanes was added dropwise over a period of 30 min. This was allowed to stir at −78° C. for 3 hrs., after which time the reaction was quenched by the slow addition of 2.93 mL (0.163 mol, 5.0 eq.) of water. The reaction was allowed to warm to room temperature and stir for 1 hr., after which time a clear gelatinous solid formed throughout the entire flask. The reaction mixture was diluted with two volumes of diethyl ether and was poured onto an equal volume of saturated aqueous sodium potassium tartrate solution in an Erlenmeyer flask. This was stirred for 20 min. until the emulsion had broken. The organic layer was separated and the aqueous layer was extracted three times with 250 mL of diethyl ether. The combined organic layers were dried over $MgSO_4$, filtered, and concentrated to a light yellow oil. The product was purified by silica gel column chromatography using a 6:1 hexanes/ethyl acetate solvent system. The resulting clear oil was crystallized from boiling hexanes to give 11.98 g (98% yield) of a white crystalline solid: $R_f$ (30% diethyl ether/70% hexanes)=0.33; mp 66-67° C. $^1$H NMR (360 MHz, $CDCl_3$) d 7.68-7.66 (m, 4H), 7.55-7.38 (m, 6H), 5.39 (t, J=7.6 Hz, 1H), 4.99 (dd, J=52.2 and 4.3 Hz, 1H), 4.52 (m, 1H), 3.88 (dd, J=10.8 and 2.5 Hz, 1H), 3.65 (d, J=7.9 Hz, 1H), 3.49 (dd, J=7.9 and 1.8 Hz, 1H), 2.44-2.07 (m, 2H), 1.07 (s, 9H); $^{13}$C NMR (100 MHz, $CDCl_3$) d 135.7, 135.5, 132.2, 132.1, 130.2, 130.0, 129.8, 127.9, 127.7, 99.8 (d, J=31.1 Hz), 96.6 (d, J=178.3 Hz), 79.4, 64.8, 29.9 (d, J=21.2 Hz), 26.8, 19.2; IR (thin film) 3423, 2932, 1474, 1362, 1113 cm$^{-1}$; HRMS calculated for [M+Li] $C_{21}H_{27}O_3FSiLi$: 381.1874. Found: 381.1877. Anal. Calc. $C_{21}H_{27}O_3FSi$: C, 67.35; H, 7.27. Found: C, 67.42; H, 7.31.

1-O-Acetyl-5-O-(t-butyldiphenylsilyl)-2,3-dideoxy-2-fluoro-(L)-erythron-pentofuranose (22). To a flask was added lactol 21 (8.50 g, 0.0227 mol, 1.0 eq.) and 170 mL of anhydrous $CH_2Cl_2$. Then, DMAP (0.277 g, 0.00277 mol, 0.1 eq.) and acetic anhydride (13.5 mL, 0.143 mol, 6.3 eq.) were added and stirred at room temperature overnight. Upon completion, the reaction was poured onto saturated $NaHCO_3$ solution. The organic layer was separated, and the aqueous layer was extracted three times with chloroform. The combined organic layers were dried over $MgSO_4$, filtered, and the solvent removed to yield a light yellow oil. The oil was purified by silica gel column chromatography using an 8:1 hexanes/ethyl acetate solvent system to give 9.85 g (99% yield) of a clear colorless oil: $R_f$ (30% diethyl ether/70% hexanes)=0.44; $^1$H NMR (360 MHz, $CDCl_3$) d 7.69-7.67 (m, 4H), 7.43-7.38 (m, 6H), 6.30 (d, J=10.4 Hz, 1H), 5.06 (d, J=54.9 Hz, 1H), 4.53 (m, 1H), 3.81 (dd, J=10.8 and 4.3 Hz, 1H), 3.72 (dd, J=10.8 and 4.3 Hz, 1H), 2.38-2.12 (m, 2H), 1.89 (s, 3H), 1.07 (s, 9H); $^{13}$C NMR (100 MHz, $CDCl_3$) d 169.4, 135.6, 135.5, 133.2, 133.1, 129.8, 129.7, 127.8, 127.7, 99.3 (d, J=34.1 Hz), 95.5(d, J=178.2 Hz), 81.4, 65.3, 31.6 (d, J=20.5 Hz), 26.8, 21.1, 19.3; IR (thin film) 3074, 2860, 1750, 1589, 1229, 1113 cm$^{-1}$; HRMS calculated for [M−OCOCH$_3$] $C_{21}H_{26}O_2FSi$: 357.1686. Found: 357.1695. Anal. Calc. $C_{23}H_{29}O_4FSi$: C, 66.32; H, 7.02. Found: C, 66.30; H, 7.04.

Representative procedure for the coupling of a silylated base with 22: (L)-5'-O-(t-butyldiphenylsilyl)-2',3-dideoxy-2'-fluoro-5-fluorocytidine (25). To a flask equipped with a short-path distillation head was added 5-fluorocytosine (2.01 g, 15.6 mmol, 5.0 eq), 35 mL of 1,1,1,3,3,3-hexamethyldisilazane, and a catalytic amount (~1 mg) of $(NH_4)_2SO_4$. The white suspension was heated to boiling for 1 hr. until the base was silylated and reaction was a clear solution. The excess HMDS was distilled off and the oily residue that remained was placed under vacuum for 1 hr. to remove the last traces of HMDS. A white solid resulted which was dissolved, under argon, in 5 mL of anhydrous 1,2-dichloroethane. To this clear solution was added a solution of acetate 22 (1.30 g, 3.12 mmol, 1.0 eq.) in 5 mL of anhydrous 1,2-dichloroethane. To this was added, at room temperature, trimethylsilyl trifluoromethanesulfonate (3.32 mL, 17.2 mmol, 5.5 eq.). The reaction was monitored by TLC (10% methanol/90% $CH_2Cl_2$) and was observed to be complete in 4 hrs. The reaction mixture was poured onto saturated $NaHCO_3$. The organic layer was then separated, and the aqueous layer was extracted three times with chloroform. The combined organic layers were dried over $MgSO_4$, filtered, and the solvent removed to yield a white foam. The compound was purified by silica gel column chromatography using a gradient solvent system from 100% $CH_2Cl_2$ to 10% methanol in $CH_2Cl_2$. The compound was isolated as 1.51 g (99% yield) of a white foam: mixture of anomers $R_f$ (100% EtOAc)=0.36; mp 74-80° C. $^1$H NMR (400 MHz, $CDCl_3$) d 8.84 (bs, 1H), 8.04 (d, J=6.4 Hz, 0.67H), 7.67-7.63 (m, 4H), 7.51-7.39 (m, 6.33H), 6.11 (d, J=20 Hz, 0.33H), 5.98 (d, J=16.4 Hz, 0.67H), 5.88 (bs, 1H), 5.41 (d, J=52.4 Hz, 0.33H), 5.23 (dd, J 50.4 and 4 Hz, 0.67H), 4.56 (m, 0.33H), 4.45 (m, 0.67H), 4.23 (dd, J=12.0 and 1.6 Hz, 0.67H), 3.89 (dd, J=11.2 and 3.2 Hz, 0.33H), 3.74-3.66 (m, 1H), 2.45-1.96 (m, 2H), 1.09 (s, 6H), 1.06 (s, 3H); $^{13}$C NMR (100 MHz, $CDCl_3$) d 158.6 (d, J=14.4 Hz), 158.4 (d, J=14.4 Hz), 153.9, 153.8, 136.6 (d, J=240.5 Hz), 136.3 (d, J=239.7 Hz), 135.6, 135.56, 135.5, 135.4, 133.1, 132.9, 132.5, 132.4, 130.1, 130.0, 129.9, 127.9, 127.8, 125.8 (d, J=33.4 Hz), 124.6 (d, J=32.6 Hz), 96.5 (d, J=182.0 Hz), 91.7 (d, J=185.1), 90.7 (d, J=35.6 Hz), 87.7 (d, J=15.2 Hz), 81.5, 79.5, 64.9, 63.0, 33.5 (d, J=20.5 Hz), 30.6 (d, J=20.4 Hz), 26.9, 26.8, 19.22, 19.18; IR (thin film) 3300, 2960, 1682, 1608, 1513, 1109 cm$^{-1}$; HRMS calculated for [M+Li] $C_{25}H_{29}N_3O_3SiF_2Li$: 492.2106. Found: 492.2085. Anal. Calc. $C_{25}H_{29}N_3O_3SiF_2 \cdot 1/2H_2O$: C, 60.71; H, 6.11; N, 8.50. Found: C, 60.67; H, 6.03; N, 8.44.

Representative Procedure for the deprotection of silyl-protected nucleosides: α- and β-(L)-2',3'-dideoxy-2'-fluoro-5-fluoro cytidine (28a and 28b): Nucleoside 25 (1.098 g, 2.26 mmol, 1.0 eq) was dissolved in 15 mL of methanol to which was added ammonium fluoride (0.838 g, 22.6 mmol, 10.0 eq.). This was stirred vigorously for 24 hrs., after which time TLC. (15% ethanol/85% ethyl acetate) revealed that the reaction was complete. The reaction mixture was diluted with three volumes of ethyl acetate and was filtered through a small (1 cm) silica gel plug. The plug was rinsed with 200 mL of 15% ethanol 185% ethyl acetate solution and the solvent was removed to yield a white foam. The compound was purified by silica gel column chromatography using a 15% ethanol/85% ethyl acetate solvent system which also effected the separation of the α and β anomers. The yield of a as a white foam was 0.190 g (0.768 mmol, 34% yield) and the yield of P as a white foam was 0.290 g (1.17 mmol, 52% yield): (28a) $R_f$ (15% EtOH, 85% EtOAc)=0.22; mp 199-203° C. (dec.). $^1$H NMR (400 MHz, $CD_3OD$) d 7.78 (d, J=6.8 Hz, 1H), 6.07 (d, J=19.2 Hz, 1H), 5.37 (d, J=54.0 Hz, 1H), 4.60 (m, 1H), 3.80 (dd, J=12.0 and 3.2 Hz, 1H), 3.56 (dd, J=12.4 and 4.4 Hz, 1H), 2.40-2.00 (m, 2H); $^{13}$C NMR (100 MHz,DMSO-$d_6$) d 157.7 (d, J=13.6 Hz), 153.2, 135.9 (d, J=239.0 Hz), 126.2 (d, J=31.1 Hz), 92.4 (d, J=183.6 Hz), 86.7 (d, J=15.2 Hz), 79.6, 62.7, 33.3 (d, J=20.5 Hz); IR (KBr) 3343, 3100, 1683, 1517, 1104 cm$^{-1}$; HRMS calculated for [M+Li] $C_9H_{11}N_3O_3F_2Li$: 254.0929. Found: 254.0919. Anal. Calc. $C_9H_{11}N_3O_3F_2 \cdot 1/2H_2O$: C, 42.19; H, 4.72; N, 16.40. Found: C, 42.44; H, 4.56; N, 16.56. (28b) $R_f$ (15% EtOH, 85% EtOAc)=0.37; mp 182-186° C. (dec.). $^1$H NMR (400 MHz, DMSO-$d_6$) d 8.32 (d, J=7.6 Hz, 1H), 7.79 (bs, 1H), 7.53 (bs, 1H), 5.81 (d, J=16.8 Hz, 1H), 5.37 (t, J=4.8 Hz), 5.18 (dd, J=51.6 and 3.2 Hz, 1H), 4.32 (m, 1H), 3.88 (dd, J=12.0 and 2.8 Hz, 1H), 3.59 (dd, J=12.4 and 2.4 Hz, 1H), 2.20-1.99 (m, 2H); $^{13}$C NMR (100 MHz, DMSO-$d_6$) d 157.7 (d, J=13.7 Hz), 153.2, 136.1 (d, J=237.4 Hz), 125.3 (d, J=33.4 Hz), 97.3 (d, J=176.8 Hz), 89.9 (d, J=35.7 Hz), 81.6, 60.2, 30.3 (d, J=19.7 Hz); IR (KBr) 3487, 2948, 1678, 1509, 1122 cm$^{-1}$; HRMS calculated for [M+Li] $C_9H_{11}N_3O_3F_2Li$: 254.0929. Found: 254.0935. Anal. Calc. $C_9H_{11}N_3O_3F_2$: C, 43.73; H, 4.49; N, 17.00. Found: C, 43.69; H, 4.53; N, 16.92.

(D)-5'-O-(t-butyldiphenylsilyl)-2',3'-dideoxy-2'-fluoro-5-fluorouridine (9). mixture of anomers $R_f$ (1:1 hexanes/EtOAc)=0.48; mp 65-70 C. $^1$H NMR (400 MHz, $CDCl_3$) d 10.0 (bm, 1H), 7.99 (d, J=5.6 Hz, 0.63H), 7.65 (m, 4H), 7.42 (m, 6.37H), 6.12 (dd, J=18.0 and 1.6 Hz, 0.37H), 6.00 (d, J=16 Hz, 0.63H), 5.37 (dd, J=54.6 and 2.4 Hz, 0.37H), 5.22 (dd, J=50.4 and 4 Hz, 0.63H), 4.57 (m, 0.37H), 4.44 (m, 0.63H), 4.22 (dd, J=12.2 and 2.0 Hz, 0.63H), 3.92 (dd, J=11.2 and 3.2 Hz, 0.37H), 3.70 (m, 1H), 2.22 (m, 2H), 1.09 (s, 5.67H), 1.074 (s, 3.33H); $^{13}$C NMR (100 MHz, $CDCl_3$) d 157.2 (d, J=31.7 Hz), 157.1 (d, J=25.8 Hz), 149.1, 148.8, 140.4 (d, J=236.6 Hz), 140.1 (d, J=235.2 Hz), 135.6, 135.5, 135.4, 132.9, 132.7, 132.4, 132.3, 130.1, 130.0, 129.9, 127.9, 127.8, 125.1 (d, J=34.9 Hz), 123.6 (d, J=34.1 Hz), 96.4 (d, J=182.0 Hz), 92.0 (d, J=185.9 Hz), 90.2 (d, J=37.2 Hz), 87.0 (d, J=15.2 Hz), 81.7, 79.8, 64.8, 63.0, 33.3 (d, J=21.2 Hz), 31.0 (d, J=21.2 Hz), 26.9, 26.8, 19.2; IR (thin film) 3185, 1722, 1117 cm$^{-1}$; HRMS calculated for [M+1] $C_{25}H_{29}N_2O_4SiF_2$: 487.1866. Found: 487.1853. Anal. Calc. $C_{25}H_{28}N_2O_4SiF_2$: C, 61.71; H, 5.80; N, 5.76. Found: C, 61.72; H, 5.86; N, 5.72.

(D)-5'-O-(t-butyldiphenylsilyl)-2',3'-dideoxy-2'-fluoro-5-fluorocytidine (10). mixture of anomers $R_f$ (100% EtOAc) =0.36; mp 75-81° C. $^1$H NMR (400 MHz, $CDCl_3$) d 8.50 (bm, 1H), 8.05 (d, J=6.0 Hz, 0.67H), 7.67-7.63 (m, 4H), 7.51-7.39 (m, 6.33H), 6.10 (d, J=20 Hz, 0.33H), 5.98 (d, J=16.4 Hz, 0.67H), 5.62 (bm, 1H), 5.41 (d, J=52.4 Hz, 0.33H), 5.23 (dd, J=51.6 and 4 Hz, 0.67H), 4.57 (m, 0.33H), 4.48 (m, 0.67H), 4.24 (dd, J=12.4 and 2.0 Hz, 0.67H), 3.89 (dd, J=11.2 and 3.2 Hz, 0.33H), 3.74-3.66 (m, 1H), 2.39-1.95 (m, 2H), 1.09 (s, 6H), 1.06 (s, 3H); $^{13}$C NMR (100 MHz, $CDCl_3$) d 158.4 (d, J=14.4 Hz), 158.3 (d, J=15.2 Hz), 153.8, 153.7, 136.5 (d, J=240.5 Hz), 136.2 (d, J=241.8 Hz), 135.59, 135.56, 135.4, 133.0, 132.9, 132.5, 132.4, 130.1, 130.0, 129.9, 127.9, 127.8, 124.8 (d, J=31.9 Hz), 96.5 (d, J=181.3 Hz), 91.8 (d, J=175.2 Hz), 90.7 (d, J=24.9 Hz), 87.8 (d, J=21.2 Hz), 81.6, 79.6, 64.9, 63.0, 33.5 (d, J=19.7 Hz), 30.6 (d, J=21.3 Hz), 26.9, 26.8, 19.2, 14.2; IR (thin film) 3304, 2959, 1680, 1621, 1508, 1105 cm$^{-1}$; HRMS calculated for [M+Li] $C_{25}H_{29}N_3O_3SiF_2Li$: 492.2106. Found: 492.2110. Anal. Calc. $C_{25}H_{29}N_3O_3SiF_2$: C, 61.84; H, 6.02; N, 8.65. Found: C, 61.86; H, 6.09; N, 8.55.

(D)-$N^4$-acetyl-5'-O-(t-butyldiphenylsilyl)-2',3'-dideoxy-2'-fluoro-cytidine (11). mixture of anomers $R_f$ (15% EtOH, 85% EtOAc)=0.75; mp 81-86° C. $^1$H NMR (400 MHz, $CDCl_3$) d 10.58 (bs, 1H), 8.40 (d, J=7.2 Hz, 0.61H), 7.86 (d, J=7.6 Hz, 0.38H), 7.67-7.65 (m, 4H), 7.51-7.41 (m, 6H), 7.27 (d, J=8.4 Hz, 11H), 6.12 (t, J=15.8 Hz, 1H), 5.51 (d, J=52.6 Hz, 0.388H), 5.21 (dd, J=50.8 and 2.9 Hz, 0.611H), 4.62 (m, 0.388H), 4.54 (m, 0.611H), 4.28 (d, J=11.5 Hz, 0.611H), 3.95 (dd, J=11.9 and 3.2 Hz, 0.388H), 3.79-3.70 (m, 11H), 2.46-2.04 (m, 5H), 1.12 (s, 5.49H), 1.07 (s, 3.42H); $^{13}$C NMR (100 MHz, CDCl$_3$) d 171.5, 171.3, 163.4, 154.9, 144.9, 144.1, 135.5, 135.4, 133.0, 132.8, 132.5, 132.2, 130.2, 130.1, 129.9, 128.0, 127.8, 96.8 (d, J=91.1 Hz), 96.2 (d, J=147.9 Hz), 92.3, 91.2 (d, J=35.7 Hz), 90.5, 88.5 (d, J=15.9 Hz), 81.9, 80.1, 64.7, 62.9, 33.5 (d, J=20.5 Hz), 30.5 (d, J=20.5 Hz), 26.9, 26.8, 24.9, 24.8, 19.3, 19.2; IR (thin film) 3237, 2932, 1722, 1671, 1559, 1493, 1107 cm$^{-1}$; HRMS calculated for [M+Li] C$_{27}$H$_{32}$N$_3$O$_4$FSiLi: 516.2306. Found: 516.2310. Anal. Calc. C$_{27}$H$_{32}$N$_3$O$_4$FSi: C, 63.63; H, 6.33; N, 8.24. Found: C, 63.45; H, 6.42; N, 8.09.

(D)-5'-O-(t-butyldiphenylsilyl)-2',3'-dideoxy-2'-fluoro-cytidine (12). mixture of anomers R$_f$ (15% EtOH, 85% EtOAc)=0.50; mp 98-104° C. $^1$H NMR (360 MHz, CDCl$_3$) d 7.97 (d, J=7.2 Hz, 0.64H, H-6), 7.65 (m, 4H), 7.47-7.38 (m, 6.36H), 6.15 (d, J=20.5 Hz, 0.36H), 6.05 (d, J=16.6 Hz, 0.64H), 5.83 (d, J=7.9 Hz, 0.36H), 5.46 (d, J=7.2 Hz, 0.64H), 5.30-5.10 (m, 1H), 4.55 (m, 0.36H), 4.44 (m, 0.64H), 4.22 (d, J=9.7 Hz, 0.64H), 3.88-3.63 (m, 1.36H), 2.38-1.95 (m, 2H), 1.09 (s, 5.76H), 1.06 (s, 3.24H); $^{13}$C NMR (100 MHz, CDCl$_3$) d 166.1, 155.8, 141.5, 140.5, 135.6, 135.4, 133.1, 132.9, 132.8, 132.4, 130.1, 130.0, 129.8, 128.0, 127.9, 127.8, 96.7 (d, J=181.3 Hz), 93.4 (d, J=140.3 Hz), 94.5, 90.8 (d, J=35.6 Hz), 90.8, 87.8 (d, J=15.9 Hz), 81.2, 79.4, 65.0, 63.2, 33.7 (d, J=21.2 Hz), 30.8 (d, J=20.4 Hz), 26.9, 26.8, 19.3, 19.2; IR (thin film) 3470, 3339, 1644, 1487, 1113 cm$^{-1}$; HRMS calculated for [M+Li] C$_{25}$H$_{30}$N$_3$O$_3$FSiLi: 474.2201. Found: 474.2198. Anal. Calc. C$_{25}$H$_{30}$N$_3$O$_3$FSi: C, 64.21; H, 6.47; N, 8.99. Found: C, 64.04; H, 6.58; N, 8.76.

α-(D)-2',3'-Dideoxy-2'-fluoro-5-fluorouridine (14a). R$_f$ (100% EtOAc)=0.38; mp 153-155° C. $^1$H NMR (360 MHz, CD$_3$OD) d 7.80 (d, J=6.8 Hz, 1H), 6.11 (d, J=18.7 Hz, 1H), 5.35 (d, J=52.9 Hz, 1H), 4.59 (m, 1H), 3.81 (d, J=11.9 Hz, 1H), 3.57 (dd, J=12.6 and 3.6 Hz, 1H), 2.36-2.15 (m, 2H); $^{13}$C NMR (100 MHz, CD$_3$OD) d 159.6 (d, J=25.8 Hz), 150.7, 141.5 (d, J=230.6 Hz), 127.0 (d, J=34.9 Hz), 93.9 (d, J=185.1 Hz), 88.5 (d, J=15.1 Hz), 81.8, 64.3, 34.3 (d, J=20.5 Hz); IR (KBr) 3421, 3081, 1685, 1478, 1111 cm$^{-1}$; HRMS calculated for [M+Li] C$_9$H$_{10}$N$_2$O$_4$F$_2$Li: 255.0769. Found: 255.0778. Anal. Calc. C$_9$H$_{10}$N$_2$O$_4$F$_2$: C, 43.56; H, 4.06; N, 11.29. Found: C, 43.59; H, 4.11; N, 11.17.

β-(D)-2',3'-Dideoxy-2'-fluoro-5-fluorouridine (14b). R$_f$ (100% EtOAc) 0.54; mp 152-154(C. $^1$H NMR (360 MHz, CD$_3$OD) d 8.41 (d, J=7.2 Hz, 1H), 5.89 (d, J=16.6 Hz, 1H), 5.21 (dd, J=51.5 and 3.6 Hz, 1H), 4.41 (m, 1H), 4.00 (d, J=12.6 Hz, 1H), 3.67 (d, J=12.2 Hz, 1H), 2.25-2.09 (m, 2H); $^{13}$C NMR (100 MHz, CD$_3$OD) d 159.7 (d, J=25.8 Hz), 150.7, 141.8 (d, J=229.8 Hz), 126.3 (d, J=36.4 Hz), 98.3 (d, J=179 Hz), 91.9 (d, J=37.1 Hz), 83.6, 61.9, 31.9 (d, J=20.5 Hz); IR (KBr) 3417, 3056, 1684, 1474, 1105 cm$^{-1}$; HRMS calculated for [M+Li] C$_9$H$_{10}$N$_2$O$_4$F$_2$Li: 255.0769. Found: 255.0764. Anal. Calc. C$_9$H$_{10}$N$_2$O$_4$F$_2$: C, 43.56; H, 4.06; N, 11.29. Found: C, 43.37; H, 3.98; N, 11.22.

α-(D)-2',3'-Dideoxy-2'-fluoro-5-fluorocytidine (15a). R$_f$ (15% EtOH, 85% EtOAc)=0.22; mp 198-202° C. (dec.). $^1$H NMR (400 MHz, CD$_3$OD) d 7.78 (d, J=6.8 Hz, 1H), 6.07 (d, J=18.8 Hz, 1H), 5.37 (d, J=54.0 Hz, 1H), 4.59 (m, 1H), 3.80 (dd, J=12.0 and 3.2 Hz, 1H), 3.57 (dd, J=12.4 and 4.4 Hz, 1H), 2.38-2.14 (m, 2H); $^{13}$C NMR (100 MHz, CD$_3$OD) d 159.9 (d, J=13.6 Hz), 156.5, 138.3 (d, J=240.4 Hz), 127.5 (d, J=33.4 Hz), 93.6 (d, J=184.3 Hz), 89.5 (d, J=15.9 Hz), 81.8, 64.4, 34.5 (d, J=20.5 Hz); IR (KBr) 3486, 3098, 1681, 1519, 1108 cm$^{-1}$; HRMS calculated for [M+Li] C$_9$H$_{11}$N$_3$O$_3$F$_2$Li: 254.0929. Found: 254.0929. Anal. Calc. C$_9$H$_{11}$N$_3$O$_3$F$_2$.1/2H$_2$O: C, 42.19; H, 4.72; N, 16.40. Found: C, 41.86; H, 4.75; N, 16.36.

β-(D)-2',3'-Dideoxy-2'-fluoro-5-fluorocytidine (15b). R$_f$ (15% EtOH, 85% EtOAc)=0.37; mp 181-183° C. (dec.). $^1$H NMR (400 MHz, CD$_3$OD) d 8.45 (d, J=7.2 Hz, 1H), 5.92 (dd, J=16.2 and 1.2 Hz, 1H), 5.18 (dd, J=50.8 and 4.0 Hz, 1H), 4.46 (m, 1H), 4.05 (dd, J=12.4 and 2.4 Hz, 1H), 3.72 (dd, J=12.8 and 2.4 Hz, 1H), 2.27-2.05 (m, 2H); $^{13}$C NMR (100 MHz, CD$_3$OD) d 159.9 (d, J=13.6 Hz), 156.5, 138.5 (d, J=240.5 Hz), 126.9 (d, J=33.4 Hz), 98.4 (d, J=179.0 Hz), 92.5 (d, J=36.4 Hz), 83.6, 61.9, 31.6 (d, J=20.5 Hz); IR (KBr) 3494, 2944, 1689, 1522, 1106 cm$^{-1}$; HRMS calculated for [M+Li] C$_9$H$_{11}$N$_3$O$_3$F$_2$Li: 254.0929. Found: 254.0936. Anal. Calc. C$_9$H$_{11}$N$_3$O$_3$F$_2$: C, 43.73; H, 4.49; N, 17.00. Found: C, 43.84; H, 4.47; N, 17.05.

α-(D)-N$^4$-acetyl-2',3'-dideoxy-2'-fluoro-cytidine (16a). R$_f$ (15% EtOH, 85% EtOAc)=0.40; mp 208-212° C. $^1$H NMR (360 MHz, DMSO-d$_6$) d (10.91, bs, 1H), 8.05 (d, J=7.2 Hz, 1H), 7.25 (d, J=7.2 Hz, 1H), 6.08 (dd, J=19.1 and 2.9 Hz, 1H), 5.42 (d, J=52.2 Hz, 1H), 4.97 (bs, 1H), 4.54 (m, 1H), 3.63 (d, J=13.0 Hz, 1H), 3.47 (d, J=13.3 Hz, 1H), 2.35-2.15 (m, 2H), 2.11 (s, 3H); $^{13}$C NMR (100 MHz, DMSO-d$_6$) d 171.0, 162.6, 154.3, 145.7, 94.9, 92.0 (d, J=183.6 Hz), 87.5 (d, J=15.9 Hz), 80.2, 62.6, 33.3 (d, J=19.7 Hz), 24.4; IR (KBr) 3436, 3227, 1702, 1661, 1442, 1102 cm$^{-1}$; HRMS calculated for [M+Li] C$_{11}$H$_{14}$N$_3$O$_4$FLi: 278.1128. Found: 278.1136. Anal. Calc. C$_{11}$H$_{14}$N$_3$O$_4$F: C, 48.71; H, 5.20; N, 15.49. Found: C, 48.73; H, 5.23; N, 15.52.

β-(D)-N$^4$-acetyl-2',3'-dideoxy-2'-fluoro-cytidine (16b). R$_f$ (15% EtOH, 85% EtOAc)=0.50; mp 174-178° C. $^1$H NMR (360 MHz, DMSO-d$_6$) d (10.90, bs, 1H), 8.46 (d, J=7.2 Hz, 1H), 7.18 (d, J=7.2 Hz, 1H), 5.90 (d, J=16.9 Hz, 1H), 5.27 (d, J=52.9 Hz, 1H), 5.27 (bs, 1H), 4.39 (m, 1H), 3.88 (d, J=13.0 Hz, 1H), 3.61 (d, J=13.0 Hz, 1H), 2.09 (s, 3H), 2.20-1.85 (m, 2H); $^{13}$C NMR (100 MHz, DMSO-d$_6$) d 171.0, 162.6, 154.4, 144.7, 97.0 (d, J=177.5 Hz), 95.0, 90.7 (d, J=36.6 Hz), 82.2, 60.3, 30.3 (d, J=19.7 Hz), 24.3; IR (KBr) 3447, 3245, 1703, 1656, 1497, 1122 cm$^{-1}$; HRMS calculated for [M+Li] C$_{11}$H$_{14}$N$_3$O$_4$FLi: 278.1128. Found: 278.1133. Anal. Calc. C$_{11}$H$_{14}$N$_3$O$_4$F: C, 48.71; H, 5.20; N, 15.49. Found: C, 48.65; H, 5.22; N, 15.46.

α-(D)-2',3'-Dideoxy-2'-fluoro-cytidine (17a). R$_f$(15% EtOH, 85% EtOAc)=0.08; mp 234-237° C. (dec.). $^1$H NMR (400 MHz, DMSO-d$_6$) d 7.52 (d, J=7.6 Hz, 1H), 7.21 (bm, 2H), 6.05 (dd, J=20.4 and 3.2 Hz, 1H), 5.73 (d, J=7.2 Hz, 1H), 5.28 (d, J=52.4 Hz, 1H), 4.93 (t, J=5.6 Hz, 1H), 4.45 (m, 1H), 3.58 (m, 1H), 3.43 (m, 1H), 2.26-2.13 (m, 2H); $^{13}$C NMR (100 MHz, DMSO-d$_6$) d 165.8, 155.0, 141.6, 93.3, 92.2 (d, J=182.8 Hz), 86.6 (d, J=15.1 Hz), 79.4, 62.8, 33.3 (d, J=19.7 Hz); IR (KBr) 3366, 3199, 1659, 1399, 1122 cm$^{-1}$; HRMS calculated for [M+Li] C$_9$H$_{12}$N$_3$O$_3$FLi: 236.1023. Found: 236.1014. Anal. Calc. C$_9$H$_{12}$N$_3$O$_3$F: C, 47.16; H, 5.28; N, 18.33. Found: C, 47.40; H, 5.34; N, 18.51.

β-(D)-2',3'-Dideoxy-2'-fluoro-cytidine (17b). Nucleoside 25 (0.160 g, 0.59 mmol) was dissolved in 10 mL of saturated methanolic ammonia. After stirring for 5 min., the reaction was complete. The methanolic ammonia was removed and the resultant white solid was placed under vacuum and heated gently in a 60° C. water bath for 2 hrs. to remove the acetamide by-product through sublimation. The white solid was crystallized from 5% methanol/95% methylene chloride to give a quantitative yield of a white crystalline solid. R$_f$ (15% EtOH, 85% EtOAc)=0.18; mp 191-195° C. (dec.). $^1$H NMR (360 MHz, CD$_3$OD) d 8.10 (d, J=7.2 Hz, 1H), 5.92 (d, J=17.3 Hz, 1H), 5.82 (d, J=7.6 Hz, 1H), 5.13 (d, J=50.0 Hz, 1H), 4.39 (m, 1H), 3.97 (d, J=12.2 Hz, 1H), 3.68 (dd, J=13.0 and 2.5 Hz, 1H), 2.21-2.00 (m, 2H); $^{13}$C NMR (100 MHz, CD$_3$OD) d 165.9, 155.0, 140.8, 97.3 (d, J=176.8 Hz), 93.6, 90.3 (d, J=35.6 Hz), 81.3, 60.7, 31.0 (d, J=20.5 Hz); IR (KBr) 3397, 3112, 1680, 1400, 1178, 1070 cm$^{-1}$; HRMS calculated for [M+Li] C$_9$H$_{12}$N$_3$O$_3$FLi: 236.1024. Found: 236.1028. Anal. Calc. C$_9$H$_{12}$N$_3$O$_3$F: C, 47.16; H, 5.28; N, 18.33. Found: C, 47.01; H, 5.21; N, 18.29.

(L)-5'-O-(t-butyldiphenylsilyl)-2',3'-dideoxy-2'-fluoro-thymidine (23). mixture of anomers R$_f$ (10% MeOH/90% CH$_2$Cl$_2$)=0.56; mp 61-65° C. $^1$H NMR (360, MHz, CDCl$_3$) d 9.48 (bs, 1H), 7.67 (m, 4H), 7.45-7.37 (m, 7H), 6.15 (dd, J=20.2 and 3.2 Hz, 0.36H), 5.99 (d, J=18.4 Hz, 0.64H), 5-34 (d, J=51.8 Hz, 0.36H), 5.24 (dd, J=52.2 and 4.3 Hz, 0.64H), 4.59 (m, 0.36H), 4.45 (m, 0.64H), 4.17 (dd, J=12.2 and 2.5 Hz, 0.64H), 3.91 (dd, J=11.9 and 2.9 Hz, 0.36H), 3.81 (dd, J=11.5 and 2.9 Hz, 0.64H), 3.68 (dd, J=10.8 and 3.6 Hz, 0.36H), 2.40-2.12 (m, 2H), 1.94 (s, 1.08H), 1.61 (s, 1.92H), 1.10 (s, 5.76H), 1.07 (s, 3.24H); $^{13}$C NMR (100 MHz, CDCl$_3$) d 164.1, 164.0, 150.4, 150.2, 136.4, 135.6, 135.5, 135.4, 135.3, 135.2, 133.0, 132.8, 132.6, 130.1, 130.0, 129.9, 127.94, 127.90, 127.8, 110.8, 109.8, 96.4 (d, J=181.3 Hz), 92.1 (d, J 185.8 Hz), 90.7 (d, J=36.4 Hz), 86.6 (d, J=15.2 Hz), 80.9, 79.4, 64.9, 63.6, 33.4 (d, J=20.5 Hz), 32.0 (d, J=21.2 Hz), 27.0, 26.8, 19.4, 19.2, 12.6, 12.2; IR (thin film) 3183, 3050, 1696, 1506, 1188 cm$^{-1}$; HRMS calculated for [M+Li] C$_{26}$H$_{31}$N$_2$O$_4$SiF: 489.2197. Found: 489.2175. Anal. Calc. C$_{26}$H$_{31}$N$_2$O$_4$SiF: C, 64.71; H, 6.47; N, 5.80. Found: C, 64.88; H, 6.56; N, 5.76.

(L)-5'-O-(t-butyldiphenylsilyl)-2',3'-dideoxy-2'fluoro-5-fluorouridine (24). mixture of anomers R$_f$ (1:1 hexanes/EtOAc)=0.48; mp 65-71° C. $^1$H NMR (400 MHz, CDCl$_3$) d 9.08 (bs, 0.4H), 9.00 (bs, 0.6H) 8.01 (d, J=5.4 Hz, 0.6H), 7.65 (m, 4H), 7.42 (m, 6.4H), 6.10 (dd, J=20.2 and 1.4 Hz, 0.4H), 6.00 (d, J=16.0 Hz, 0.6H), 5.35 (dd, J=52.4 and 1.6 Hz, 0.4H), (5.22, dd, J=51.2 and 4 Hz, 0.6H), 4.57 (m, 0.4H), 4.44 (m, 0.6H), 4.22 (dd, J=12.4 and 2.0 Hz, 0.6H), 3.91 (dd, J=11.2 and 2.9 Hz, 0.4H), 3.70 (m, 1H), 2.45-2.00 (m, 2H), 1.09 (s, 5.4H), 1.07 (s, 3.6H); $^{13}$C NMR (100 MHz, CDCl$_3$) d 156.9 (d, J=26.5 Hz), 148.8, 148.6, 146.3 (d, J=236.7 Hz), 140.1 (d, J=235.1 Hz), 135.6, 135.5, 135.4, 132.9, 132.7, 132.4, 132.3, 130.2, 130.1, 129.9, 127.9, 127.8, 125.1 (d, J=34.9 Hz), 123.6 (d, J=34.2 Hz), 96.4 (d, J=182.9 Hz), 92.0 (d, J=186.6 Hz), 90.2 (d, J=36.0 Hz), 86.9 (d, J=15.1 Hz), 81.7, 79.8, 64.8, 63.0, 33.2 (d, J=20.5 Hz), 30.9 (d, J=20.4 Hz), 26.9, 26.8, 19.2; IR (thin film) 3191, 1719, 1113 cm$^{-1}$; HRMS calculated for [M+Li] C$_{25}$H$_{28}$N$_2$O$_4$SiF$_2$Li: 493.1946. Found: 493.1952. Anal. Calc. C$_{25}$H$_{28}$N$_2$O$_4$SiF$_2$: C, 61.71; H, 5.80; N, 5.76. Found: C, 61.73; H, 5.83; N, 5.77.

α-(L)-2',3'-Dideoxy-2'-fluoro-thymidine (26a). R$_f$ (100% EtOAc)=0.25; mp 147-149° C. $^1$H NMR (360 MHz, CD$_3$OD) d 7.45 (s, 1H), 6.11 (dd, J=19.4 and 2.9 Hz, 1H), 5.30 (d, J=53.6 Hz, 1H), 4.58 (m, 1H), 3.79 (dd, J=12.2 and 2.2 Hz, 1H), 3.55 (dd, J=12.2 and 3.6 Hz, 1H), 2.40-2.15 (m, 2H), 1.87 (s, 3H); $^{13}$C NMR (100 MHz, CD$_3$OD) d 166.6, 152.3, 138.6, 110.5, 93.9 (d, J=185.1 Hz), 88.3 (d, J=15.1 Hz), 81.7, 64.4, 34.5 (d, J=20.5 Hz), 12.6; IR (KBr) 3436, 3166, 1727, 1667, 1362, 1186 cm$^{-1}$; HRMS calculated for [M+Li] C$_{10}$H$_{13}$N$_2$O$_4$FLi: 251.1019. Found: 251.1014. Anal. Calc. C$_{10}$H$_{13}$N$_2$O$_4$F: C, 49.18; H, 5.37; N, 11.47. Found: C, 49.32; H, 5.40; N, 11.29.

β-(L)-2',3'-dideoxy-2'-fluoro-thymidine (26b). R$_f$ (100% EtOAc)=0.38; mp 186-188° C. $^1$H NMR (360 MHz, CD$_3$OD) d 7.94 (s, 1H), 5.93 (d, J=17.6 Hz, 1H), 5.20 (d, J=51.8 Hz, 1H), 4.40 (m, 1H), 3.98 (d, J=11.9 Hz, 1H), 3.68 (d, J=13.0 Hz, 1H), 2.37-2.10 (m, 2H), 1.83 (s, 3H); 13c NMR (100 MHz, CD$_3$OD) d 166.7, 152.3, 138.2, 111.0, 98.4 (d, J=178.3 Hz), 92.1 (d, J=36.4 Hz), 83.1, 62.4, 32.5 (d, J=20.5 Hz), 12.6; IR (KBr) 3478, 3052, 1684, 1363, 1192, 1005 cm$^{-1}$; Anal. Calc. C$_{10}$H$_{13}$N$_2$O$_4$F: C, 49.18; H, 5.37; N, 11.47. Found: C, 49.29; H, 5.44; N, 11.36.

α-(L)-2',3'-dideoxy-2'-fluoro-5-fluorouridine (27a). R$_f$ (100% EtOAc)=0.38; mp 155-157° C.). $^1$H NMR (400 MHz, CD$_3$OD) d 7.80 (d, J=6.8 Hz, 1H), 6.13 (d, J=20.0 Hz, 1H), 5.35 (d, J=54.4 Hz, 1H), 4.63 (m, 1H), 3.81 (dd, J=11.9 and 3.2 Hz, 1H), 3.58 (dd, J=12.4 and 2.0 Hz, 1H), 2.41-2.15 (m, 2H); $^{13}$C NMR (100 MHz, CD$_3$OD) d 159.6 (d, J=25.8 Hz), 150.7, 141.5 (d, J=230.6 Hz), 127.0 (d, J=34.9 Hz), 93.9 (d, J=184.3 Hz), 88.5 (d, J=15.1 Hz), 81.9, 64.3, 34.3 (d, J=20.5 Hz); IR (KBr) 3401, 3098, 1661, 1458, 1018 cm$^{-1}$; HRMS calculated for [M+Li] C$_9$H$_{10}$N$_2$O$_4$F$_2$Li: 255.0769. Found: 255.0771. Anal. Calc. C$_9$H$_{10}$N$_2$O$_4$F$_2$: C, 43.56; H, 4.06; N, 11.29. Found: C, 43.70; H, 4.17; N, 11.15.

β-(L)-2',3'-dideoxy-2'-fluoro-5-fluorouridine (27b). R$_f$ (100% EtOAc)=0.54; mp 153-156° C. $^1$HNMR (400 MHz, CD$_3$OD) d 8.46 (d, J=6.8 Hz, 1H), 5.94 (d, J=16.4 Hz, 1H), 5.25 (dd, J=51.6 and 4.0 Hz, 1H), 4.41 (m, 1H), 4.05 (dd, J=12.8 and 2.4 Hz, 1H), 3.72 (dd, J=12.4 and 2.4 Hz, 1H), 2.34-2.09 (m, 2H); $^{13}$C NMR (100 MHz, CD$_3$OD) d 159.7 (d, J=25.8 Hz), 150.7, 141.8 (d, J=230.6 Hz), 126.3 (d, J=35.7 Hz), 98.3 (d, J=184.6 Hz), 91.9 (d, J=36.4 Hz), 83.6, 61.9, 31.9 (d, J=20.5 Hz); IR (KBr) 3482, 3037, 1702, 1654, 1402, 1103 cm; HRMS calculated for [M+Li] C$_9$H$_{10}$N$_2$O$_4$F$_2$Li: 255.0769. Found: 255.0764. Anal. Calc. C$_9$H$_{10}$N$_2$O$_4$F$_2$: C, 43.56; H, 4.06; N, 11.29. Found: C, 43.59; H, 4.06; N, 11.17.

PREPARATION OF L-2'-FLUORO-2',3'-UNSATURATED NUCLEOSIDES

A second facile synthesis of unsaturated 2'-fluoronucleosides has also now been acccomplished and is described below. The synthesis involves reacting a protected pyrimidine or purine base with key intermediate 309 in the presence of a Lewis acid, as described generally in Scheme 9 below. Representative compounds made according to this synthesis are described in Tables 5-6.

Scheme 9

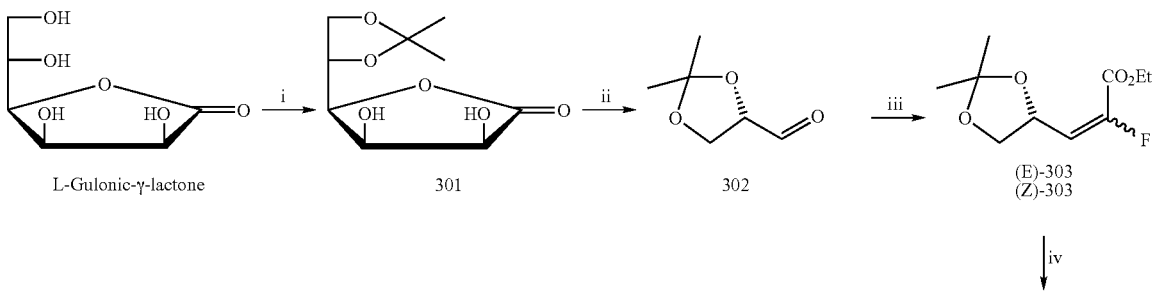

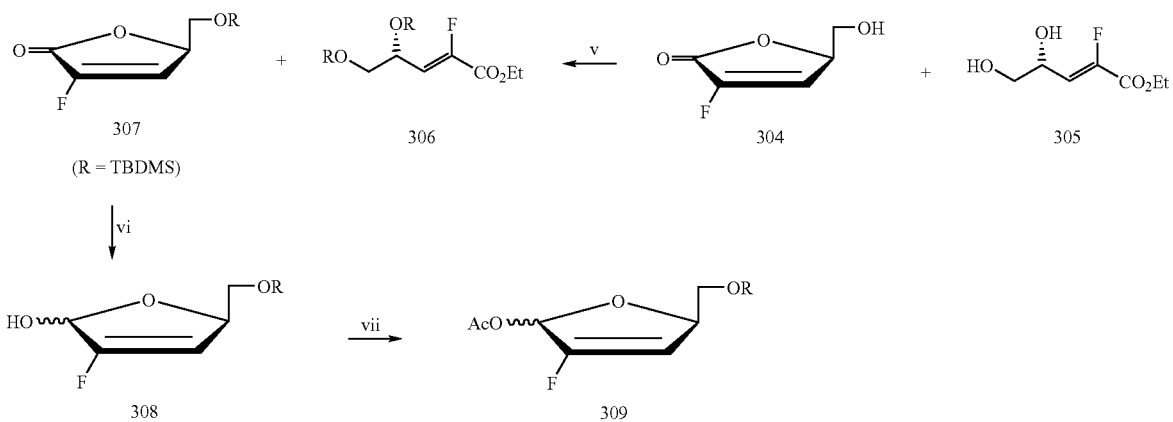

-continued

Reagents:
(i) 2-methoxypropene, DMF, p-TsOH
(ii) NaIO$_4$, H$_2$O
(iii) (EtO)$_2$P(O)CHFCO$_2$Et, NaHMDS, THF, -78° C.
(iv) c-HCl, EtOH
(v) TBDMSCl, imidazole, CH$_2$Cl$_2$
(vi) DIBAL-H, CH$_2$Cl$_2$, -78° C.
(vii) Ac$_2$O, pyridine, CH$_2$Cl$_2$.

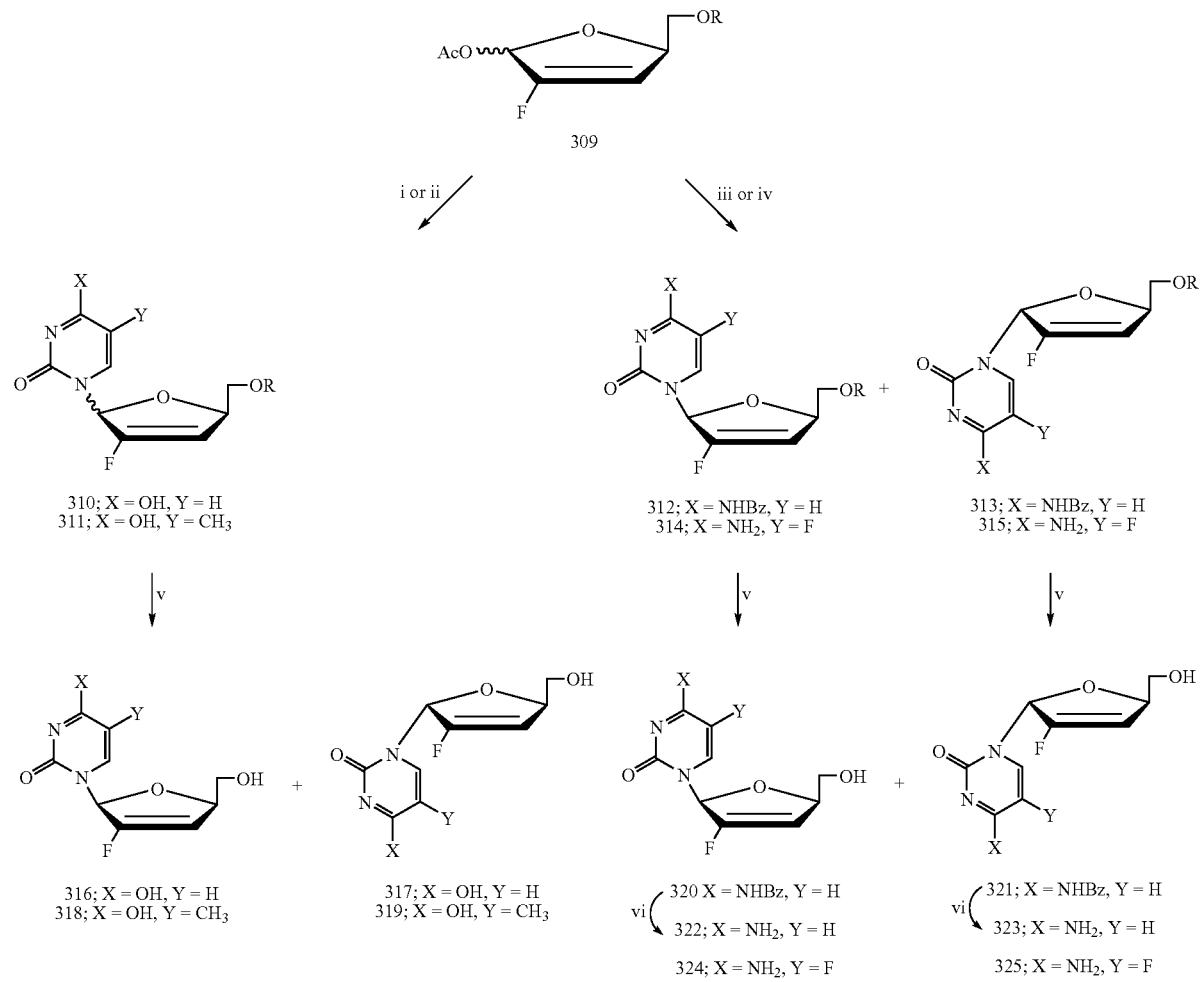

Reagents:
(i) silylated uracil, TMSOTf, DCE
(ii) silylated thymine, TMSOTf, DCE
(iii) silylated N$^4$-Bz-cytosine, TMSOTf, CH$_3$CN
(iv) 5-F-cytosine, TMSOTf, CH$_3$CN
(v) TBAF, CH$_3$CN (vi) NH$_3$/MeOH

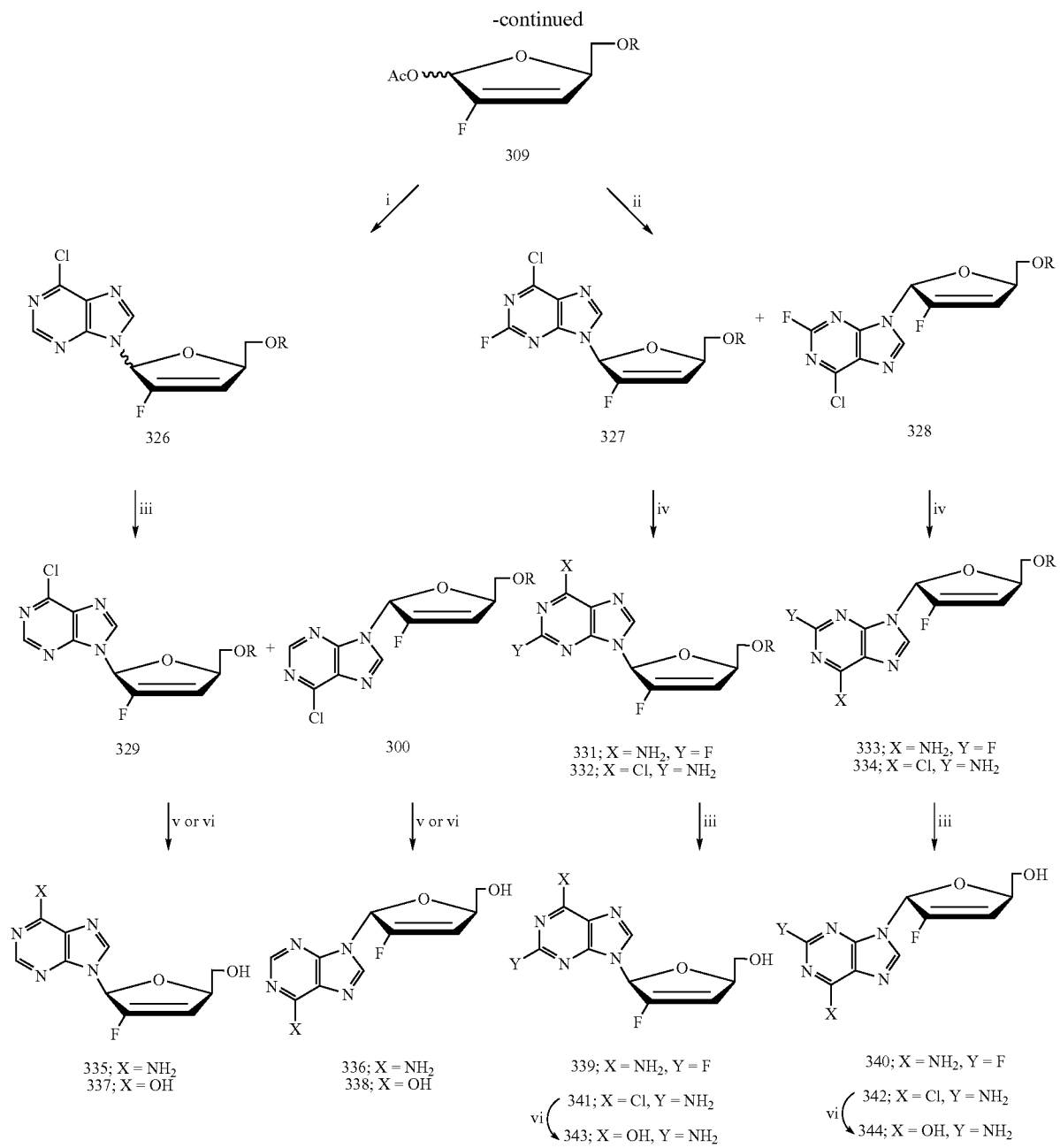
Reagents:
(i) silylated 6-Cl-purine, TMSOTf, DCE
(ii) silylated 6-Cl-2-F-purine, TMSOTf, DCE
(iii) TBAF, CH₃CN
(iv) NH₃/DME
(v) NH₃/MeOH, 90° C.
(vi) HSCH₂CH₂OH, NaOMe, MeOH, reflux.
TABLE 2
| No. | H-1' | H-3' | H-4' | H-5' | others |
|---|---|---|---|---|---|
| 10[a] | 6.88(m) | 5.72(m) | 4.97(m), 4.88(m) | 3.80(m) | 8.02(s, NH), 7.94(d, H-6, J=8Hz), 7.18(d, H-5, J=8Hz), 0.92(s, $^t$Bu), 0.90(s, $^t$Bu), 0.10, 0.09, 0.085, 0.074(4s, 4×CH₃) |
| 11[a] | 6.96(s), 6.87(m) | 5.73(s), 5.66(s) | 4.98(m), 4.84(m) | 3.76(m) | 8.15(s, NH), 7.38(s, H-6), 1.94(s, 5-CH₃), 0.92(s, $^t$Bu), 0.90(s, $^t$Bu), 0.10, 0.09, 0.085, 0.074(4s, 4×CH₃) |
| 12[a] | 7.12(s) | 5.61(s) | 4.94(s) | 3.88(m) | 8.41(d, H-6, J=7.2Hz), 7.71(m, 6H, H-5, Ph—H), 0.94(s, $^t$Bu), 0.13, 0.12 (2s, 2×CH₃) |

TABLE 2-continued

| No. | H-1' | H-3' | H-4' | H-5' | others |
|---|---|---|---|---|---|
| 13[a] | 7.08(ps t) | 5.75(s) | 5.05(ps t, j=4.4, 4.8Hz) | 3.76(m) | 7.91(d, H-6, J=6Hz), 7.57(m, 6H, H-5, Ph—H), 0.91(s, $^t$Bu), 0.09, 0.08, 0.07(3s, 2×CH$_3$) |
| 14[a] | | | | | |
| 15[a] | | | | | |
| 16[b] | 6.77(s) | 6.01(s) | 4.81(s) | 3.58(s) | 11.5(s, —NH), 7.99(d, H-6, J=8Hz), 5.71(d, H-5, J=8Hz), 5.13(t, J=5.2Hz, OH) |
| 17[b] | 6.77(t, J=4.4Hz) | 6.02(d, J=1.2Hz) | 5.02(ps t, J=4, 4.4Hz) | 3.50(m) | 11.5(s, —NH), 7.56(d, H-6, J=8Hz), 5.70(d, H-5, J=8Hz), 4.94(t, OH, J=6Hz) |
| 18[b] | 6.77(s) | 6.00(s) | 4.80(s) | 3.60(s) | 11.5(s, —NH), 7.89(s, H-6), 5.17(t, J=5.2Hz, OH), 1.76(s, 3H, CH$_3$-6) |
| 19[b] | 6.78(ps t, J=4, 4.4Hz) | 6.01(s) | 5.05(J=4Hz) | 3.51(m) | 11.5(s, —NH), 7.37(s, H-6), 4.94(t, J=6Hz, OH), 1.81(s, 3H, CH$_3$-6) |
| 20[b] | 7.01(s) | 5.71(s) | 4.99(s) | 3.88(m) | 8.21(d, J=8Hz, H-6), 7.71(m, H-5, Ph—H) |
| 21[b] | 7.16(ps t, J=3.6, 4.4Hz) | 5.74(s) | 5.13(ps t, J=3.2, 4.8Hz) | 3.79(m) | 7.92(d, J=7.2Hz, H-6), 7.57(m, H-5, Ph—H) |
| 22[b] | 6.85(s) | 5.94(d, J=1.2Hz) | 4.76(s) | 3.56(s) | 7.86(d, J=7.2Hz, H-6), 7.36, 7.32(2s, NH$_2$), 5.77(d, J=7.2Hz, H-5), 5.07 (t, J=5.2Hz, OH) |
| 23[b] | 6.86(ps t, J=4.4, 4.6Hz) | 5.94(d, J=1.6Hz)) | 4.94(m) | 3.49(m) | 7.47(d, J=7.6Hz, H-6), 7.35, 7.32(2s, NH$_2$), 5.80(d, J=7.2Hz, H-5) |

[a] CDCl$_3$,
[b] DMSO-d$^6$

TABLE 3

| No. | H-1' | H-3' | H-4' | H-5' | others |
|---|---|---|---|---|---|
| 24[a] | | | | | |
| 25[a] | | | | | |
| 26[a] | 7.01(s), 6.93(t, J=4.4Hz) | 5.85(s), 5.78(s) | 5.18(ps t, J=4, 4.4Hz), 5.02(s) | 3.85(m) | 8.79, 8.78(2s, H-8), 8.60, 8.21(2s, H-2), 1.94(s, 5-CH$_3$), 0.92, 0.91(2s, $^t$Bu), 0.111, 0.105, 0.097, 0.095(4s, 4×CH$_3$) |
| 27[a] | 6.88(s) | 5.77(s) | 5.02(s) | 3.88(m) | 8.60(s, H-8), 0.91(s, $^t$Bu), 0.112, 0.105(2s, 2×CH$_3$) |
| 28[a] | 6.81(m) | 5.84(s) | 5.19(m) | 3.81(m) | 8.17(s, H-8), 0.92(s, $^t$Bu), 0.103, 0.089(2s, 2×CH$_3$) |
| 29[a] | | | | | |
| 30[a] | 7.00(m) | 5.86(s) | 5.29(m) | 3.87(m) | 8.78(s, H-8), 8.22(s, H-2) |
| 31[a] | 6.81(m) | 5.73(d, J=1.6Hz) | 4.96(d, J=2.8Hz) | 3.85(m) | 8.19(s, H-8), 0.91(s, $^t$Bu), 0.09, 0.084(2s, 2×CH$_3$) |
| 32[a] | 6.78(m) | 5.75(s) | 4.95(m) | 3.81(m) | 8.14(s, H-8), 5.11(s, NH$_2$), 0.89(s, $^t$Bu), 0.076(s, CH$_3$) |
| 33[a] | 6.76(m) | 5.80(s) | 5.13(ps t, J=4.4, 4.8Hz) | 3.78(m) | 7.84(s, H-8), 0.91(s, $^t$Bu), 0.093, 0.08(2s, 2×CH$_3$) |
| 34[a] | 6.73(ps t, J=4.4, 4.8Hz) | 5.80(s) | 5.09(m) | 3.78(m) | 7.84(s, H-8), 5.12(s, NH$_2$), 0.91(s, $^t$Bu), 0.096, 0.082(s, CH$_3$) |
| 35[b] | 6.90(s) | 6.08(s) | 4.91(s) | 3.63(s) | 8.40(s, H-8), 8.17(s, H-2), 7.40(s, NH$_2$), 5.22(t, J=5.6Hz, OH) |
| 36[b] | 6.89(t, J=4Hz) | 6.06(s) | 5.14(ps t, J=3.6, 4Hz) | 3.57(m) | 8.31(s, H-8), 8.17(s, H-2), 7.36(s, NH$_2$), 4.97(t, J=6Hz, OH) |
| 37[b] | 6.94(m) | 6.15(t, J=1.6Hz) | 4.98(s) | 3.67(s) | 12.57(br s, NH), 8.43(s, H-8), 8.17(s, H-2), 5.17(s, OH) |
| 38[b] | 6.87(ps t, J=3.6, 4.4Hz) | 6.06(s) | 5.13(t, J=3.6Hz) | 3.56(m) | 8.26(s, H-8), 8.09(s, H-2) |

[a] CDCl$_3$,
[b] DMSO-d$^6$

TABLE 4

| No. | H-1' | H-3' | H-4' | H-5' | others |
|---|---|---|---|---|---|
| 39[b] | 6.80(s) | 6.09(ps t, J=1.2, 1.6Hz) | 4.90(s) | 3.62(m) | 8.38(s, H-8), 7.99, 7.92(2br s, NH$_2$), 5.09(t, J=5.6Hz, OH) |
| 40[b] | 6.82(m) | 6.07(d, J=1.2Hz) | 5.12(m) | 3.56(m) | 8.30(s, H-8), 7.96(2s, NH$_2$) |
| 41[b] | 6.76(s) | 6.09(s) | 4.91(s) | 3.60(s) | 8.38(s, H-8), 7.07(s, NH$_2$), 5.10(s, OH) |
| 42[b] | 6.72(t, J=4Hz) | 6.06(d, J=1.2Hz) | 5.16(ps t, J=3.6, 4Hz) | 3.60(m) | 8.30(s, H-8), 7.04(s, NH$_2$), 4.98(t, J=6Hz, OH) |
| 43[b] | 6.60(s) | 6.03(d, J=1.2Hz) | 4.86(s) | 3.59(s) | 10.74(br s, NH), 8.96(s, H-8), 6.57(s, NH$_2$), 5.08(t, J=5.2Hz, OH) |
| 44[b] | 6.62(m) | 6.01(d, J=1.6Hz) | 5.08(m) | 3.56(m) | 7.82(s, H-8), 6.57(s, NH$_2$), 4.95(t, J=5.6Hz, OH) |

[b] DMSO-d$^6$

TABLE 5

| no. | mp ° C.(solv)[a] | [α]$_D$, deg | formula | anal. |
|---|---|---|---|---|
| 10 | syrup | | C$_{15}$H$_{23}$FN$_2$O$_4$Si | C, H, N |
| 11 | syrup | | C$_{16}$H$_{25}$FN$_2$O$_4$Si | C, H, N |
| 12 | 144-146(A) | −20.47 (c 0.36, CHCl$_3$) | C$_{22}$H$_{28}$FN$_3$O$_4$Si | C, H, N |

TABLE 5-continued

| no. | mp °C.(solv)[a] | $[\alpha]_D$, deg | formula | anal. |
|---|---|---|---|---|
| 13 | 139-141 (A) | +157.68 (c.0.31, CHCl$_3$) | C$_{22}$H$_{28}$FN$_3$O$_4$Si | C, H, N |
| 14 | syrup | | | C, H, N |
| 15 | syrup | | | C, H, N |
| 16 | 161-162 (C) | −13.412 (c 0.20, MeOH) | C$_9$H$_9$FN$_2$O$_4$ 0.3H$_2$O | C, H, N |
| 17 | 136-137 (E) | +138.55 (c 0.14, MeOH) | C$_9$H$_9$FN$_2$O$_4$ 0.2H$_2$O | C, H, N |
| 18 | 149-151 (D) | −30.44 (c 0.20, MeOH) | C$_{16}$H$_{15}$FN$_2$O$_5$ | C, H, N |
| 19 | 116-118 (E) | +132.42 (c 025, MeOH) | C$_{16}$H$_{13}$FN$_2$O$_5$ | C, H, N |
| 20 | 200-202-dec (C) | −54.89 (c 0.39, CHCl$_3$) | C$_{16}$H$_{14}$FN$_3$O$_4$ | C, H, N |
| 21 | 170-172 (C) | +136.38 (c 0.45, CHCl$_3$) | C$_{16}$H$_{14}$FN$_3$O$_4$ 0.3H$_2$O | C, H, N |
| 22 | 198-200 dec (B) | −21.31 (c 025, MeOH) | C$_9$H$_{10}$FN$_3$O$_3$ 4H$_2$O | C, H, N |
| 23 | 120-121 (E) | +159.15 (c 021, MeOH) | C$_9$H$_{10}$FN$_3$O$_3$ | C, H, N |
| 24 | syrup | | | C, H, N |
| 25 | syrup | | | C, H, N |
| 26 | syrup | | C$_{16}$H$_{22}$FClN$_5$O$_2$Si | C, H, N |
| 27 | foam | +9.80 (c 0.20, CHCl$_3$) | C$_{16}$H$_{21}$F$_2$ClN$_4$O$_2$Si | C, H, N |
| 28 | syrup | +139.67 (c 0.18, CHCl$_3$) | C$_{16}$H$_{21}$F$_2$ClN$_4$O$_2$Si | C, H, N |
| 29 | | | | C, H, N |
| 30 | foam | | | C, H, N |
| 31 | 180-182 (A) | +13.33 (c 054, CHCl$_3$) | C$_{16}$H$_{23}$F$_2$N$_5$O$_2$Si 0.2aceton | C, H, N |
| 32 | 129-130 (A) | +90.22 (c 0.23, CHCl$_3$) | C$_{16}$H$_{23}$FClN$_5$O$_2$Si | C, H, N |
| 33 | 184-186 (A) | +116.53 (c 0.13, CHCl$_3$) | C$_{16}$H$_{23}$F$_2$N$_5$O$_2$Si 0.3aceton | C, H, N |
| 34 | 128-130 (A) | +89.87 (c 0.15, CHCl$_3$) | C$_{16}$H$_{23}$FClN$_5$O$_2$Si | C, H, N |
| 35 | 188-189 (C) | −54.91 (c 0.17, MeOH) | C$_{10}$H$_{10}$FN$_5$O$_2$ 0.2H$_2$O | C, H, N |
| 36 | 169-171 (C) | +160.62 (c 0.19, MeOH) | C$_{10}$H$_{10}$FN$_5$O$_2$ 0.3MeOH | C, H, N |
| 37 | 128-130 (E) | −50.21 (c 0.20, MeOH) | C$_{10}$H$_9$FN$_4$O$_3$ 0.2H$_2$O | C, H, N |
| 38 | >200 dec (C) | +169.60 (c 0.20, MeOH) | C$_{10}$H$_9$FN$_4$O$_3$ 0.3H$_2$O | C, H, N |
| 39 | 185-188 dec (B) | −56.15 (c 0.16, MeOH) | | C, H, N |
| 40 | 180 dec (B) | +178.22 (c 0.10, MeOH) | | C, H, N |
| 41 | 155-156 dec (B) | +10.64 (c 0.17, MeOH) | | C, H, N |
| 42 | 150-152 (B) | +142.49 (c 0.17, MeOH) | | C, H, N |
| 43 | >200 dec (B) | +24.42 (c 0.10, DMF) | | C, H, N |
| 44 | >210 dec (B) | +58.68 (c 0.10, DMF) | | C, H, N |

[a]Solvents; A; EtOAc-hexanes, B; CH$_2$Cl$_2$—MeOH, C; CHCl$_3$—MeOH, D; THF-cyclohexane, E; lyophilyzed Previously, the synthesis of 2',3'-unsaturated D-nucleosides has been accomplished via eleimination reaction starting from readily available nucleoside analog, which involved a lengthy modification for individual nucleosides. Several groups reported D-2'-fluoro-2',3'-unsaturated pyrimidine nucleosides by the elimination of suitable 2'-fluorinated nucleoside analogs (Martin, J. A., et al., *J. Med. Chem.* 1990, 33, 2137-2145; Stezycki, R. Z., et al., *J. Med. Chem.* 1990, 33, 2150-2157). This strategy for the synthesis of L-Fd4N, however, is accompanied by additional difficulties in the preparation of L-nucleosides as the starting material. There are few examples of the synthesis of 2',3'-unsaturated purine nucleosides by direct condensation due to the lability of the 2,3-unsaturated sugar moiety under the coupling conditions in the presence of Lewis acid, except one case of the pyrimidine analog using a thiophenyl intermediate (Abdel-Medied, A. W.-S., et al., *Synthesis* 1991, 313-317; Sujino, K., et al., *Tetrahedron Lett.* 1996, 37, 6133-6136). In contrast to the 2,3-unsaturated sugar moiety, the 2-fluoro-2,3-unsaturated sugar, which bears enhanced stability of glycosyl bond during the condensation with a heterocycle, was expected to become more suitable for the direct coupling reaction. Thus, (R)-2-fluorobutenolide 506, as a precusor for the key intermediate 508, was chosen, which was prepared from L-glyceraldehyde acetonide 501.

Starting from L-glyceraldehyde acetonide, a mixture of the (E)-502/(Z)-2 (9:1 by $^1$H NMR) was obtained via the Horner-Emmons reaction in the presence of triethyl α-fluorophosphonoacetate and sodium bis(trimethylsilyl)amide in THF (Thenappan, A., et al., *J. Org. Chem.,* 1990, 55, 4639-4642; Morikawa, T., et al., *Chem. Pharm. Bull.* 1992, 40, 3189-3193; Patrick, T. B., et al., *J. Org. Chem.* 1994, 59, 1210-1212). Due to the difficulties in separating (E)-502/(Z)-502 isomers, the mixtures were used in the following cyclization reaction under acidic condition to give the desired lactone 503 and uncyclized diol 504. The resulting mixture was converted to the silyl lactone 506 was subjected to reduction with DIBAL-H in CH$_2$Cl$_2$ at 78° C. to give the lactol 507. The lactol 507 was treated with acetic anhydride to yield key intermediate 508, which was condensed with silylated 6-chloropurine under Vorburggen conditions to afford anomeric mixtures 509. Treatment of 509 with TBAF in THF gave free nucleosides 510 and 511, which was readily separated by silica gel column chromatography. Adenine analogs 512 and 513 were obtained by the treatment of compound 510 and 511 with mercaptoethanol and NaOMe a steel bomb at 90° C., respectively. Treatment of compounds 510 and 511 with mercaptoethanol and NaOMe afforded the inosine analogs 514 and 515, respectively. The sterochemical assignment of these compounds was based on th NOESY spectroscopy (cross peak between H-1' and H4' in B-isomer 512).

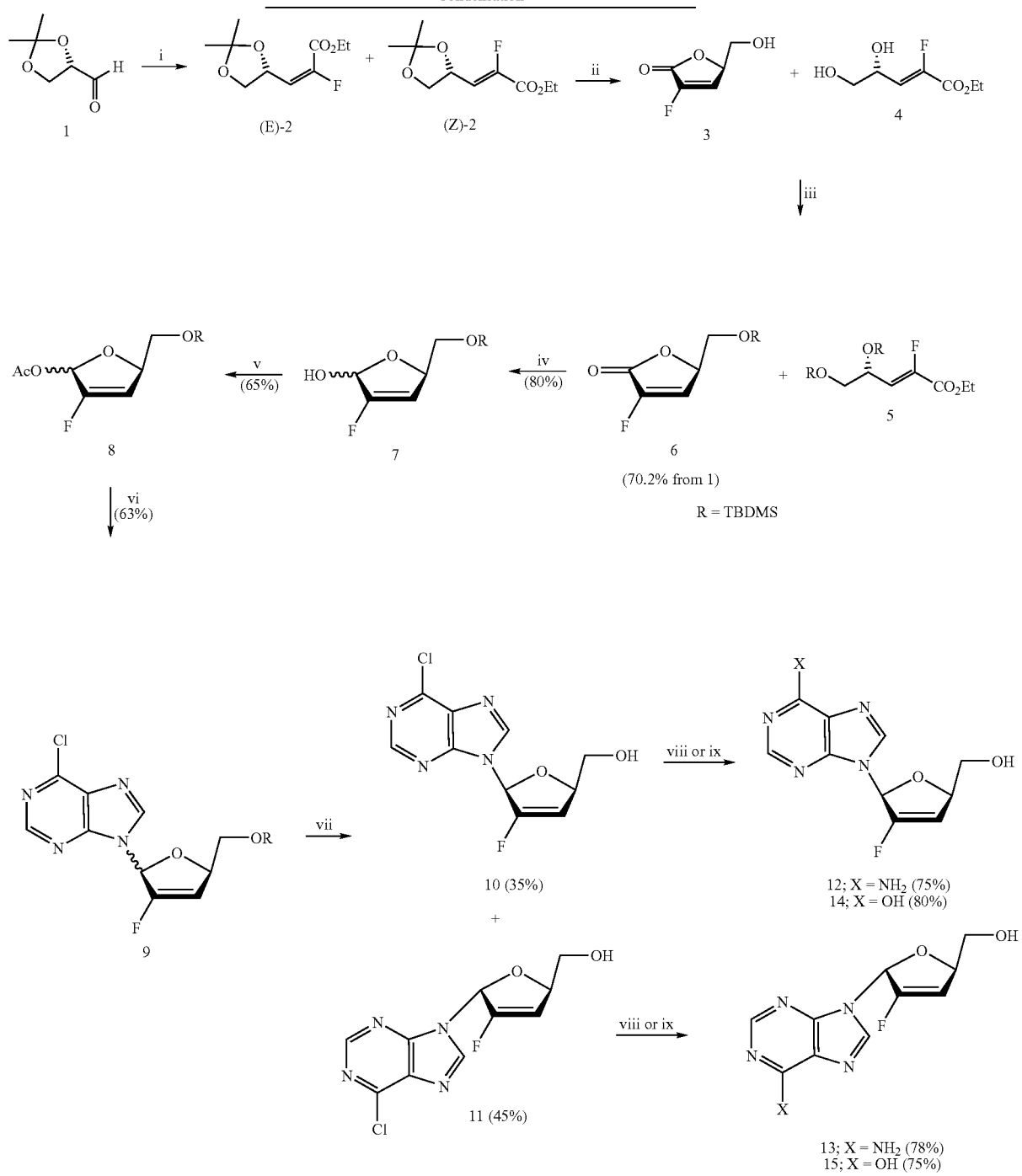
Scheme 10.
Synthesis of L-2′-Fluoro-d4Adenine and -Hypoxanthine by Direct Condensation
Reagents:
(i) (EtO)$_2$P(O)CHFCO$_2$Et, [(CH$_3$)$_3$Si]$_2$NNa, THF, -78° C.
(ii) HCl/EtOH
(iii) TBDMSCl, imidazole, CH$_2$Cl$_2$
(iv) 1 M DIBAL-H in CH$_2$Cl$_2$, CH$_2$Cl$_2$, -78° C.
(v) Ac$_2$O, pyr., CH$_2$Cl$_2$ (vi) silylated 6-Cl-purine, TMSOTf, DCE
(vii) TBAF, CH$_3$CN
(viii) NH$_3$/MeOH, 90° C.
(ix) HS(CH$_2$)$_2$OH, NaOMe/MeOH, reflux

TABLE 7

Median Effective (EC$_{50}$) and Inhibitory (IC$^{50}$) Concentration of L-2'-Fluoro-d4Adenine and Hypoxanthine against HIV-1 in PBM

| Compound No. | EC$_{50}$ (μM) (PBM Cells) | EC$_{90}$ (μM) (PBM Cells) | Cytotoxicity | | |
|---|---|---|---|---|---|
| | | | PMC Cells IC$_{50}$ (μM) | Vero Cells IC$_{50}$ (μM) | CEM Cells IC$_{50}$ (μM) |
| 512 | 1.5 | 15.1 | >100 | >100 | >100 |
| 513 | 47.6 | 332 | >100 | >100 | >100 |
| 514 | >100 | >100 | >100 | >100 | >100 |
| 515 | >100 | >100 | >100 | >100 | >100 |
| 316 (β) | >100 | >100 | >100 | >100 | >100 |
| 317 (α) | >100 | >100 | >100 | >100 | >100 |
| 318 (β) | >100 | >100 | >100 | >100 | >100 |
| 319 (α) | >100 | >100 | >100 | >100 | >100 |
| 322 (β) | 0.51 | 4.3 | >100 | >100 | >100 |
| 323 (α) | >100 | >100 | >100 | >100 | >100 |
| 335 (β) | 1.5 | 15.1 | >100 | >100 | >100 |
| 336 (α) | 47.6 | 332 | >100 | >100 | >100 |
| 337 (β) | >100 | >100 | >100 | >100 | >100 |
| 338 (α) | >100 | >100 | >100 | | >100 |
| AZT | 0.004 | 0.04 | >100 | 29.0 | 14.3 |

EXPERIMENTAL SECTION

Melting points were determined on a Mel-temp II laboratory device and are uncorrected. Nuclear magnetic resonance spectra were recorded on a Bruker 250 and AMX400 400 MHz spectrometers with tetramethylsilane as the internal reference; chemical shifts (δ) are reported in parts per million (ppm), and the signals are described as s (singlet), d (doublet), t (triplet), q (quartet), br s (broad singlet), dd (doublet of doublet), and m (multiplet). UV spectra were obtained on a Beckman DU 650 spectrophotometer. Optical rotations were measured on a Jasco DIP-370 Digital Polarimeter. Mass spectra were measured on a Micromass Inc. Autospec High Resolution double focussing sector (EBE) MS spectrometers. Infrared spectra were recorded on a Nicolet 510 FT-IR spectrometer. Elemental analyses were performed by Atlantic Microlab, Inc., Norcross, Ga. All reactions were monitored using thin layer chromatography on Analtech, 200 mm silica gel GF plates. Dry 1,2-dichloroethane, dichloromethane, and acetonitrile were obtained by distillation from CaH$_2$ prior to use. Dry THF was obtained by distillation from Na and benzophenone when the solution became purple.

L(S)-Glyceraldehyde acetonide (302). A solution of L-gulonic-γ-lactone (175 g, 0.98 mol) in DMF (1 L) was cooled to 0° C. and p-toluenesulfonic acid (1.1 g, 5.65 mmol) was added portionwise with stirring. To the resulting solution, 2-methoxypropene (87.7 g, 0.92 mol) was added dropwise through a dropping funnel at 0° C. The reaction mixture was warmed up to room temperature and further stirred for 24 h. After the completion of the reaction, sodium carbonate (124 g) was added and the resulting suspension was vigorously stirred for 3 hours. It is then filtered over glass filter and the filtrate is evaporated under vacuum. To the yellow residue, toluene (170 mL) is added whereupon crystallization occurred. The solid was filtered by suction, washed with hexanes/ethanol (9:1; 1 L), and dried to give yellowish solid 301 (99.1 g, 65%).

To a stirred suspension of 5,6-O-isopropylidene-L-gulono-1,4-lactone (70.0 g, 0.32 mol) in water (270 mL), sodium metaperiodate (123 g, 0.58 mol) was added portionwise at 0° C. over 30 min maintaining pH 5.5 (adjusted by addition of 2 N NaOH). The suspension was stirred at room temperature for 2 hours, then saturated with sodium chloride and filtered. The pH of the filtrate was adjusted to 6.5-7.0 and extracted with dichloromethane (5 times 200 mL) and ethyl acetate (5 times 300 mL). The combined organic layer were dried with anhydrous magnesium sulfate, filtered and concentrated under reduced pressure (<20° C.). And then the resulting residue was distilled to give 302 (23.2 g, 69%) as a colorless oil; b.p. 49-51° C./16 Torr. [α]$_D$25-66.4 (c 6.3, benzene).

(E)/(Z)-Ethyl-3-[(R)-2,2-dimethyl-1,3-dioxolan-4-yl]-2-fluoroacrylate (E-303 and Z-303). A solution of triethyl 2-fluorophosphonoacetate (39.2 g, 162 mmol) in THF (70 mL) was cooled to −78° C. and a solution of sodium bis(trimethylsilyl)amide (1.0 M solution in THE, 162 mL, 162 mmol) was added dropwise. The mixture was kept for 30 min at −78° C., then a solution of 303 (19.14 g, 147 mmol) in THF (70 mL) was added. After being stirred for 1 h at −78° C., the reaction mixture was treated with aqueous NH$_4$Cl and extracted with ether. The ether phase was washed with saturated NaCl, dried over MgSO$_4$, filtered and evaporated. The residue was chromatographed on silica gel to give E-303 and Z-303 (9:1 by $^1$H NMR) as a pale yellowish oil (34.6 g, 97.9%). $^1$H NMR (CDCl$_3$) δ 1.34, 1.36 (2t, J=8 Hz, —CH$_2$CH$_3$), 1.40, 1.45 (2s, —CH$_3$), 3.69 (m, H$_a$-5), 4.28 (m, H$_b$-5, —CH$_2$CH$_3$), 5.02 (m, H-4), 5.40 (m, H-4), 6.02 (dd, J=8, 20 Hz, H-3), 6.18 (dd, J=8, 32 Hz, H-3).

(R)-(+)-4-[(tert-Butyldimethylsilyloxy)methyl]-2-fluoro-2-buten-4-olide (307). A solution of E-303 and Z-303 (19.62 g, 89.89 mmol) in 110 mL of anhydrous EtOH was treated with 30 mL of conc. HCl and stirred at room temperature for 2 hr. The solvent was removed in vacuo and the residue was coevaporated with Toluene (3*300 mL) to give the lactone 304 and uncyclized ester 305. The resulting yellowish syrup was used for next reaction without further purification. t-Butyldimethylsilyl chloride (27.1 g, 180 mmol) was added to a mixture of 304, 305 and imidazole (12.3 g, 180 mmol) in CH$_2$Cl$_2$ (250 mL) and the reaction mixture was stirred for 4 h at room temperature. The resulting mixture was washed with water, dried (MgSO$_4$), filtered and concentrated to dryness. The residue was isolated by silica gel column chromatography using 4% EtOAc-hexanes as an eluent to give 307 (28.0 g, 70.2% from compound 302) as a white crystalline solid. mp 48-50° C.; [α]$^{28}_D$+105.3 (c 1.60, CHCl$_3$); $^1$H NMR (CDCl$_3$) δ 0.07, 0.08 (2s, 2×CH$_3$), 0.88 (s, $^t$Bu), 3.88 (m, 2H, H-5), 5.01 (m, 1H, H-4), 6.73 (ps t, 1H, J=4 Hz); Anal. Calcd for C$_{10}$H$_{19}$FO$_3$Si: C, 53.63; H, 7.77. Found: C, 53.70; H, 7.75.

1-Acetyl-4-[(tert-butyldimethylsilyloxy)methyl]-2-fluoro-2-buten-4-olide (309). Lactone 307 (20.58 g, 83.54 mmol) was dissolved in 200 mL of CH$_2$Cl$_2$ under nitrogen atmosphere, then the mixcture was cooled to −78° C. and 1.0 M solution of DIBAL-H in CH$_2$Cl$_2$ (125 mL) was added. The resulting mixture was stirred for 2 hours at −78° C. The cold mixture was treated with dilute nitric acid, washed with water, and dried (Na$_2$SO$_4$). Evaporation of the solvent gave anomers of 308 as a pale yellow oil (16.6 g, crude yield 80%), which was used for the next step without further purification.

Ac$_2$O (25 mL, 0.27 mol) was added to a solution of 308 and pyridine (22 mL, 0.27 mol) in CH$_2$Cl$_2$ (200 mL) at 0° C. and the resulting mixture was stirred for 16 hours. The reaction mixture was washed with dilute HCl, saturated NaHCO$_3$ solution, and brine. The combined organic layer was dried, filtered, and concentrated to dryness. The residue was column chromatographed (6.5% EtOAc/hexanes) to give 309 (12.6 g, 65%) as a colorless oil.

General Procedure for Condensation of Acetate 309 with Pyrimidine Bases.

A mixture of uracil (420 mg, 3.75 mmol), hexamethyldisilazane (15 mL) and ammonium sulfate (20 mg) was refluxed for 3 hours under nitrogen. The clear solution obtained was concentrated to dryness in vacuo. TMSOTf (0.7 mL, 3.14 mmol) were added to the solution of sugar 309 (728 mg, 2.50 mmol)) and the silylated base in dry DCE (20 mL) at 0° C. The reaction mixture was stirred for 2 hours under nitrogen, poured into a cooled sat. $NaHCO_3$ solution (30 mL) and stirred for 15 min. The resulting mixture was washed, dried ($Na_2SO_4$), filtered, and concentrated in vacuo. The crude product was purified by column chromatography (3% $MeOH/CHCl_3$) to give 310 (0.960 g, 2.73 mmol, 73%) as an inseparable anomeric mixture, which was used in the next step without separation.

1[5-O-(tert-Butyldimethylsilyl)-2,3-dideoxy-2-fluoro-L-gycero-pent-2enofuranosyl]uracil (310).

UV ($CHCl_3$) $\lambda_{max}$ 257.5 nm.; Anal. ($C_{15}H_{23}FN_2O_4Si$) C, H, N.

1-[5-O-(tert-Butyldimethylsilyl)-2,3-dideoxy-2-fluoro-L-gycero-pent-2-enofuranosyl]thymine (311).

Silylated thymine (242 mg, 1.92 mmol), 307 (500 mg, 1.72 mmol), and TMSOTf (0.5 mL, 2.25 mmol) were reacted for 2 h to give a mixture of 311, which was purified by silica gel column chromatography (3% $MeOH/CHCl_3$) as an inseparable anomeric mixture (0.392 g, 1.10 mmol, 64%). UV ($CHCl_3$) $\lambda_{max}$ 262.0 nm. Anal.($C_{16}H_{25}FN_2O_4Si$) C, H, N.

$N^6$-Benzoyl-1-[5-O-(tert-butyldimethylsilyl)-2,3-dideoxy-2-fluoro-(a,b)-L-glycero-pent-2-enofuranosyl]cytosine (312 and 313).

Silylated $N^6$-benzoyl cytosine (790 mg, 3.67 mmol), 307 (470 mg, 1.62 mmol), and TMSOTf (0.5 mL, 2.25 mmol) were reacted for 2 h to give mixtures of 312 and 313, which were purified by silica gel column (30% EtOAc/hexane) to afford β anomer 312 (0.34 g, 0.76 mmol, 47.1%) as a white solid and α anomer 313 chromatography (0.23 g, 0.52 mmol, 31.8%) as a white solid. 312: WV ($CHCl_3$) $\lambda_{max}$ 260.5 nm; Anal. ($C_{22}H_{28}FN_3O_4Si$) C, H, N.; 513: UV ($CHCl_3$) $\lambda_{max}$ 260.5 nm.; Anal. ($C22H_{28}FN_3O_4Si$) C, H, N.

5-Fluoro-1-[5-O-(tert-butyldimethylsilyl)-2,3-dideoxy-2-fluoro-(a,b-L-glycero-pent-2-enofuranosyl]cytosine (314 and 315).

Silylated 5-fluoro-cytosine (300 mg, 2.32 mmol), 309 (360 mg, 1.24 mmol), and TMSOTf (0.4 mL, 1.86 mmol) were reacted for 2 h to give a mixture of 314 and 315, which was purified by silica gel column chromatography (3% $MeOH/CH_2Cl_2$) to afford β anomer 314 as a white solid (168 mg, 37.8%) and α anomer 315 (121 mg, 27.1%) as a white solid. 314: UV (MeOH) $\lambda_{max}$ 281.5 nm; 315: UV (MeOH) $\lambda_{max}$ 281.5 nm.

1-(2,3-Dideoxy-2-fluoro-(α,β)-L-gycero-pent-2-eno-furanosyl)uracil (316 and 317).

Tetra-n-butylammonium fluoride (0.6 mL, 0.6 mmol) was added to a mixture of 310 (177 mg, 0.52 mmol) in THF. (15 mL) and the reaction mixture was stirred at room temperature for 15 min. The solvent was removed and the residue was purified by silica gel column chromatography (2% $MeOH/CHCl_3$) to give β anomer 316 (52.8 mg, 0.23 mmol, 44.5%) and α anomer 317 (35.1 mg, 0.15 mmol, 29.6%).

316: UV ($H_2O$) $\lambda_{max}$ 261.0 nm (pH 7); Anal. ($C_9H_9FN_2O_4.0.3H_2O$) C, H, N. 317: UV ($H_2O$) $\lambda_{max}$ 261.0 nm (pH 7); Anal. ($C_9H_9FN_2O_4.0.2H_2O$) C, H, N.

1-(2,3-Dideoxy-2-fluoro-(α,β)-L-gycero-pent-2-eno-furanosyl)thymine (318 and 319).

Tetra-n-butylammonium fluoride (0.8 mL, 0.8 mmol) was added to a mixture of 311 (240 mg, 0.67 mmol) in THF (10 mL) at 0° C. and the reaction mixture was stirred at room temperature at rt for 15 min. The solvent was removed and the residue was purified by silica gel column chromatography (40% THF/cyclohexane) to give β anomer 318 (66.5 mg, 0.28 mmol, 41%) and α anomer 319 (52.8 mg, 0.23 mmol, 26%).

318: UV ($H_2O$) $\lambda_{max}$ 265.5 nm (pH 7); Anal. ($C_{10}H_{11}FN_2O_4.0.4H_2O$) C, H, N. 319:UV ($H_2O$) $\lambda_{max}$ 266.0 nm (pH 7); Anal. ($C_9H_9FN_2O_4.0.3H_2O$) C, H, N.

$N^6$-Benzoyl-1-(2,3-dideoxy-2-fluoro-β-L-gycero-pent-2-enofuranosyl)cytosine (320).

Tetra-n-butylammonium fluoride (1M in THF) (1 mL, 1 mmol) was added to a solution of the β anomer 312 (280 mg, 0.63 mmol) in THF (10 mL) and the reaction was allowed to stir at room temperature for 1 h. The reaction mixture was concentrated under the reduced pressure and the residue was purified by flash silica gel column using 2.5% $MeOH/CHCl_3$ to give 320 (218 mg, 0.66 mmol, 75%) as a white solid.

UV (MeOH) $\lambda_{max}$ 260.5 nm. Anal. ($C_{16}H_{14}FN_3O_4$) C, H, N.

$N^6$-Benzoyl-1-(2,3-dideoxy-2-fluoro-α-L-gycero-pent-2-enofuranosyl)cytosine (321).

Tetra-n-butylammonium fluoride (1M in THF) (1 mL, 1 mmol) was added to a solution of the α anomer 313 (280 mg, 0.63 mmol) in THF (10 mL) and the reaction was allowed to stir at room temperature for 1 h. The reaction mixture was concentrated under the reduced pressure and the residue was purified by silica gel column chromatography using 2.5% $MeOH/CHCl_3$ to give 321 (145.8 mg, 0.44 mmol, 69%) as a white solid.

UV (MeOH) $\lambda_{max}$ 260.5 nm. Anal. ($C_{16}H14FN_3O_4.0.3H_2O$) C, H, N.

1-(2,3-dideoxy-2-fluoro-β-L-gycero-pent-2-enofuranosyl)cytosine (322). A solution of the β anomer (67.60 mg, 0.204 mmol) in MeOH (5 mL) was treated with $NH_3$/MeOH (10 mL saturated solution) and the reaction mixture was allowed to stir at room temperature until the disappearance of starting material was observed (10 h). The reaction mixture was concentrated under reduced pressure and the residue was purified by preparative TLC using 12% MeOH/ $CH_2Cl_2$ as an eluent. The material obtained from the plate gave 322 (43 mg, 93.1%) as a solid on trituration with hexanes and diethylether.

UV ($H_2O$) $\lambda_{max}$ 266.5 nm (pH 7); Anal. ($C_9H_{10}FN_3O_3.0.4H_2O$) C, H, N.

1-(2,3-dideoxy-2-fluoro-α-L-gycero-pent-2-enofuranosyl)cytosine (323). A solution of the α anomer (65.90 mg, 0.199 mmol) in MeOH (5 mL) was treated with $NH_3$/MeOH (10 mL saturated solution) and the reaction mixture was allowed to stir at room temperature until the disappearance of starting material was observed (16 h). The reaction mixture was concentrated under reduced pressure and the residue was purified by preparative TLC using 12% MeOH/ $CH_2Cl_2$ as an eluent. The material obtained from the plate gave 322 (42.5 mg, 94.5%) as a solid on trituration with hexanes and diethylether.

UV ($H_2O$) $\lambda_{max}$ 276.0 nm (pH 2), 267.0 nm (pH 7); Anal. ($C_9H_{10}FN_3O_3$) C, H, N.

5-Fluoro-1-(2,3-dideoxy-2-fluoro-β-L-gycero-pent-2-eno-furanosyl)cytosine (324).

Tetra-n-butylammonium fluoride (1M in THF) was added to a solution of the β anomer 314 in acetonitrile and the reaction was allowed to stir at room temperature for 1 h. The reaction mixture was concentrated under the reduced pressure and the residue was purified by flash silica gel column using 12% MeOH/CHCl$_3$ to give 324.

5-Fluoro-1-(2,3-dideoxy-2-fluoro-α-L-gycero-pent-2-enofuranosyl)cytosine (325).

Tetra-n-butylammonium fluoride (1M in THF) was added to a solution of the β anomer 315 in acetonitrile and the reaction was allowed to stir at room temperature for 1 h. The reaction mixture was concentrated under the reduced pressure and the residue was purified by flash silica gel column using 12% MeOH/CHCl$_3$ to give 325.

General Procedure for Condensation of Acetate 309 with Purine Bases.

A mixture of 6-chloropurine (1.20 g, 7.75 mmol), hexamethyldisilazane (25 mL) and ammonium sulfate (catalytic amount) was refluxed for 4 h under nitrogen. The clear solution was obtained was concentrated in vacuo and the residue was dissolved in dry DCE (10 mL) and reacted with a solution of 307 (1.50 g, 5.17 mmol) in DCE (40 mL) and trimethylsilyl triflate (1.5 mL, 7.75 mmol) at room temperature. After stirring the mixture for 1 h at room temperature under nitrogen, the reaction solution was then poured into an ice cold saturated NaHCO$_3$ solution (20 mL) and stirred for 15 min. The organic layer was washed with water and brine, and dried over MgSO$_4$. The solvents were removed under reduced pressure and the residue was separated by silica gel column chromatography using 12.5% EtOAc/hexanes to give anomeric mixture 326 (1.25 g, 62.9%) as a syrup.

6-Chloro-9-[5-O-(tert-butyldimethylsilyl)-2,3-dideoxy-2-fluoro-L-gycero-pent-2-enofuranosyl]purine (326)

326: UV (MeOH) $\lambda_{max}$ 265.0 nm; Anal. (C$_{16}$H$_{22}$ClFN$_4$O$_2$Si) C, H, N.

6-Chloro-2-fluoro-9-[5-O-(tert-butyldimethylsilyl)-2,3-dideoxy-2-fluoro-(α,β) -L-gycero-pent-2-enofuranosyl]purine (327 and 328).

A mixture of silylated 2-fluoro-6-chloropurine [prepared from 1.170 g (6.78 mmol) of 2-fluoro-6-chloropurine and dry DCE (40 mL) was stirred for 16 h at room temperature. After work-up similar to that of 326, purification by silica gel column chromatography (12% EtOAc/hexanes) gave β anomer 327 (685 mg, 1.70 mmol, 30.0%) as a white foam and α anomer 328 (502 mg, 1.25 mmol, 22.1%) as an yellowish syrup.

327: UV (MeOH) $\lambda_{max}$ 268.5 nm. Anal. (C$_{16}$H$_{21}$F$_2$Cl N$_4$O$_2$Si) C, H, N., 328: UV (MeOH) $\lambda_{max}$ 269.0 nm. Anal. (C$_{16}$H$_{21}$F$_2$Cl N$_4$O$_2$Si) C, H, N.

6-Chloro-9-(2,3-dideoxy-2-fluoro-(α,β)-L-gycero-pent-2-enofuranosyl)purine (329 and 330). A solution of 326 (1.2 g, 3.12 mmol) in dry CH$_3$CN (20 mL) was treated with TBAF (1 M solution in THF) (3.2 mL, 3.2 mmol) and stirred for 1 h. After evaporation of solvent, the dryness was purified by column chromatography (3% MeOH/CHCl$_3$) to obtain β anomer 329 (296 mg, 35%) as a white solid and α anomer 330 (380 mg, 45%) as a foam.

329: UV (MeOH) $\lambda_{max}$ 265.0 nm.; 330: UV (MeOH) $\lambda_{max}$ 265.0 nm.

(332).

6-Amino-2-fluoro-9-[5-O-(tert-butyldimethylsilyl)-2,3-dideoxy-2-fluoro-β-L-gycero-pent-2-enofuranosyl]purine (331) and 6-Chloro-2-amino-9-[-5-O-(tert-butyldimethylsilyl)-2,3-dideoxy-2-fluoro-β-L-gycero-pent-2-enofuranosyl]purine (332)

Dry ammonia was bubbled into a stirred solution of 327 (420 mg, 1.04 mmol) in dry DME (35 mL) at room temperature overnight. The salts were removed by filtration and the filtrate was evaporated under reduced pressure. The residue was purified by silica gel column chromatography (25% EtOAc/hexanes) to give two compounds, 331 (114 mg, 0.30 mmol) as a white solid and 332 (164 mg, 0.41 mmol) as a white solid.

331: UV (MeOH) $\lambda_{max}$ 268.5 nm. Anal. (C$_{16}$H$_{23}$F$_2$NsO$_2$ Si0.2Acetone) C, H, N, 332:UV (MeOH) $\lambda_{max}$ 307.5 nm. Anal. (C$_{16}$H$_{23}$FN$_5$O$_2$ ClSi) C, H, N, Cl.

6-Amino-2-fluoro-9-[5-O-(tert-butyldimethylsilyl)-2,3-dideoxy-2-fluoro-α-L-gycero-pent-2-enofuranosyl]purine (333) and 6-Chloro-2-amino-9-[-5-O-(tert-butyldimethylsilyl)-2,3-dideoxy-2-fluoro-α-L-gycero-pent-2-enofuranosyl] purine (334).

Dry ammonia was bubbled into a stirred solution of 333 (420 mg, 1.04 mmol) in dry DME (35 mL) at room temperature overnight. The salts were removed by filtration and the filtrate was evaporated under reduced pressure. The residue was purified by silica gel column chromatography (25, % EtOAc/hexanes) to give two compounds, 332 (150 mg, 0.38 mmol) as a white solid and 333 (69.3 mg, 0.18 mmol) as a white solid.

333: UV (MeOH) $\lambda_{max}$ 269.0 nm. Anal. (C$_{16}$H$_{23}$F$_2$N$_5$O$_2$Si0.3Acetone) C, H, N, 334: UV (MeOH) $\lambda_{max}$ 309.5 nm. Anal. (C$_{16}$H$_{23}$F ClN$_5$O$_2$Si) C, H, N.

9-(2,3-dideoxy-2-fluoro-β-L-gycero-pent-2-enofuranosyl)adenine (335). A solution of 329 (100 mg, 0.369 mmol) and saturated NH$_3$/MeOH (50 mL) was heated at 90° C. in a steel bomb for 24 h. After cooling to room temperature, the solvent was removed under reduced pressure and the residual syrup was purified by column chromatography using 6% MeOH/CHCl$_3$ as an eluent to give 335 (70 mg, 75%) as a white solid. 335: UV (H$_2$O) $\lambda_{max}$ 258 nm (ϵ18,800) (pH 2), 258.5 nm (ϵ18,800) (pH 7), 258.5 nm (ϵ19,100) (pH 11). Anal. (C$_{10}$H$_{10}$FN$_5$O$_2$.0.2H$_2$O) C, H, N.

9-(2,3-dideoxy-2-fluoro-α-L-gycero-pent-2-enofuranosyl)adenine (336). A solution of 330 (99 mg, 0.366 mmol) and saturated NH$_3$/MeOH (50 mL) was heated at 90° C. in a steel bomb for 24 h. After cooling to room temperature, the solvent was removed under reduced pressure and the residual syrup was purified by column chromatography using 6% MeOH/CHCl$_3$ as an eluent to give 336 (72 mg, 78%) as a white solid.

336: UV (H$_2$O) $\lambda_{max}$ 258 nm (ϵ21,100) (pH 2), 259 nm (ϵ21,500) (pH 7), 259 nm (ϵ22,600) (pH 11). Anal. (C$_{10}$H$_{10}$FN$_5$O$_2$.0.3MeOH) C, H, N.

9-(2,3-dideoxy-2-fluoro-β-L-gycero-pent-2-enofuranosyl)hypoxanthine (337). A mixture of 329 (100 mg, 0.369 mmol), NaOMe (0.5 M solution in MeOH) (2.94 mL, 1.46 mmol) and HSCH$_2$CH$_2$OH (0.1 mL, 1.46 mmol) in MeOH (20 mL) was refluxed for 4 h under nitrogen. The reaction mixture was cooled, neutralized with glacial AcOH and evaporated to dryness under vacuum. The residue was purified by silica gel column chromatography (10% MeOH/CHCl$_3$) to afford 337 (74 mg, 80%) as a white solid. 37: UV (H$_2$O) $\lambda_{max}$ 247 nm (ϵ12,400) (pH 2), 247.5 nm (ϵ13,000) (pH 7), 253 nm (ϵ13,100) (pH 11). Anal. (C$_{10}$H$_9$FN$_4$O$_3$.0.2H$_2$O) C, H, N.

9-(2,3-dideoxy-2-fluoro-α-L-gycero-pent-2-enofuranosyl)hypoxanthine (338). A mixture of 330 (100 mg, 0.369), NaOMe (0.5 M solution in MeOH) (2.94 mL, 1.46 mmol) and HSCH$_2$CH$_2$OH (0.1 mL, 1.46 mmol) in MeOH (20 mL) was refluxed for 4 h under nitrogen. The reaction mixture was cooled, neutralized with glacial AcOH and evaporated to dryness under vacuum. The residue was purified by silica gel column chromatography (10% MeOH/CHCl$_3$) to afford 338 (70 mg, 80%) as a white solid. 338: UV (H$_2$O) $\lambda_{max}$ 247.5 nm (ϵ12,700) (pH 2), 247.5 nm (ϵ13,700) (pH 7), 252.5 nm (ϵ13,100)(pH 11). Anal. ($C_{10}H_9FN_4O_3 \cdot 0.3H_2O$) C, H, N.

2-Fluoro-6-amino-9-(2,3-dideoxy-2-fluoro-β-L-gycero-pent-2-enofuranosyl)purine (339). A solution of 31 (101 mg, 0.26 mmol) in dry acetonitrile (15 mL) was treated with TBAF (1 M solution in THF) (0.35 mL, 0.35 mmol) and stirred for 30 min. After evaporation of solvent, the dryness was purified by column chromatography (9% $CH_2Cl_2$/MeOH) to obtain 339 (64.7 mg, 0.24 mmol, 92.3%) as a white crystalline solid. UV ($H_2O$) $\lambda_{max}$ 269.0 nm (pH 7).

2-Fluoro-6-amino-9-(2,3-dideoxy-2-fluoro-α-L-gycero-pent-2-enofuranosyl)purine (340). A solution of 333 (73.4 mg, 0.19 mmol) in dry acetonitrile (10 mL) was treated with TBAF (1 M solution in THF) (0-25 mL, 0.25 mmol) and stirred for 30 min. After evaporation of solvent, the dryness was purified by column chromatography (9% $CH_2Cl_2$/MeOH) to obtain 340 (46.2 mg, 0.17 mmol, 90.3%) as a white crystalline solid. UV ($H_2O$) $\lambda_{max}$ 269.0 nm (pH 7).

2-Amino-6-chloro-9-(2,3-dideoxy-2-fluoro-β-L-gycero-pent-2-enofuranosyl)purine (341). A solution of 332 (143.5 mg, 0.40 mmol) in dry acetonitrile (15 mL) was treated with TBAF (1 M solution in THF) (0.6 mL, 0.60 mmol) and stirred for 30 min. After evaporation of solvent, the dryness was purified by column chromatography (5% $CH_2Cl_2$/MeOH) to obtain 341 (109 mg, 0.382 mmol, 95.5%) as a white crystalline solid. UV ($H_2O$) $\lambda_{max}$ 308.5 nm (pH 7).

2-Amino-6-chloro-9-(2,3-dideoxy-2-fluoro-α-L-gycero-pent-2-enofuranosyl)purine (342). A solution of 334 (145 mg, 0.36 mmol) in dry acetonitrile (10 mL) was treated with TBAF (1 M solution in THF) (0.5 mL, 0.50 mmol) and stirred for 30 min. After evaporation of solvent, the dryness was purified by column chromatography (9% $CH_2Cl_2$/MeOH) to obtain 342 (99.9 mg, 0.35 mmol, 96.4%) as a white crystalline solid. UV ($H_2O$) $\lambda_{max}$ 309.0 nm (pH 7).

9-(2,3-dideoxy-2-fluoro-β-L-gycero-pent-2-enofuranosyl)guanine (343). A mixture of 341 (63.6 mg, 0.223 mmol), 2-mercaptoethanol (0.06 mL, 0.89 mmol) and 1 N NaOMe (0.89 mL, 0.89 mmol) in MeOH (10 mL) was refluxed for 5 h under nitrogen. The mixture was cooled, neutralized with glacial AcOH and concentrated to dryness under reduced pressure. The residue was purified by column chromatography (12% $CH_2Cl_2$/MeOH) to obtain 343 (30.1 mg, 0.113 mmol, 50.7%) as a white solid. UV ($H_2O$) $\lambda_{max}$ 253.5 nm (pH 7).

9-(2,3-dideoxy-2-fluoro-α-L-gycero-pent-2-enofuranosyl)guanine (344). A mixture of 342 (59.3 mg, 0.208 mmol), 2-mercaptoethanol (0.07 mL, 1.04 mmol) and 1 N NaOMe (1.04 mL, 1.04 mmol) in MeOH (10 mL) was refluxed for 5 h under nitrogen. The mixture was cooled, neutralized with glacial AcOH and concentrated to dryness under vacuum. The residue was purified by column chromatography (12.5% $CH_2Cl_2$/MeOH) to obtain 344 (28.0 mg, 0.105 mmol, 50.5%) as a white solid. UV ($H_2O$) $\lambda_{max}$ 253.0 nm (pH 7).

Synthesis of cis-(±)-Carbocyclic d4 Cytosine Nucleosides and their 5'-Triphosphates Referring to Scheme 11, starting from diethyl diallylmalonate (701), the 4-carbethoxy-1,6-heptadiene (702) was synthesized in 78% yield (W. A. Nugent, *J. Am. Chem. Soc.*, 1995, 117, 8992-8998). Compound 703 was synthesized from compound 702 in 71% yield (L. E. Martinez, *J. Org Chem.*, 1996, 61, 7963-7966), and compound 705 was synthesized from compound 704 in 43% yield (D. M. Hodgson, *J. Chem. Soc. Perkin Trans. I*, 1994, 3373-3378). The key intermediate cis-(±)-3-acetoxy-5-(acetoxymethyl) cyclopentene (708) can be alternatively synthesized from cyclopentadiene and formaldehyde in acetic acid using a Prins reaction (E. A. Saville-Stones, *J. Chem. Soc. Perkin Trans. I*, 1991, 2603-2604) albeit it suffers low yield and inseparable problems; or from a bicyclic lactone which was synthesized by multiple steps through 4 steps (F. Burlina, *Bioorg. Med. Chem. Lett.*, 1997, 7, 247-250). The latter methodology gave a chiral 708 [(−)-enantiomer], although it needed to synthesized a chiral bicyclic lactone. $N^4$-Acetyl-5-fluorocytosine was synthesized from 5-fluorocytosine and p-nitrophenyl acetate (A. S. Steinfeld, *J. Chem. Research* (*M*), 1979, 1437-1450).

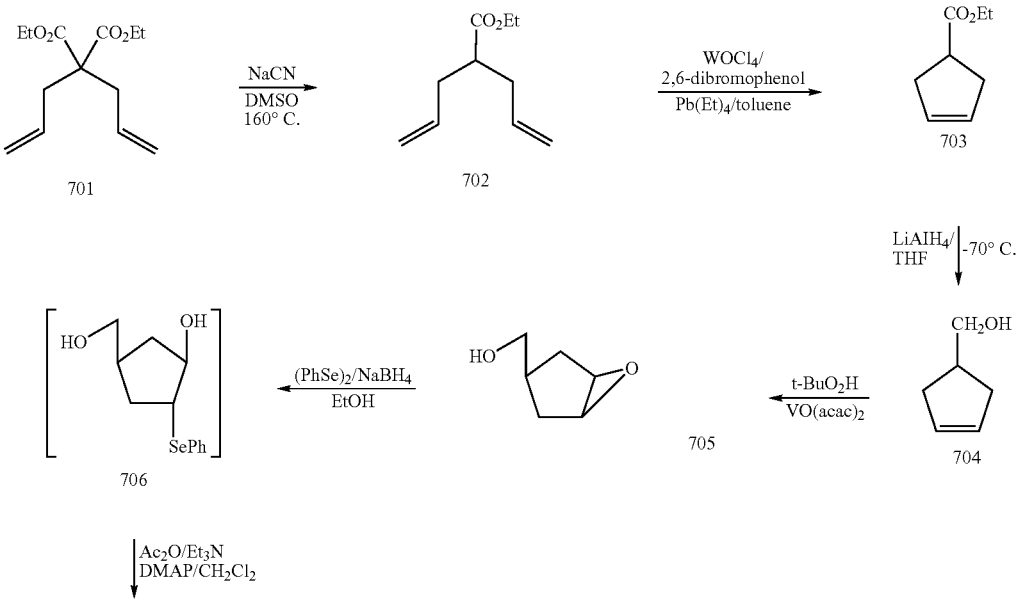

Scheme 11

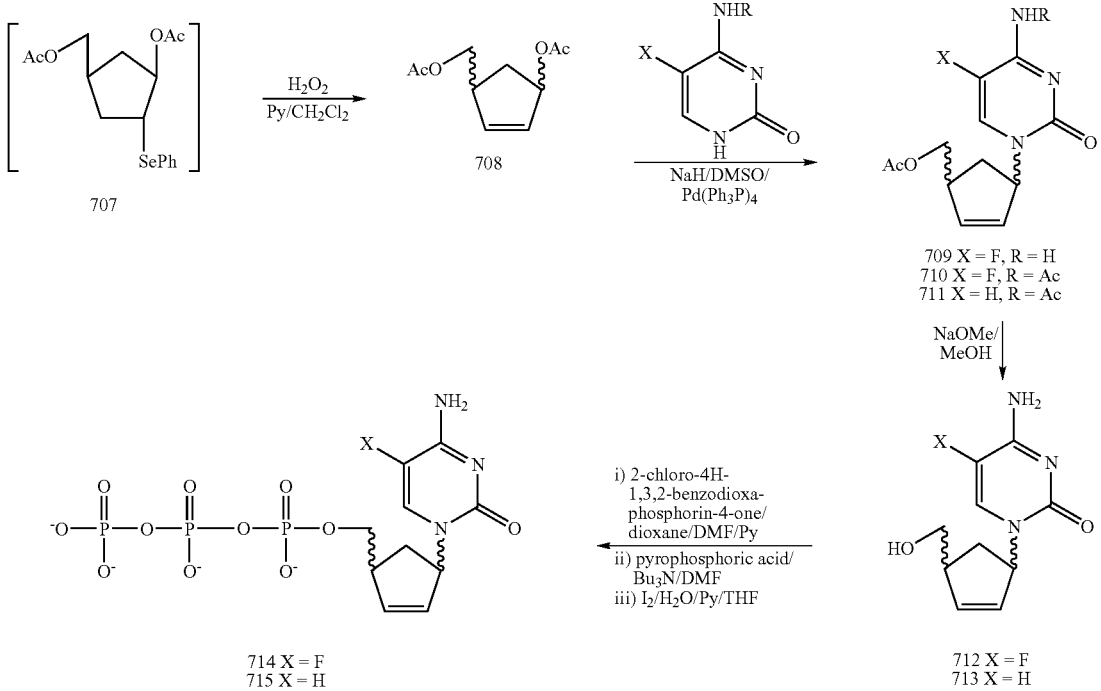

EXPERIMENTAL PART

General. All reagents were used as received unless stated otherwise. Anhydrous solvents were purchased from Aldrich Chemical Co. Melting points (M.p.) were determined on an Electrothermal digit melting point apparatus and are uncorrected. $^1$H and $^{13}$C NMR spectra were taken on a Varian Unity Plus 400 spectrometer at room temperature and reported in ppm downfield from internal tetramethylsilane.

4-Carbethoxy-1,6-heptadiene (702). A mixture of diethyl diallymalonate (701; 50 g, 208 mmol), sodium cyanide (20.7 g, 422 mmol) and DMSO (166 mL) was heated at 160° C. for 6 h. After being cooled to r.t., the mixture was added to 400 mL of water and the product was extracted into hexane (4×100 mL). After evaporation of the solvent at reduced pressure, the residue was distilled (42-43° C./1 Torr) to give 27.34 g (78%) of 702 as a colorless liquid. $^1$H NMR (400 MHz, CDCl$_3$) δ 5.80-5.70 (m, 2H, 2 CH=CH$_2$), 5.10-5.02 (m, 4H, 2 CH=CH$_2$), 4.14 (q, 2H, J=7.2 Hz, OCH$_2$), 2.54-2.48 (m, 1H, CH), 2.41-2.34, 2.29-2.23 (2m, 4H, 2 CH$_2$), 1.25 (t, J=7.2 Hz, 3H, CH$_3$).

(±)-3-Cyclopentenecarboxylic Acid, Ethyl Ester (703). A flame-dried 500 mL flask was charged with 2,6-dibromophenol (1.20 g, 4.76 mmol), tungsten oxychloride (0.813 g, 2.38 mmol), and anhydrous toluene (25 mL). The resulting suspension was heated at reflux under nitrogen for 1 h, and then the solvent was evaporated in vacuo. The solid residue was broken up with a spatula and dried in vacuo for 30 min. To the residue were added toluene (160 mL), Et$_4$Pb (1.54 g, 4.76 mL), and 702 (22 g, 131.0 mmol). The mixture was heated at 90° C. under nitrogen for 1.5 h. After being cooled to r.t., the mixture was filtered through a celite, and the celite was rinsed with t-BuOMe. The combined filtrates were washed with 1% NaOH soln, water, and brine, and concentrated by evaporation at reduced pressure. The residue was distilled (37-38° C./1 Torr) to give 13-06 g (71%) of 703 as a colorless liquid. $^1$H NMR (400 MHz, CDCl$_3$) δ 5.67 (s, 2H, CH=CH), 4.14 (q, 2H, J=7.2 Hz, OCH$_2$), 3.11 (pentuplet, J=7.6 Hz, 1H, CH), 2.65 (d, J=7.6 Hz, 4H, 2 CH$_2$), 1.27 (t, J=7.2 Hz, 3H, CH$_3$).

(±)-1-(Hydroxymethyl)-3-cyclopentene (704). To a cold (−78° C.) solution of 703 (7 g, 50 mmol) in dry THF (150 mL) was added LiAlH$_4$ (1 M soln in THF, 25 mL, 25 mmol), and the reaction solution was stirred at −78° C. under argon for 4 h. Then the reaction solution was allowed to warm to 0° C., and 2.5 mL of water, 2.5 mL of 15% NaOH, and 7.5 mL of water were added sequentially. After warming to r.t., the precipitates were filtered through a celite, and the celite was washed with hot EtOAc. The combined filtrates were washed with 0.1 N NaOH, and brine, dried (MgSO$_4$), filtered, concentrated and dried in vacuo to give 4.294 g (84%) of 704 as a pale yellow liquid. $^1$H NMR (400 MHz, CDCl$_3$)δ 5.68 (s, 2H, 2 CH=CH), 3.57 (d, J=6.0 Hz, 2H, CH$_2$OH), 2.54-2.48 (m, 3H, CH+CH$_2$), 2.15-2.10 (m, 2H, CH$_2$).

cis-(±)-4-(Hydroxymethyl)-1,2-epoxycyclopentane (705). To a solution of 704 (930 mg, 9.1 mmol), and vanadyl acetylacetonate (10 mg) in anhydrous CH$_2$Cl$_2$ (20 mL) was added t-BuO$_2$H ~3 M soln in CH$_2$Cl$_2$, prepared from a mixture of t-BuO$_2$H (70% by weight in water, 41 mL, 0.3 mol) and CH$_2$Cl$_2$ (59 mL) by drying (2×MgSO$_4$) and storage over 4 A molecular sieve, 10 mL, ~30 mmol] dropwise. After stirring at r.t. for 24 h, aqueous Na$_2$SO$_3$ (15% soln, 60 mL) was added, and the mixture was stirred at r.t. for 6 h. The organic layer was separated, washed with sat. NaHCO$_3$, and brine, and concentrated. The residue was purified by flash chromatography on silica gel eluting with hexane/EtOAc (2:1) to give 460 mg (43%) of 705 as a colorless liquid. $^1$H NMR (400 MHz, CDCl$_3$)δ 3.54 (s, 2H, (CH)$_2$O), 3.49 (t, J=4.0 Hz, 2H, CH$_2$OH), 2.95 (bs, 1H, OH), 2.44-

2.40 (m, 1H, CH), 2.05-2.02 (m, 4H, 2 CH$_2$). $^{13}$C NMR (100 MHz, CDCl$_3$)δ 66.9 (d, (CH$_2$)$_2$O), 59.2 (t, CH$_2$OH), 36.5 (d, CH), 31.4 (t, 2 CH$_2$).

cis-(±)-3-Acetoxy-5-(acetoxymethyl)cyclopentene (708). To a solution of diphenyl diselenenide (2.70 g, 8.65 mmol) in anhydrous EtOH (100 mL) was added NaBH$_4$ in portions. The solution was stirred until the yellow color turned to colorless, and then a solution of 705 (1.70 g, 14.4 mmol) in anhydrous THF (10 mL) was added. The reaction solution was heated at reflux for 1 h under nitrogen, and then the solvent was evaporated in vacuo. To the residue was added EtOAc (80 mL) and water (30 mL). The organic phase was separated, washed with brine, dried (MgSO$_4$), filtered, concentrated and dried in vacuo. The obtained (±)-1-hydroxy-4-(hydroxymethyl)-2-(phenylselenenyl)-cyclopentane (706; light yellow oil) was used for the next reaction directly without further purification. To the crude product 706 were added anhydrous CH$_2$Cl$_2$ (60 mL), Et$_3$N (30 mL, 216 mmol), and DMAP (50 mg). The resulting solution was cooled to 0° C., and Ac$_2$O (14.7 g, 144 mmol) was added dropwise. After being stirred at r.t. under argon overnight, evaporation of the solvent provided (±)-1-acetoxy-4-(acetoxymethyl)-2-(phenylselenenyl)-cyclopentane (707; light yellow oil). To a cold (0° C.) solution of 707 in CH$_2$Cl$_2$ (50 mL) containing 3 drops of pyridine was added 30% H$_2$O$_2$ soln (20 mL) over a period of 5 min. After being stirred at 0° C. for 30 min and at r.t. for another 30 min, the reaction mixture was diluted by addition of CH$_2$Cl$_2$ (50 mL). The organic phase was separated, washed with water, sat. NaHCO$_3$, and brine, dried (MgSO$_4$), filtered, and concentrated by evaporation in vacuo. The residue was purified by flash chromatography on silica gel eluting with 0-10% EtOAc in hexane to give 2.254 g (79%, for the three steps) of 708 as a pale brown liquid. $^1$H NMR (400 MHz, CDCl$_3$)δ 6.01-6.00, 5.92-5.90 (2m, 2H, CH=CH), 5.66-5.64 (m, 1H, H-3), 4.04 (d, J=6.8 Hz, 2H, CH$_2$O), 2.98-2.92 (m, 1H, H-5), 2.53-2-46 (m, 1H, H-4a), 2.08, 2.04 (2s, 6H, 2 CH$_3$), 1.60-1.54 (m, 2H, H4b). $^{13}$C NMR (100 MHz, CDCl$_3$)δ 171.1, 170.9 (2s, 2 C=O), 137.0, 131.4 (2d, CH=CH), 79.2 (d, C-3), 67.4 (t, CH$_2$O), 43.7 (d, C-5), 33.4 (t, C-4), 21.3, 20.9 (2q, 2 CH$_3$).

cis-(±)-Carbocyclic 5'-O-acetyl-2',3'-didehydro-2',3'-dideoxy-5-fluorocytidine (709). A suspension of 5-fluorocytosine (258 mg, 2 mmol) and NaH (58 mg, 2.4 mmol) in anhydrous DMSO (15 mL) was heated in a pre-warned oil bath at 70° C. for 30 min. Then the resulting solution was cooled to r.t., and Pd(PPh$_3$)$_4$ (73 mg, 0.063 mmol) and a solution of 708 (298 mg, 1.5 mmol) in anhydrous THF (2 mL) were added respectively. The reaction mixture was stirred at 70° C. under argon for 3 days. After removal of the solvent by evaporation in vacuo, the residue was treated with CH$_2$Cl$_2$ (50 mL). The precipitates were filtered through a celite, and the celite was washed with CH$_2$Cl$_2$. The combined filtrates were concentrated, and the residue was purified by flash chromatography on silica gel eluting with 0-5% MeOH in CH$_2$Cl$_2$ to give 40 mg (10%) of 709 as a light brown solid. Recrystallization from MeOH/CH$_2$Cl$_2$/hexane provided pure product as white powders. M.p. 182-184° C. $^1$H NMR (400 MHz, CDCl$_3$)δ 7.43 (d, J=6.0 Hz, 1H, H-6), 6.18-6.16 (m, 1H, H-3'), 5.83-5.81 (m, 1H, H-2'), 5.73-5.71 (m, 1H, H-1'), 4.23-4.21, 4.08-4.04 (2m, 2H, CH$_2$O), 3.14-3.12 (m, 1H, H4'), 2.92-2.84 (m, 1H, H-6'a), 2.08 (s, 3H, CH$_3$), 1.41-1.35 (m, 1H, H-6'b).

cis-(±)-Carbocyclic N$^4$,5'-O-diacetyl-2',3'-didehydro-2',3'-dideoxy-5-fluorocytidine (710).

In an analogy manner to the procedure for 709, the title compound 710 was prepared from 708 (560 mg, 2.828 mmol) and N$^4$-acetyl-5-fluorocytosine (726 mg, 4.24 mmol): 560 mg (64%, brown oil). This crude product was used directly for the next reaction without further purification.

cis-(±)-Carbocyclic N$^4$,5'-O-diacetyl-2',3'-didehydro-2',3'-dideoxycytidine (711). In an analogy manner to the procedure for 709, the title compound 711 was prepared from 708 (272 mg, 1.37 mmol) and N$^4$-acetylcytosine (316 mg, 2.06 mmol): 108 mg (27%) of white powders. M.p. 169.5-171.5° C. $^1$H NMR (400 MHz, CDCl$_3$)δ 8.80 (bs, 1H, NH), 7.72 (d, J=6.8 Hz, 1H, H-6), 7.39 (d, J=6.8 Hz, 1H, H-5), 6.19-6.17 (m, 1H, H-3'), 5.86-5.81 (m, 1H, H-2'), 5.77-5.75 (m, 1H, H-1'), 4.17-4.13, 4.07-4.02 (2m, 2H, CH$_2$O), 3.18-3.10 (m, 1H, H4'), 2.96-2.88 (m, 1H, H-6'a), 2.27, 2.06 (2s, 6H, 2 CH$_3$), 1.43-1.37 (m, 1H, H-6'b). $^{13}$C NMR (100 MHz, CDCl$_3$)δ 170.8 (s, 2 C=O), 162.0 (s, C4), 155.6 (s, C-2), 145.3 (d, C-6), 139.2 (d, C-3'), 130.0 (d, C-2'), 96.8 (d, C-5), 66.3 (t, C-5'), 62.8 (d, C-1'), 44.2 (d, C-4'), 34.7 (t, C-6'), 25.0, 20.9 (2q, 2 CH$_3$).

cis-(±)-Carbocyclic 2',3'-didehydro-2',3'-dideoxy-5-fluorocytidine (712). To a flask containing 709 (33 mg, 0.12 mmol) was added NaOMe (0.5 M soln in MeOH, 0.5 mL). The reaction solution was stirred at r.t. for 1 h, and then the solvent was evaporated in vacuo. The residue was purified by flash chromatography on silica gel eluting with 5-10% MeOH in CH$_2$Cl$_2$ to give 17 mg (61%) of 712 as a light brown solid. Recrystallization from MeOH/CH$_2$Cl$_2$/hexane provided pure product as white powders. M.p. 205.5-206.0° C. $^1$H NMR (400 MHz, DMSO-d$_6$)δ 7.66 (d, J=6.0 Hz, 1H, H-6), 7.60, 7.40 (2bs, 2H, NH$_2$), 6.06-6.05 (m, 1H, H-3'), 5.68-5.65 (m, 1H, H-2'), 5.53-5.50 (m, 1H, H-1'), 4.77-4.75 (m, 1H, H-4'), 3.50-3.48, 3.41-3.37 (2m, 2H, H-5'),2.79-2.77 (m, 1H, H-6'a), 1.34-1.27 (m, 1H, H-6'b). $^{13}$C NMR (100 MHz, DMSO-d$_6$)δ 157.0 (d, J$_{C-F}$=11.9 Hz, C-4), 154.0 (s, C-2), 139.2 (d, C-3'), 135.8 (d, J$_{C-F}$=241.3 Hz, C-5), 130.2 (d, C-2'), 126.8 (d, J$_{C-F}$=11.8 Hz, C-6), 63.5 (t, C-5'), 61.3 (d, C-1'), 47.2 (d, C-4'), 33.3 (t, C-6'). MS (FAB) m/e 226 (MH$^+$). Anal. (C$_{10}$H$_{12}$FN$_3$O$_2$) calcd C, 53.33; H, 5.37; N, 18.66; found C, 53.10; H, 5.40; N, 18.44. In an analogy manner to the above procedure, the title compound 712 was also prepared from 710 (750 mg, 2.42 mmol): 320 mg (59%, white powders).

cis-(±)-Carbocyclic 2',3'-didehydro-2',3'-dideoxycytidine (713). In an analogy manner to the procedure for 712, the title compound 713 was prepared from 711 (75 mg, 0.257 mmol): 48 mg (90%, white solid). M.p. 200-201° C. $^1$H NMR (400 MHz, DMSO-d$_6$)δ 7.40 (d, J=7.2 Hz, 1H, H-6), 7.03, 6.95 (2bs, 2H, NH$_2$), 6.07-6.05 (m, 1H, H-3'), 5.67 (d, J=7.2 Hz, 1H, H-5), 5.65-5.64 (m, 1H, H-2'), 5.55-5.52 (m, 1H, H-1'), 4.714.68 (m, 1H, H4'), 3.43-3.36 (m, 2H, H-5'), 2.78-2.76 (m, 1H, H-6'a), 1.24-1.18 (m, 1H, H-6'b). $^{13}$C NMR (100 MHz, DMSO-d$_6$)δ 165.5 (s, C-4), 155.8 (s, C-2), 142.2 (d, C-6), 138.6 (d, C-3'), 130.5 (d, C-2'), 93.7 (d, C-5), 63.9 (t, C-5'), 60.8 (d, C-1'), 47.3 (d, C-4'), 34.0 (t, C-6'). MS (FAB) m/e 208 (MH$^+$). Anal. (C$_{10}$H$_{13}$N$_3$O$_2$) calcd D 57.96, H 6.32, N 20.28; found C, 57.35; H, 6.27; N, 20.02. HRMS (FAB) calcd for (C$_{10}$H$_{14}$N$_3$O$_2$): 208.1086; found 208.1088.

cis-(±)-Carbocyclic 2',3'-didehydro-2',3'-dideoxy-5-fluorocytidine 5'-triphosphate, triethylhydrogenammonium salt (714). To a solution of 712 (10 mg) in anhydrous DMF (0.3 mL) and pyridine (0.1 ml) was added a 1 M solution of 2-chloro-4H-1,3,2-benzodioxaphosphorin-4-one in anhydrous 1,4-dioxane (0.05 mL). The reaction solution was stirred at r.t. for 15 min. Then, a solution of 1 M pyrophosphoric acid-Bu$_3$N in anhydrous DMF (0.12 mL), and Bu$_3$N (0.05 mL) was added sequentially. After stirring at r.t. for another 15 min, a solution of I$_2$/H$_2$O/pyridine/THF was added to the above solution dropwise until the iodine color persisted (about 0.5 mL), and then the mixture was concentrated by evaporation in vacuo. The residue was dissolved in water (2 mL), washed with $CH_2Cl_2$ (3×1 mL), filtered, and purified by FPLC (column: HiLoad 26/10 Q Sepharose Fast Flow; buffer A: 0.01 M $Et_3NHCO_3$; buffer B: 0.7 M $Et_3NHCO_3$; flow rate: 10 mL/min; gradient: increasing buffer B from 0% at beginning to 10% at 4 min, then to 100% at 64 min). Collection and lyophilization of the appropriate fractions afforded 714 as a colorless syrup. HPLC [column: 100×4.6 mm Rainin Hydropore SAX ionic exchange; buffer A: 10 mM $NH_4H_2PO_4$ in 10% $MeOH/H_2O$ (pH 5.5); buffer B: 125 mM $NH_4H_2PO_4$ in 10% $MeOH/H_2O$ (pH 5.5); flow rate: 1.0 mL/min; gradient: increasing B from 0% at beginning to 100% at 25 min] retention time: 11.9 min. MS (FAB) m/e 464 ($[M-H]^+$).

cis-(±)-Carbocyclic 2',3'-didehydro-2',3'-dideoxycytidine 5'-phosphate (715). In an analogy manner to the procedure for 714, the title compound 715 was prepared from 713. HPLC (same conditions as above) retention time: 12.1 min. MS (FAB) m/e 446 ($[M-H]^+$).

Inhibitory Effect of (±)-Carboxy-D4FC-Triphosphate Against HIV-1 Reverse Transcriptase.

Extension assays were performed using a $r(I)_n.(dC)_{12}$-18 homopolymer template-primer (Pharmacia, Piscataway, N.J.) and the HIV-1 heterodimer p66/51 reverse transcriptase (RT, Biotechnology General, Rehovat, Israel). The standard reaction mixture (100 µl) contained 100 mM Tris hydrochloride (pH 8.0), 50 mM KCl, 2 mM $MgCl_2$, 0.05 units/ml $r(I)_n.(dC)_{12-18}$, 5 mM DTT, 100 µg/ml Bovine Serum Albumin, and 1 µM $^3$H-dCTP (23 Ci/mmol). 3TCTP (0.001-50 µM) was the positive control. Compounds were incubated 1 hr at 37° C. in the reaction mixture with 1 unit HIV-1 RT. The reaction was stopped with the addition of an equal volume of cold 10% TCA/0.05% sodium pyrophosphate and incubated 30 minutes at 4° C. The precipitated nucleic acids were harvested onto fiberglass filter paper using a Packard manual harvester (Meriden, Conn.). The radiolabel uptake in counts per minute (cpm) was determined using a Packard 9600 Direct Beta counter.

IV. Anti-HIV Activity

In one embodiment, the disclosed compounds or their pharmaceutically acceptable derivatives or salts or pharmaceutically acceptable formulations containing these compounds are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be-used prophylactically to prevent or retard the progression of clinical illness in individuals who are anti-HIV antibody or HIV-antigen positive or who have been exposed to HIV.

The ability of nucleosides to inhibit HIV can be measured by various experimental techniques. One technique, described in detail below, measures the inhibition of viral replication in phytohemagglutinin (PHA) stimulated human peripheral blood mononuclear (PBM) cells infected with HIV-1 (strain LAV). The amount of virus produced is determined by measuring the virus-coded reverse transcriptase enzyme. The amount of enzyme produced is proportional to the amount of virus produced.

Antiviral and cytotoxicity assays: Anti-HIV-1 activity of the compounds is determined in human peripheral blood mononuclear (PBM) cells as described previously (Schinazi, R. F.; McMillan, A.; Cannon, D.; Mathis, R.; Lloyd, R. M. Jr.; Peck, A.; Sommadossi, J.-P.; St. Clair, M.; Wilson, J.; Furman, P. A.; Painter, G.; Choi, W.-B.; Liotta, D.C. *Antimicrob. Agents Chemother.* 1992, 36, 2423; Schinazi, R. F.; Sommadossi, J.-P.; Saalmann, V.; Cannon, D.; Xie, M.-Y.; Hart, G.; Smith, G.; Hahn, E. *Antimicrob. Agents Chemother.* 1990, 34, 1061). Stock solutions (20-40 mM) of the compounds were prepared in sterile DMSO and then diluted to the desired concentration in complete medium. 3'-azido-3'-deoxythymidine (AZT) stock solutions are made in water. Cells are infected with the prototype HIV-$1_{LAI}$ at a multiplicity of infection of 0.01. Virus obtained from the cell supernatant are quantitated on day 6 after infection by a reverse transcriptase assay using $poly(rA)_n.oligo(dT)_{12-18}$ as template-primer. The DMSO present in the diluted solution (<0.1%) should have no effect on the virus yield. The toxicity of the compounds can be assessed in human PBM, CEM, and Vero cells. The antiviral $EC_{50}$ and cytotoxicity $IC_{50}$ is obtained from the concentration-response curve using the median effective method described by Chou and Talalay (*Adv. Enzyme Regul.* 1984, 22, 27).

Three-day-old phytohemagglutinin-stimulated PBM cells $10^6$ cells/ml) from hepatitis B and HIV-1 seronegative healthy donors are infected with HIV-1 (strain LAV) at a concentration of about 100 times the 50% tissue culture infectious dose (TICD 50) per ml and cultured in the presence and absence of various concentrations of antiviral compounds.

Approximately one hour after infection, the medium, with the compound to be tested (2 times the final concentration in medium) or without compound, is added to the flasks (5 ml; final volume 10 ml). AZT is used as a positive control.

The cells are exposed to the virus (about $2×10^5$ dpm/ml, as determined by reverse transcriptase assay) and then placed in a $CO_2$ incubator. HIV-1 (strain LAV) is obtained from the Center for Disease Control, Atlanta, Ga. The methods used for culturing the PBM cells, harvesting the virus and determining the reverse transcriptase activity are those described by McDougal et al. (*J. Immun. Meth.* 76, 171-183, 1985) and Spira et al. (*J. Clin. Meth.* 25, 97-99, 1987), except that fungizone was not included in the medium (see Schinazi, et al., *Antimicrob. Agents Chemother.* 32, 1784-1787 (1988); Id., 34:1061-1067 (1990)).

On day 6, the cells and supernatant are transferred to a 15 ml tube and centrifuged at about 900 g for 10 minutes. Five ml of supernatant are removed and the virus concentrated by centrifugation at 40,000 rpm for 30 minutes (Beckman 70.1 Ti rotor). The solubilized virus pellet is processed for determination of the levels of reverse transcriptase. Results are expressed in dpm/ml of sampled supernatant. Virus from smaller volumes of supernatant (1 ml) can also be concentrated by centrifugation prior to solubilization and determination of reverse transcriptase levels.

The median effective ($EC_{50}$) concentration is determined by the median effect-method (*Antimicrob. Agents Chemother.* 30, 491-498 (1986). Briefly, the percent inhibition of virus, as determined from measurements of reverse transcriptase, is plotted versus the micromolar concentration of compound. The $EC_{50}$ is the concentration of compound at which there is a 50% inhibition of viral growth.

Mitogen stimulated uninfected human PBM cells (3.8× $10^5$ cells/ml) can be cultured in the presence and absence of drug under similar conditions as those used for the antiviral assay described above. The cells are counted after 6 days using a hemacytometer and the trypan blue exclusion method, as described by Schinazi et al., *Antimicrobial*

*Agents and Chemotherapy*, 22(3), 499 (1982). The $IC_{50}$ is the concentration of compound which inhibits 50% of normal cell growth.

Table 7 provides data on the anti-HIV activity of selected compounds. Using this assay, it was determined that (±)-carbocyclic-D4FC-TP (2',3'-unsaturated-5-fluorocytidine) exhibited an $EC_{50}$ of 0.40 μM, and (±)-carbocyclic-D4C-TP (2',3'-unsaturated cytidine) exhibits an $EC_{50}$ of 0.38 μM.

V. Anti-Hepatitis B Activity

The ability of the active compounds to inhibit the growth of hepatitis virus in 2.2.15 cell cultures (HepG2 cells transformed with hepatitis virion) can be evaluated as described in detail below.

A summary and description of the assay for antiviral effects in this culture system and the analysis of HBV DNA has been described (Korba and Milman, 1991, *Antiviral Res.*, 15:217). The antiviral evaluations are optimally performed on two separate passages of cells. All wells, in all plates, are seeded at the same density and at the same time.

Due to the inherent variations in the levels of both intracellular and extracellular HBV DNA, only depressions greater than 3.5-fold (for HBV virion DNA) or 3.0-fold (for HBV DNA replication intermediates) from the average levels for these HBV DNA forms in untreated cells are considered to be statistically significant (P<0.05). The levels of integrated HBV DNA in each cellular DNA preparation (which remain constant on a per cell basis in these experiments) are used to calculate the levels of intracellular HBV DNA forms, thereby ensuring that equal amounts of cellular DNA are compared between separate samples.

Typical values for extracellular HBV virion DNA in untreated cells ranged from 50 to 150 pg/ml culture medium (average of approximately 76 pg/ml). Intracellular HBV DNA replication intermediates in untreated cells ranged from 50 to 100 μg/pg cell DNA (average approximately 74 pg/μg cell DNA). In general, depressions in the levels of intracellular HBV DNA due to treatment with antiviral compounds are less pronounced, and occur more slowly, than depressions in the levels of HBV virion DNA (Korba and Milman, 1991, *Antiviral Res.*, 15:217).

The manner in which the hybridization analyses can be performed for these experiments resulted in an equivalence of approximately 1.0 pg of intracellular HBV DNA to 2-3 genomic copies per cell and 1.0 pg/ml of extracellular HBV DNA to $3 \times 10^5$ viral particles/ml.

Toxicity analyses were performed to assess whether any observed antiviral effects are due to a general effect on cell viability. The method used herein are the measurement of the uptake of neutral red dye, a standard and widely used assay for cell viability in a variety of virus-host systems, including HSV and HIV. Toxicity analyses are performed in 96-well flat bottomed tissue culture plates. Cells for the toxicity analyses are cultured and treated with test compounds with the same schedule as described for the antiviral evaluations below. Each compound are tested at 4 concentrations, each in triplicate cultures (wells "A", "B", and "C"). Uptake of neutral red dye are used to determine the relative level of toxicity. The absorbance of internalized dye at 510 nm ($A_{sin}$) are used for the quantitative analysis. Values are presented as a percentage of the average $A_{sin}$ values in 9 separate cultures of untreated cells maintained on the same 96-well plate as the test compounds.

VI. Anti-Hepatitis C Activity

Compounds can exhibit anti-hepatitis C activity by inhibiting HCV polymerase, by inhibiting other enzymes needed in the replication cycle, or by other known methods. A number of assays have been published to assess these activities.

WO 97/12033, filed on Sep. 27, 1996, by Emory University, listing C. Hagedom and A. Reinoldus as inventors, and which claims priority to U.S. Ser. No. 60/004,383, filed on September 1995, describes an HCV polymerase assay that can be used to evaluate the activity of the compounds described herein. This application and invention is exclusively licensed to Triangle Pharmaceuticals, Inc., Durham, N.C. Another HCV polymerase assays has been reported by Bartholomeusz, et al., Hepatitis C virus (HCV) RNA polymerase assay using cloned HCV non-structural proteins; Antiviral Therapy 1996:1(Supp 4) 18-24.

VI. Treatment of Abnormal Cellular Proliferation

In an alternative embodiment, the compounds are used to treat abnormal cellular proliferation. The compound can be evaluated for activity by testing in a routine screen, such as that performed cost by the National Cancer Institute, or by using any other known screen, for example as described in WO 96/07413.

The extent of anticancer activity can be easily assessed by assaying the compound according to the procedure below in a CEM cellor other tumor cell line assay. CEM cells are human lymphoma cells (a T-lymphoblastoid cell line that can be obtained from ATCC, Rockville, Md.). The toxicity of a compound to CEM cells provides useful information regarding the activity of the compound against tumors. The toxicity is measured as $IC_{50}$ micromolar). The $IC_{50}$ refers to that concentration of test compound that inhibits the growth of 50% of the tumor cells in the culture. The lower the $IC_{50}$, the more active the compound is as an antitumor agent. In general, 2'-fluoro-nucleoside exhibits antitumor activity and can be used in the treatment of abnormal proliferation of cells if it exhibits a toxicity in CEM or other immortalized tumor cell line of less than 50 micromolar, more preferably, less than approximately 10 micromolar, and most preferably, less than 1 micromolar. Drug solutions, including cyclohex-imide as a positive control, are plated in triplicate in 50 μl growth medium at 2 times the final concentration and allowed to equilibrate at 37° C. in a 5% $CO_2$ incubator. Log phase cells are added in 50 μl growth medium to a final concentration of $2.5 \times 10^3$ (CEM and SK-MEL-28), $5 \times 10^3$ (MMAN, MDA-MB435s, SKMES-1, DU-145, LNCap), or $1 \times 10^4$ (PC-3, MCF-7) cells/well and incubated for 3 (DU-145, PC-3, MMAN), 4 (MCF-7, SK-MEL-28, CEM), or 5 (SK-MES-1, MDA-MB435s, LNCaP) days at 37° C. under a 5% $CO_2$ air atmosphere. Control wells include media alone (blank) and cells plus media without drug. After growth period, 15 μl of Cell Titer 96 kit assay dye solution (Promega, Madison, Wis.) are added to each well and the plates are incubated 8 hr at 37° C. in a 5% $CO_2$ incubator. Promega Cell Titer 96 kit assay stop solution is added to each well and incubated 4-8 hr in the incubator. Absorbance is read at 570 nm, blanking on the medium-only wells using a Biotek Biokinetics plate reader (Biotek, Winooski, Vt.). Average percent inhibition of growth compared to the untreated control is calculated. $IC_{50}$, $IC_{90}$, slope and r value ate calculated by the method of Chou and Talalay. Chou T-C, Talalay P. Quantitative analysis of dose-effect relationships: The combined effects of multiple drugs or enzyme inhibitors. Adv Enzyme Regul 1984, 22:27-55.

The active compound can be administered specifically to treat abnormal cell proliferation, and in particular, cell hyperproliferation. Examples of abnormal cell proliferation include, but are not limited to: benign tumors, including, but not limited to papilloma, adenoma, firoma, chondroma, osteoma, lipoma, hemangioma, lymphangioma, leiomyoma, rhabdomyoma, meningioma, neuroma, ganglioneuroma, nevus, pheochromocytoma, neurilemona, fibroadenoma, teratoma, hydatidiform mole, granuosa-theca, Brenner tumor, arrhenoblastoma, hilar cell tumor, sex cord mesenchyme, interstitial cell tumor, and thyoma as well as proliferation of smooth muscle cells in the course of development of plaques in vascular tissue; malignant tumors (cancer), including but not limited to carcinoma, including renal cell carcinoma, prostatic adenocarcinoma, bladder carcinoma, and adenocarcinoma, fibrosarcoma, chondrosarcoma, osteosarcoma, liposarcoma, hemangiosarcoma, lymphangiosarcomra, leiomyosarcoma, rhabdomyosarcoma, myelocytic leukemia, erythroleukemia, multiple myeloma, glioma, meningeal sarcoma, thyoma, cystosarcoma phyllodes, nephroblastoma, teratoma choriocarcinoma, cutaneous T-cell lymphoma (CTCL), cutaneous tumors primary to the skin (for example, basal cell carcinoma, squamous cell carcinoma, melanoma, and Bowen's disease), breast and other tumors infiltrating the skin, Kaposi's sarcoma, and premalignant and malignant diseases of mucosal tissues, including oral, bladder, and rectal diseases; preneoplastic lesions, mycosis fungoides, psoriasis, dermatomyositis, rheumatoid arthritis, viruses (for example, warts, herpes simplex, and condyloma acuminata), molluscum contagiosum, premalignant and malignant diseases of the female genital tract (cervix, vagina, and vulva). The compounds can also be used to induce abortion.

In this embodiment, the active compound, or its pharmaceutically acceptable salt, is administered in an effective treatment amount to decrease the hyperproliferation of the target cells. The active compound can be modified to include a targeting moiety that concentrates the compound at the active site. Targeting moieties can include an antibody or antibody fragment that binds to a protein on the surface of the target cell, including but not limited to epidermal growth factor receptor (EGFR), c-Esb-2 family of receptors and vascular endothelial growth factor (VEGF).

VII. Pharmaceutical Compositions

Humans suffering from any of the disorders described herein can be treated by administering to the patient an effective amount of the active compound or a pharmaceutically acceptable derivative or salt thereof in the presence of a pharmaceutically acceptable carrier or diluent. The active materials can be administered by any appropriate route, for example, orally, parenterally, intravenously, intradermally, subcutaneously, or topically, in liquid or solid form. A preferr weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50-1000 mg is usually convenient.

Ideally the active ingredient should be administered to achieve peak plasma concentrations of the active compound of from about 0.2 to 70 pM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable derivative or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention.

The invention claimed is:

1. A method for the treatment of a HCV infection in a host in need thereof comprising administering an effective treatment amount of a β-D-2'-fluoronucleoside, or a pharmaceutically acceptable salt or prodrug thereof, optionally in a pharmaceutically acceptable carrier or diluent.

2. The method of claim 1, wherein the β-D-2'-fluoronucleoside has a pyrimidine base.

3. The method of claim 2, wherein the pyrimidine base is selected from the group consisting of thymine, uracil, 5-halouracil, 5-fluorouracil, cytosine, 5-fluorocytosine, 5-methylcytosine, 6-aza-pyrimidine, 6-azacytosine, 2- and/or 4-mercaptopyrmidine, $C^5$-alkylpyrimidine, $C^5$-benzylpyrimidine, $C^5$-halopyrimidine, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, and $C^5$-aminopyrimidine.

4. The method of claim 2, wherein the pyrimidine base is thymine.

5. The method of claim 2, wherein the pyrimidine base is uracil.

6. The method of claim 2, wherein the pyrimidine base is 5-halouracil.

7. The method of claim 2, wherein the pyrimidine base is cytosine.

8. The method of claim 2, wherein the pyrimidine base is 5-fluorocytosine.

9. The method of claim 1, wherein the β-D-2'-fluoronucleoside has a purine base.

10. The method of claim 9, wherein the purine base is selected from the group consisting of $N^6$-alkylpurine, $N^6$-acylpurine (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, $N^2$-alkylpurine, $N^2$-alkyl-6-thiopurine, 5-azacytidinyl, guanine, adenine, hypoxanthine, 2,6-diaminopurine, and 6-chloropurine.

11. The method of claim 1, wherein the β-D-2'-fluoronucleoside has a triazolopyridinyl, imidazolopyridinyl, pyrrolopyrimidinyl, or pyrazolopyrimidinyl base.

12. The method of claim 1, wherein the β-D-2'-fluoronucleoside is in substantially pure form.

13. The method of claim 1, wherein the β-D-2'-fluoronucleoside is at least 90% by weight of the β-D-isomer.

14. The method of claim 1, wherein the β-D-2'-fluoronucleoside is at least 95% by weight of the β-D-isomer.

15. The method of claim 1, wherein the β-D-2'-fluoronucleoside is administered in the form of a dosage unit.

16. The method of claim 15, wherein the dosage unit contains 50-1000 mg of the compound.

17. The method of claim 15, wherein the dosage unit is in the form of a tablet or capsule.

18. The method of claim 1, wherein the pharmaceutically acceptable carrier is suitable for oral delivery.

19. The method of claim 1, wherein the pharmaceutically acceptable carrier is suitable for intravenous delivery.

20. The method of claim 1, wherein the pharmaceutically acceptable carrier is suitable for parenteral delivery.

21. The method of claim 1, wherein the pharmaceutically acceptable carrier is suitable for intradermal delivery.

22. The method of claim 1, wherein the pharmaceutically acceptable carrier is suitable for subcutaneous delivery.

23. The method of claim 1, wherein the pharmaceutically acceptable carrier is suitable for topical delivery.

24. The method of any one of claims 1-11, wherein the host is a human.

* * * * *

UNITED STATES PATENT AND TRADEMARK OFFICE
CERTIFICATE OF CORRECTION

PATENT NO. : 7,307,065 B2  
APPLICATION NO. : 10/796529  
DATED : December 11, 2007  
INVENTOR(S) : Raymond F. Schinazi et al.

Page 1 of 1

It is certified that error appears in the above-identified patent and that said Letters Patent is hereby corrected as shown below:

Column 1, line 12, "number AI32351" should read --grant numbers AI32351 and AI28731--

Signed and Sealed this

Twenty-third Day of June, 2009

JOHN DOLL  
*Acting Director of the United States Patent and Trademark Office*